(12) United States Patent
Braido et al.

(10) Patent No.: US 11,045,314 B2
(45) Date of Patent: *Jun. 29, 2021

(54) STENT FEATURES FOR COLLAPSIBLE PROSTHETIC HEART VALVES

(71) Applicant: St. Jude Medical, LLC, Abbott Park, IL (US)

(72) Inventors: Peter N. Braido, Wyoming, MN (US); Yousef F. Alkhatib, Edina, MN (US); Thomas M. Benson, Minneapolis, MN (US); Aaron J. Chalekian, Savage, MN (US); Ott Khouengboua, Chaska, MN (US); Julia A. Schraut, Shoreview, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 118 days.

This patent is subject to a terminal disclaimer.

(21) Appl. No.: 16/562,726

(22) Filed: Sep. 6, 2019

(65) Prior Publication Data
US 2019/0388224 A1 Dec. 26, 2019

Related U.S. Application Data

(63) Continuation of application No. 15/868,031, filed on Jan. 11, 2018, now Pat. No. 10,441,417, which is a
(Continued)

(51) Int. Cl.
*A61F 2/24* (2006.01)
*A61F 2/915* (2013.01)

(52) U.S. Cl.
CPC .......... *A61F 2/2418* (2013.01); *A61F 2/915* (2013.01); *A61F 2002/91575* (2013.01);
(Continued)

(58) Field of Classification Search
CPC ......... A61F 2/24; A61F 2/2412; A61F 2/2418
See application file for complete search history.

(56) References Cited

U.S. PATENT DOCUMENTS 3,657,744 A   4/1972   Ersek
4,275,469 A   6/1981   Gabbay
(Continued)

FOREIGN PATENT DOCUMENTS

DE   19857887 A1   7/2000
DE   10121210 A1   11/2002
(Continued)

OTHER PUBLICATIONS

Andersen et al., "Transluminal implantation of artificial heart valves", European Heart Journal, vol. 13, Issue 5, 704-708, May 1992.
(Continued)

*Primary Examiner* — Jason-Dennis N Stewart
(74) *Attorney, Agent, or Firm* — Lerner, David, Littenberg, Krumholz & Mentlik, LLP

(57) ABSTRACT

A prosthetic heart valve includes a stent having an expanded condition and a collapsed condition. The stent includes a plurality of distal cells, a plurality of proximal cells, a plurality of support struts coupling the proximal cells to the distal cells, and at least one support post connected to a plurality of proximal cells. The proximal cells are longitudinally spaced apart from the distal cells. Various strut configurations and connections of the struts to the proximal cells and of the proximal cells to the support post improve stent flexibility and reduce stress in the valve leaflets.

17 Claims, 38 Drawing Sheets

Related U.S. Application Data continuation of application No. 15/181,708, filed on Jun. 14, 2016, now Pat. No. 9,901,447, which is a continuation of application No. 14/304,293, filed on Jun. 13, 2014, now Pat. No. 9,387,072, which is a continuation of application No. 13/203,627, filed as application No. PCT/US2010/000561 on Feb. 25, 2010, now Pat. No. 8,808,366.

(60) Provisional application No. 61/208,834, filed on Feb. 27, 2009.

(52) U.S. Cl.
CPC . *A61F 2220/0075* (2013.01); *A61F 2230/008* (2013.01); *A61F 2230/0054* (2013.01); *A61F 2230/0067* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,697,971 A | 12/1997 | Fischell et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 5,984,973 A | 11/1999 | Girard et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |

(56) References Cited

U.S. PATENT DOCUMENTS

| | | |
|---|---|---|
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0234443 A1 | 9/2009 | Ottma et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1690515 A1 | 8/2006 |
| EP | 1913901 A1 | 4/2008 |
| EP | 1926455 A2 | 6/2008 |
| EP | 2074964 A1 | 7/2009 |
| EP | 2537487 A1 | 12/2012 |
| FR | 2 847 800 B1 | 6/2004 |
| FR | 2850008 A1 | 7/2004 |
| JP | 2004520879 A | 7/2004 |
| JP | 2007534381 A | 11/2007 |
| JP | 2008537891 A | 10/2008 |
| JP | 2008541863 A | 11/2008 |
| JP | 2010528761 A | 8/2010 |
| WO | 9117720 A1 | 11/1991 |

(56) References Cited

FOREIGN PATENT DOCUMENTS

| | | |
|---|---|---|
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 01056500 A2 | 8/2001 |
| WO | 2001054625 A1 | 8/2001 |
| WO | 2001076510 A2 | 10/2001 |
| WO | 0236048 A1 | 5/2002 |
| WO | 0247575 A2 | 6/2002 |
| WO | 02067782 A2 | 9/2002 |
| WO | 2003047468 A1 | 6/2003 |
| WO | 2005062980 A2 | 7/2005 |
| WO | 2005070343 A1 | 8/2005 |
| WO | 06073626 A2 | 7/2006 |
| WO | 2006070372 A2 | 7/2006 |
| WO | 2006127756 A2 | 11/2006 |
| WO | 07071436 A2 | 6/2007 |
| WO | 2007130537 A1 | 11/2007 |
| WO | 2008010817 A1 | 1/2008 |
| WO | 2008028569 A1 | 3/2008 |
| WO | 2008070797 A2 | 6/2008 |
| WO | 2008150529 A1 | 12/2008 |
| WO | 2009024716 A2 | 2/2009 |
| WO | 2009029199 A1 | 3/2009 |
| WO | 2009045338 A1 | 4/2009 |
| WO | 10008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Andersen, "Transluminal Catheter Implanted Prosthetic Heart Valves", International Journal of Angiology 7:102-106, Mar. 1998.

Buellesfeld et al., "Treatment of paravalvular leaks through inverventional techniques", Multimed Man Cardiothorac Surg MMCTS, 924, Jan. 2011.

Christie, G.W., et al., "On Stress Reduction in Bioprosthetic Valve Leaflets by the Use of a Flexible Stent," Journal of Cardiac Surgery, vol. 6, No. 4, 476-481, Dec. 1991.

De Cicco et al., "Aortic valve periprosthetic leakage: anatomic observations and surgical results", The Annals of thoracic surgery 79.5 (May 2005): 1480-1485.

Dewey et al., "Transapical aortic valve implantation: an animal feasibility study"; The annals of thoracic surgery, 82:110-6 (Feb. 13, 2006).

Gössl et al., "Percutaneous treatment of aortic and mitral valve paravalvular regurgitation", Current cardiology reports, vol. 15:388, pp. 1-8, Aug. 2013.

Heat Advisor, "Heart repairs without surgery. Minimally invasive procedures aim to correct valve leakage", Sep. 2004, PubMed ID 15586429.

Hourihan et al., "Transcatheter Umbrella Closure of Valvular and Paravalvular Leaks", Journal of the American College of Cardiology, vol. 20, No. 6, pp. 1371-1377, (Nov. 1992).

Huber, et al., "Direct-Access Valve Replacement", Journal of the American College of Cardiology, vol. 46, No. 2, (Jul. 19, 2005).

International Search Report and Written Opinion, PCT/US2010/000561, dated Jun. 1, 2010.

Japanese Office Action for Application No. 2011-552027 dated Dec. 10, 2013.

Knudsen et al., "Catheter-implanted prosthetic heart valves", The International Journal of Artificial Organs, vol. 16, No. 5, pp. 253-262, May 1993.

Krucinski, S., et al., "Numerical Simulation of Leaflet Flexure in Bioprosthetic Valves Mounted on Rigid and Expansile Stents," Journal of Biomechanics, vol. 26, No. 8, 929-943, Aug. 1993.

Lichtenstein et al., "Transapical Transcatheter Aortic Valve Implantation in Humans", Circulation, vol. 114, pp. 591-596 (Jul. 31, 2006).

Lichtenstein, "Closed heart surgery: Back to the future", The Journal of Thoracic and Cardiovascular Surgery, May 2006, vol. 131, No. 5, pp. 941-943.

Mack, "Minimally invasive cardiac surgery", Surgical Endoscopy, vol. 20, Supplement 2, pp. S488-S492, Apr. 2006.

Moazami et al., "Transluminal Aortic Valve Placement", ASAIO Journal, vol. 42(5), pp. M381-M385, Sep. 1996.

Muñoz et al., "Guidance of treatment of perivalvular prosthetic leaks", Current cardiology reports, vol. 16(1), p. 430, Jan. 2014.

Quaden et al., "Percutaneous aortic valve replacement: resection before implantation", European J. of Cardio-thoracic Surgery, vol. 27, Issue 5, pp. 836-840, May 2005.

Reis, R.L., et al., "The Flexible Stent: A New Concept in the Fabrication of Tissue Heart Valve Prostheses", The Journal of Thoracic and Cardiovascular Surgery, 683-689, Nov. 1971.

Reul, H., et al., "The geometry of the aortic root in health, at valve disease and after valve replacement," Journal of Biomechanics, vol. 23, No. 2, 181-91, 1990.

Rohde et al., "Resection of Calcified Aortic Heart Leaflets In Vitro by Q-Switched 2μm Microsecond Laser Radiation", Journal of Cardiac Surgery, vol. 30(2), pp. 157-162, Feb. 2015.

Ruiz, "Overview of PRE-CE Mark Transcatheter Aortic Valve Technologies", Euro PCR, dated May 25, 2010.

Swiatkiewicz et al., "Percutaneous closure of mitral perivalvular leak", Kardiologia polska, vol. 67(7), pp. 762-764, Jun. 2009.

Textbook "Transcatheter Valve Repair", 2006, pp. 165-186.

Walther et al., "Transapical approach for sutureless stent-fixed aortic valve implantation: experimental results", European Journal of Cardio-thoracic Surgery, vol. 29(5), pp. 703-708 (Jan. 30, 2006).

Webb et al., "Percutaneous Aortic Valve Implantation Retrograde From the Femoral Artery", Circulation, vol. 113:842-850, Jun. 2006.

Zegdi, Rachid, MD, PhD et al., "Is It Reasonable to Treat All Calcified Stenotic Aortic Valves With a Valved Stent?", 579-584, J. of the American College of Cardiology, vol. 51, No. 5, Feb. 5, 2008.

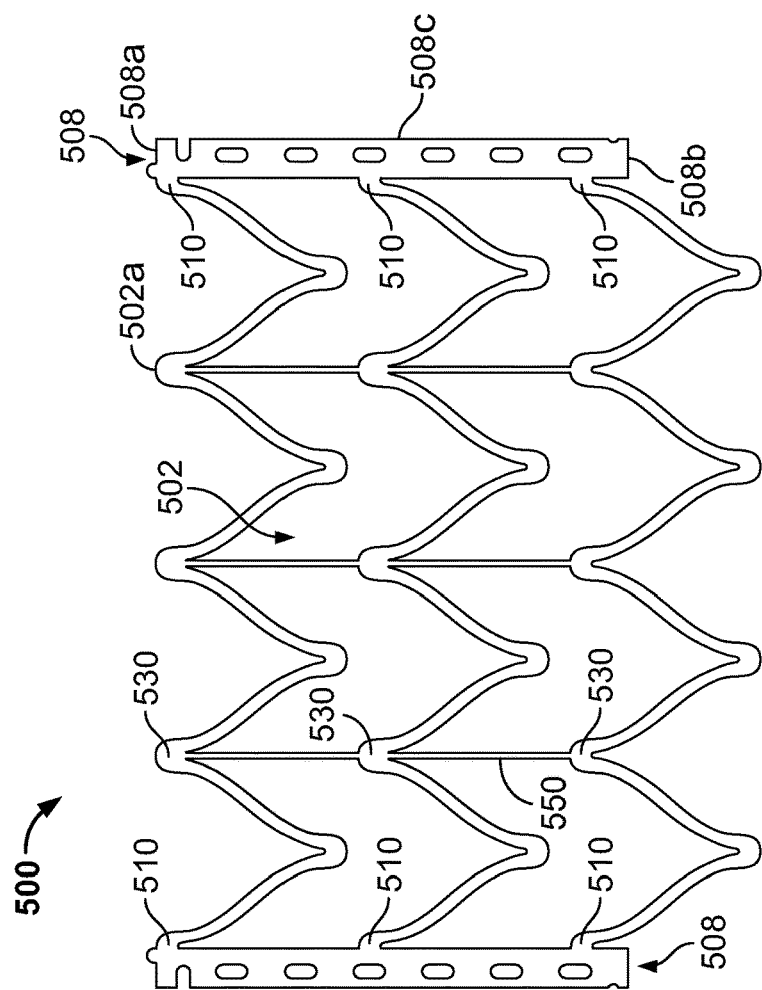
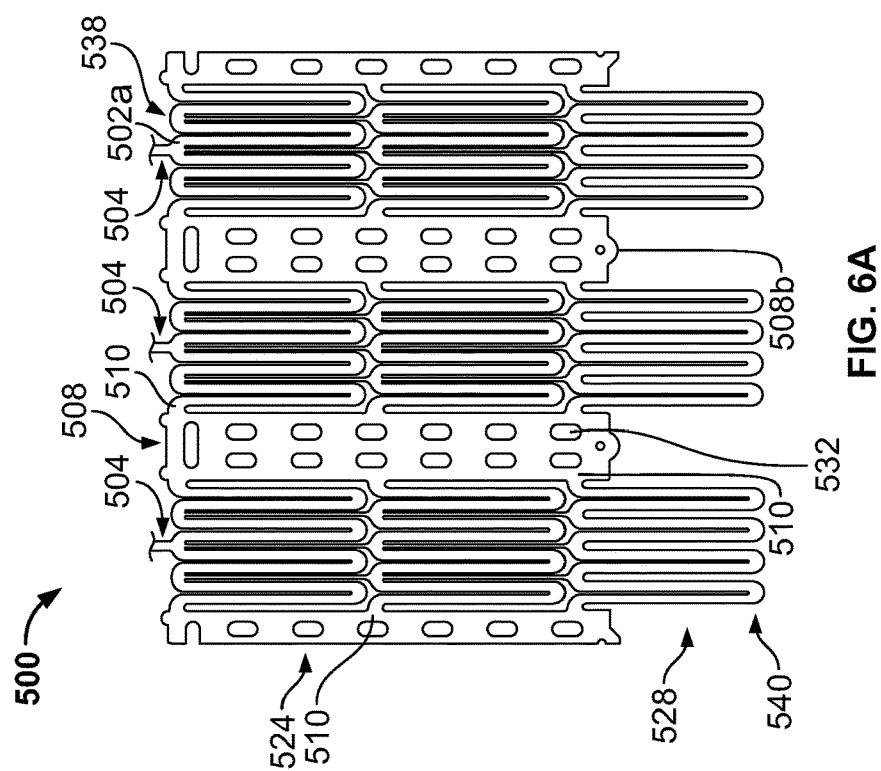
FIG. 6B
FIG. 6A

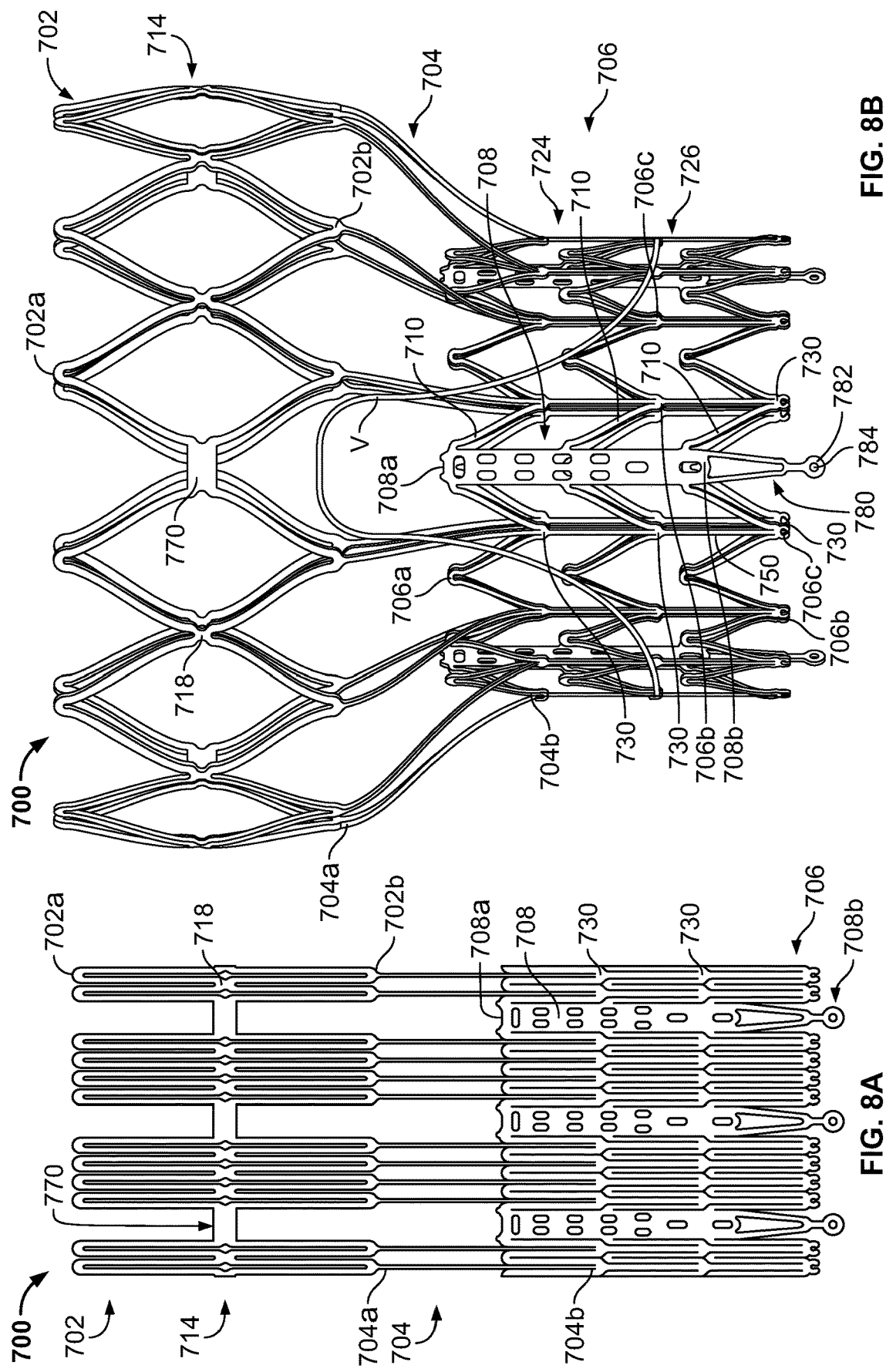

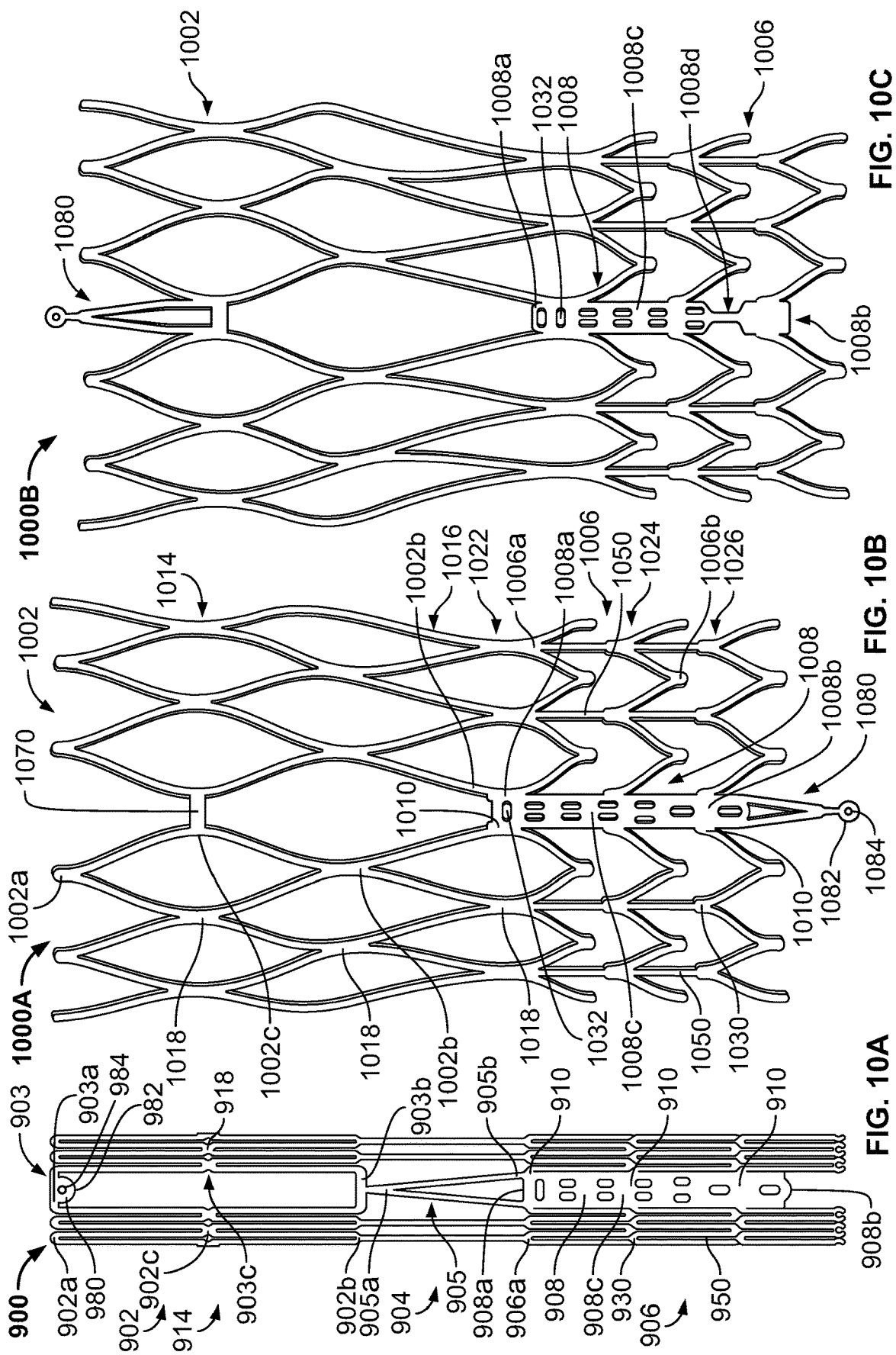

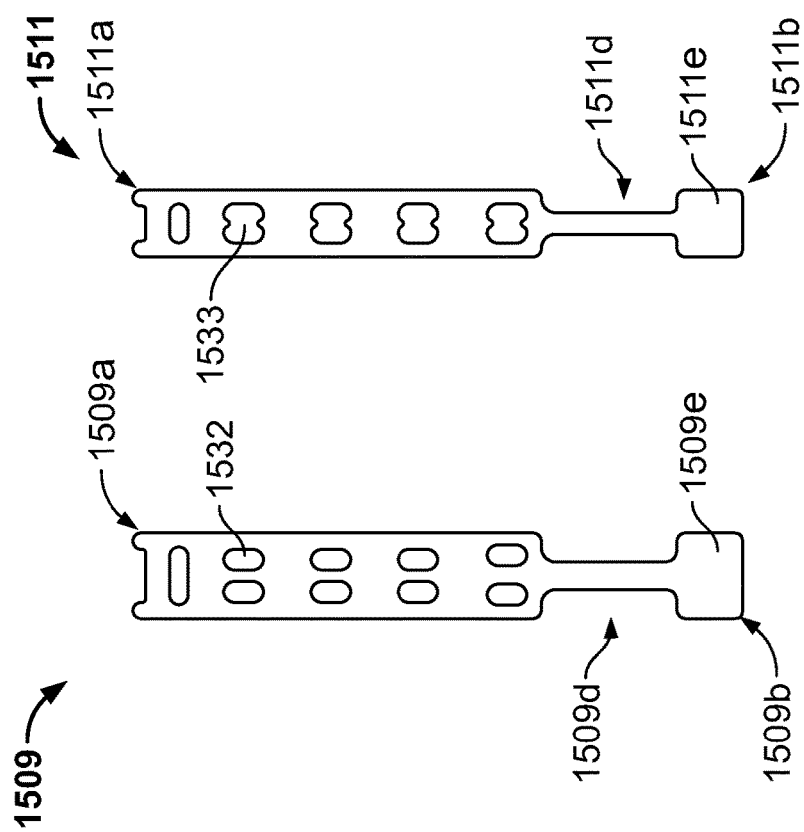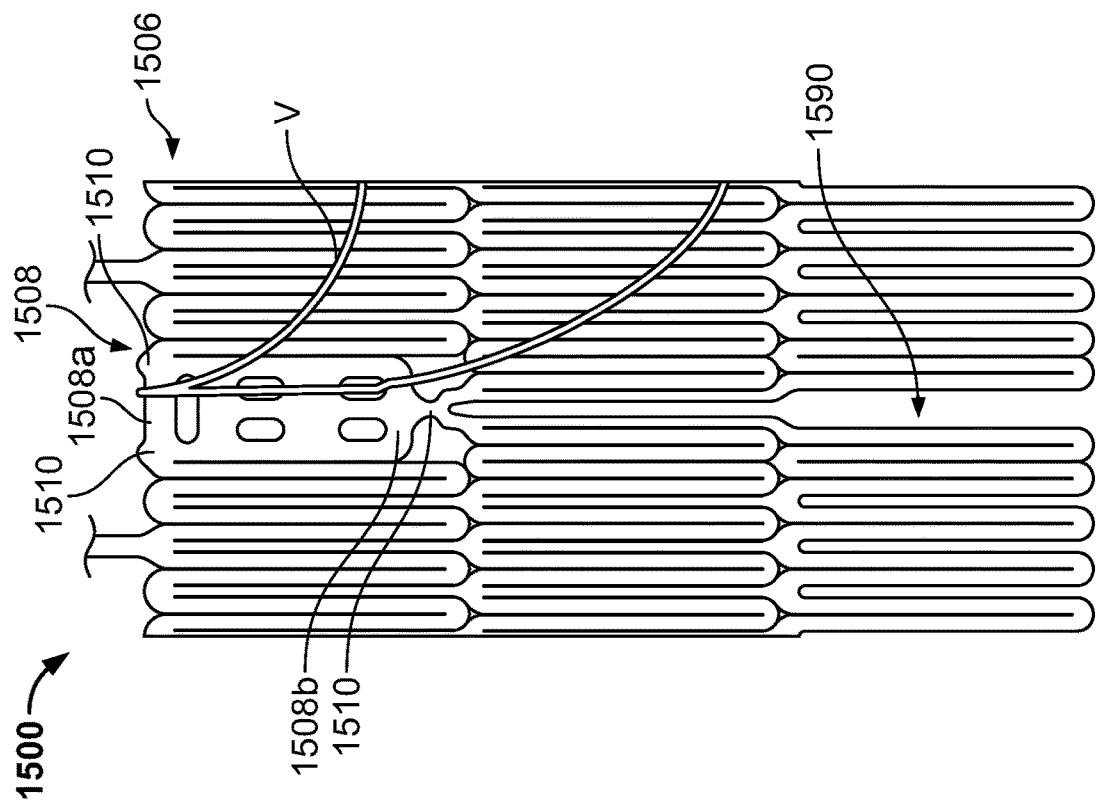

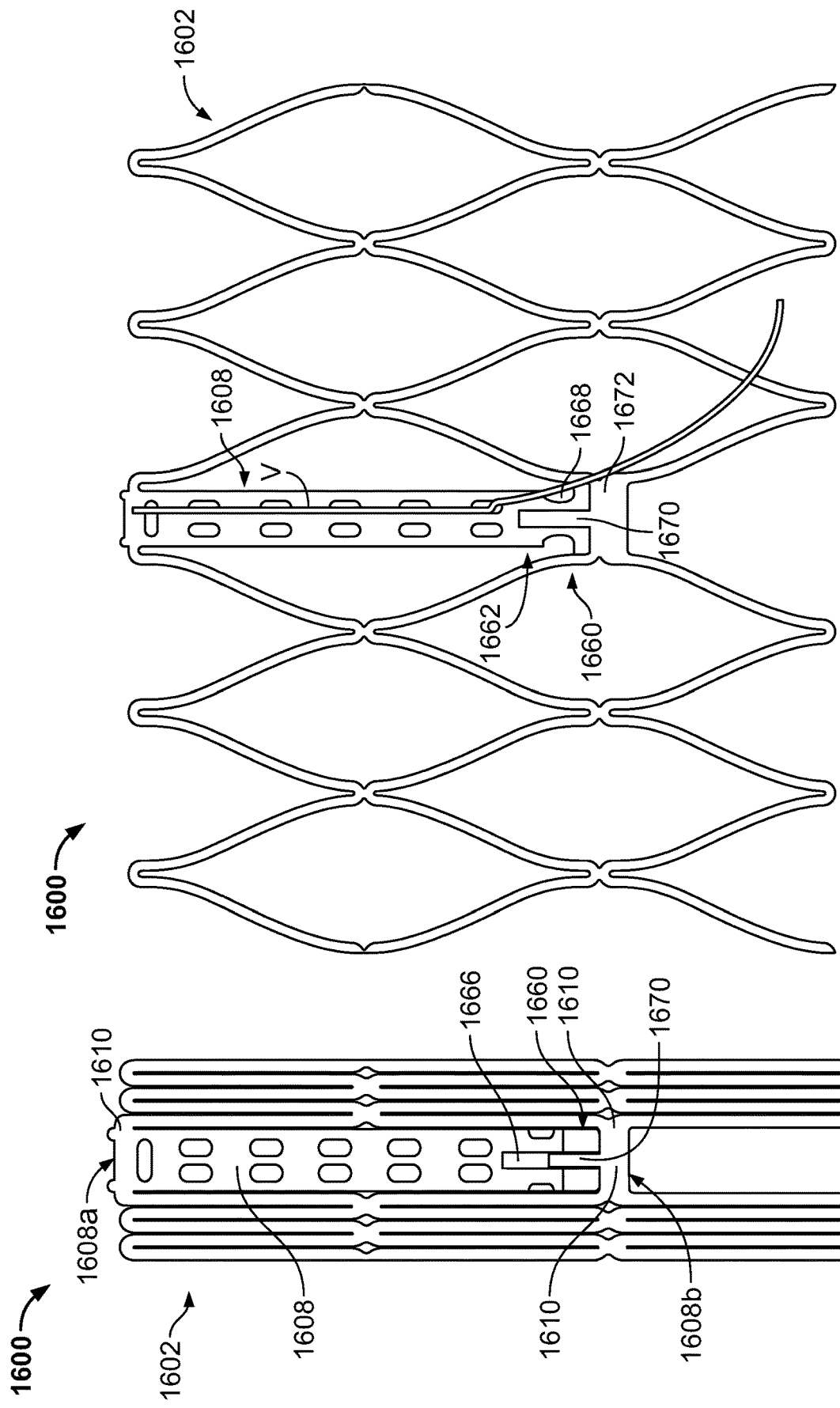

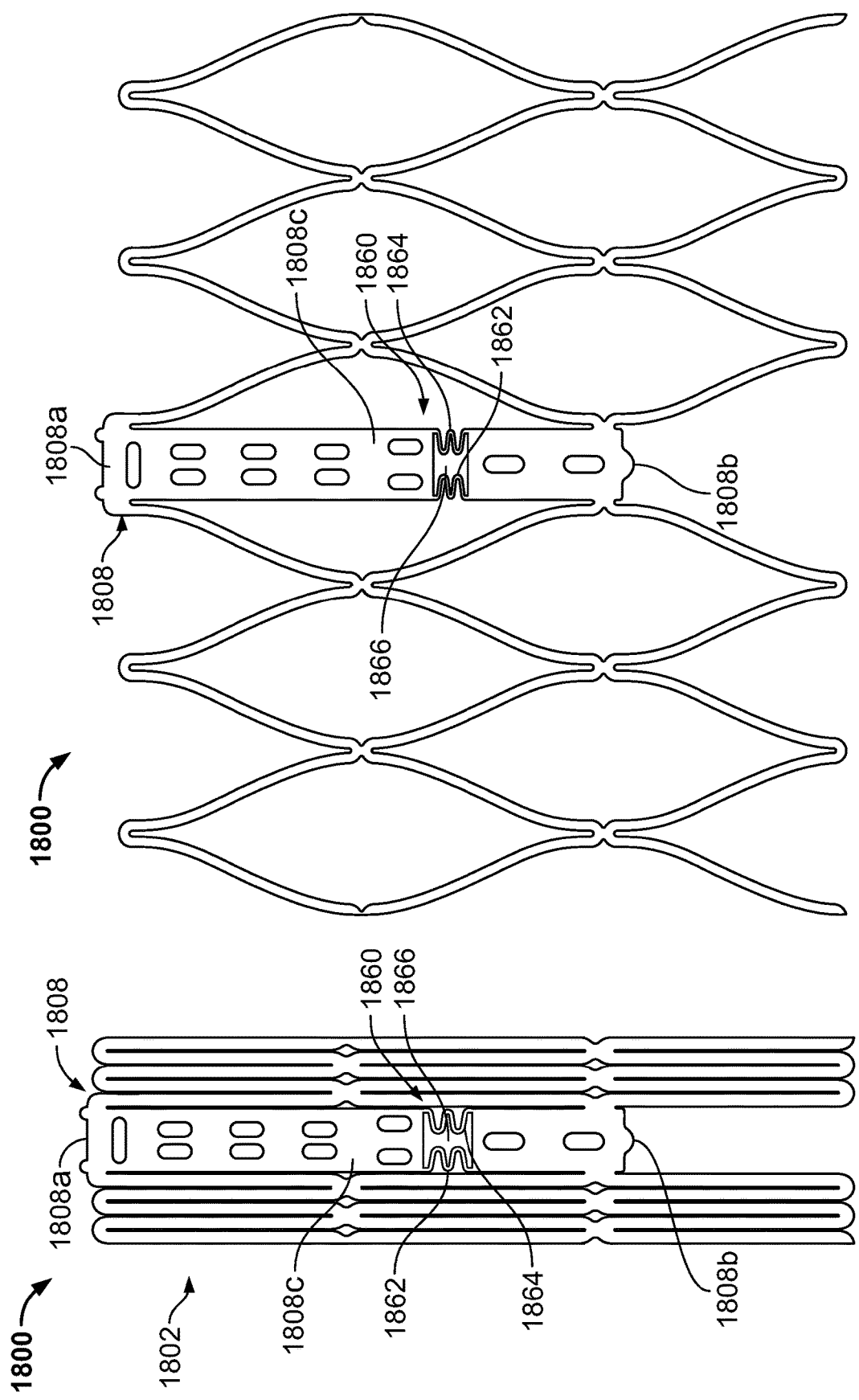

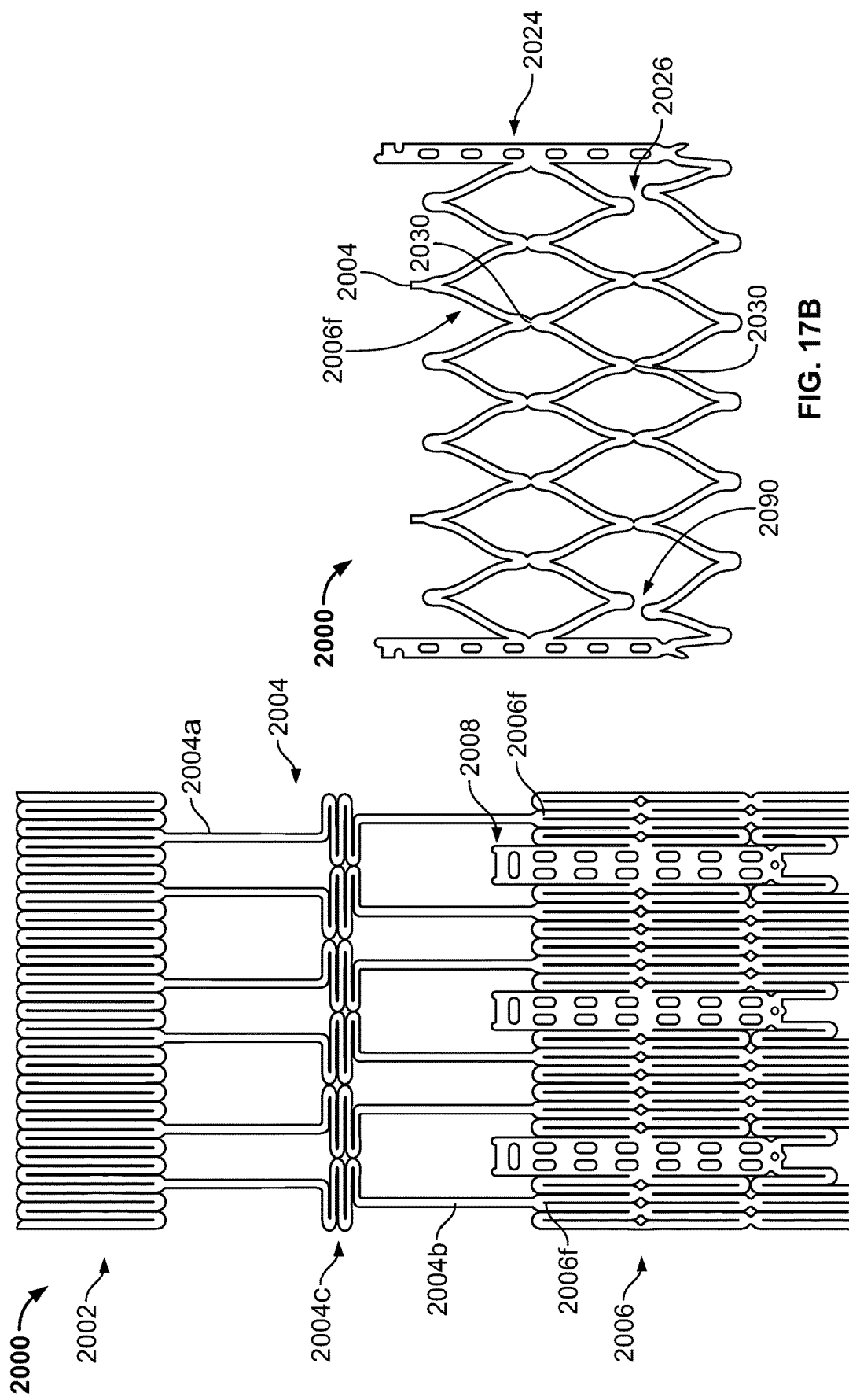

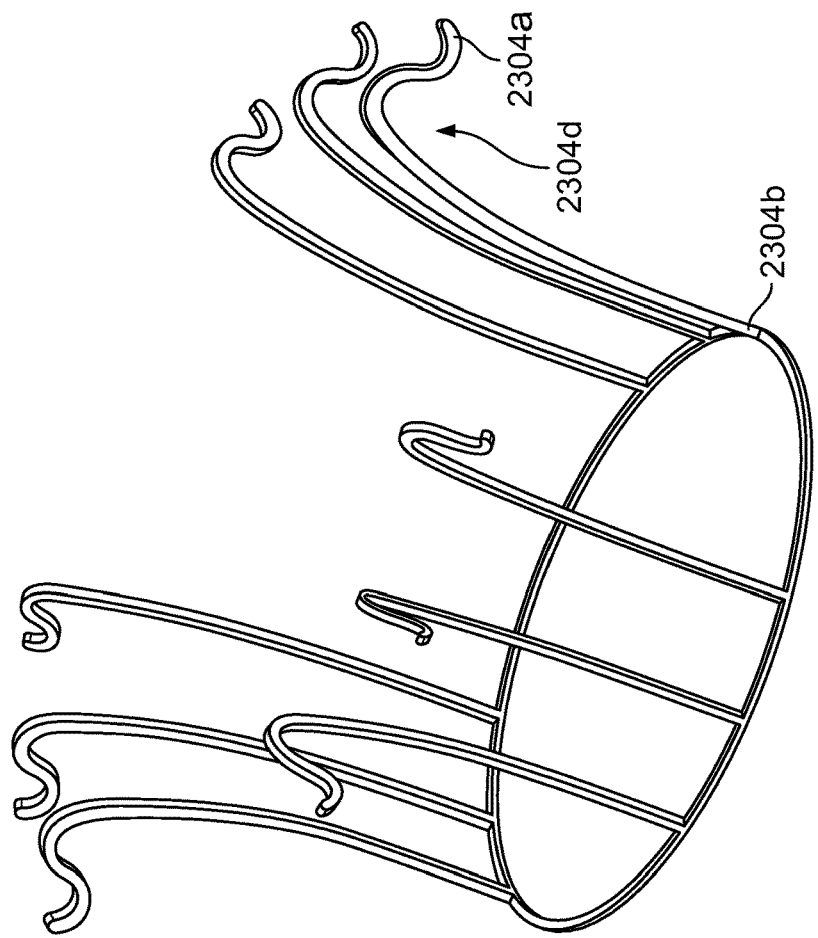
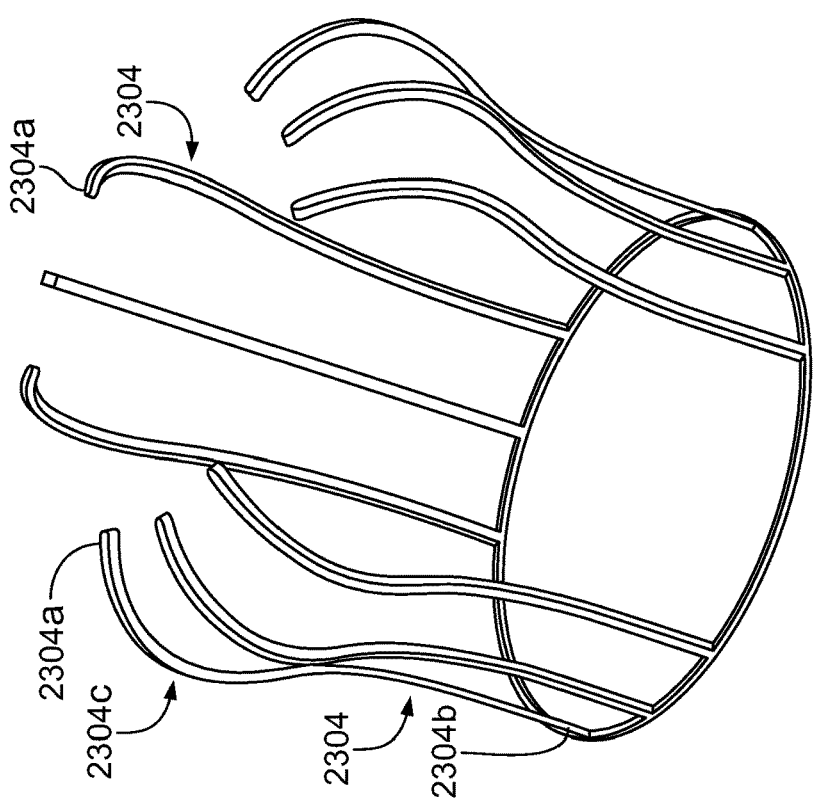
FIG. 23B
FIG. 23A

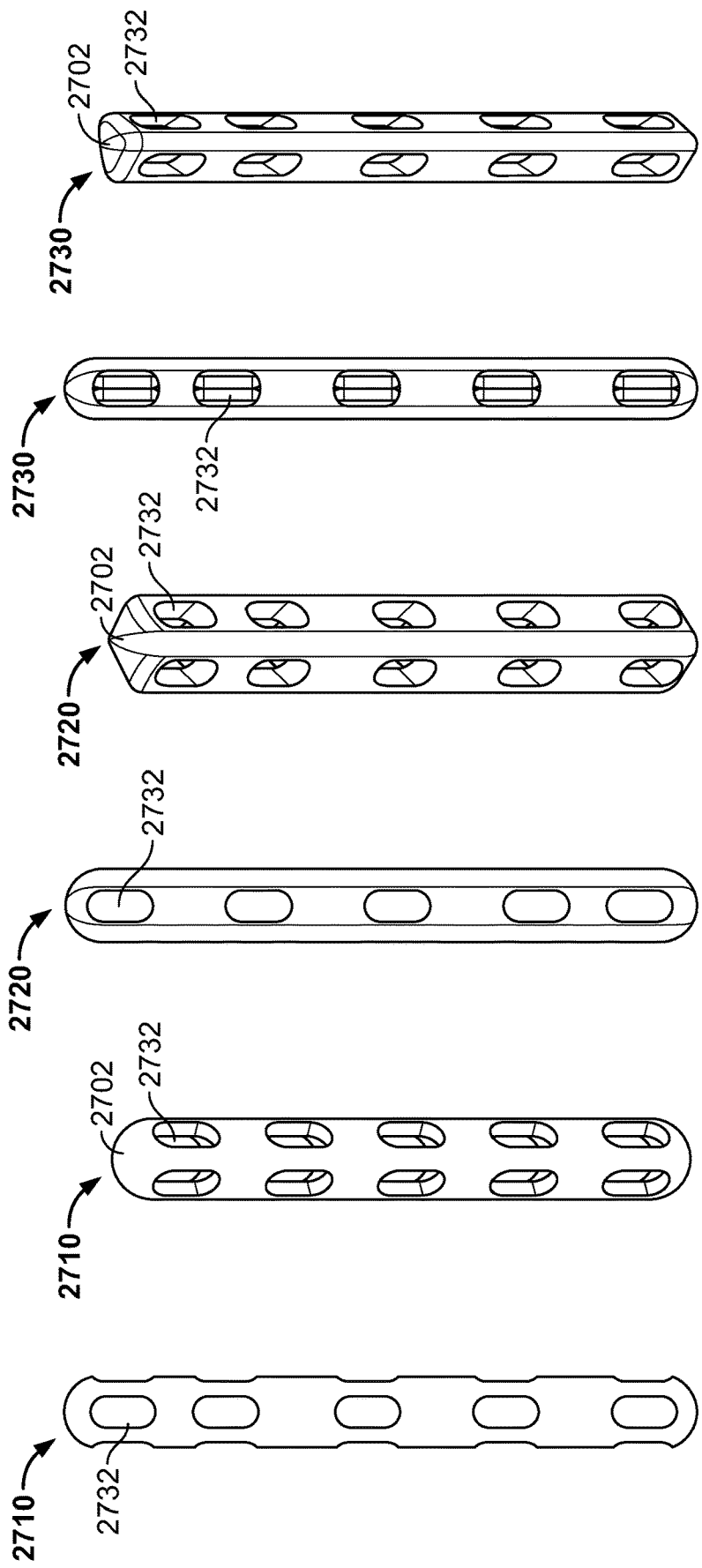

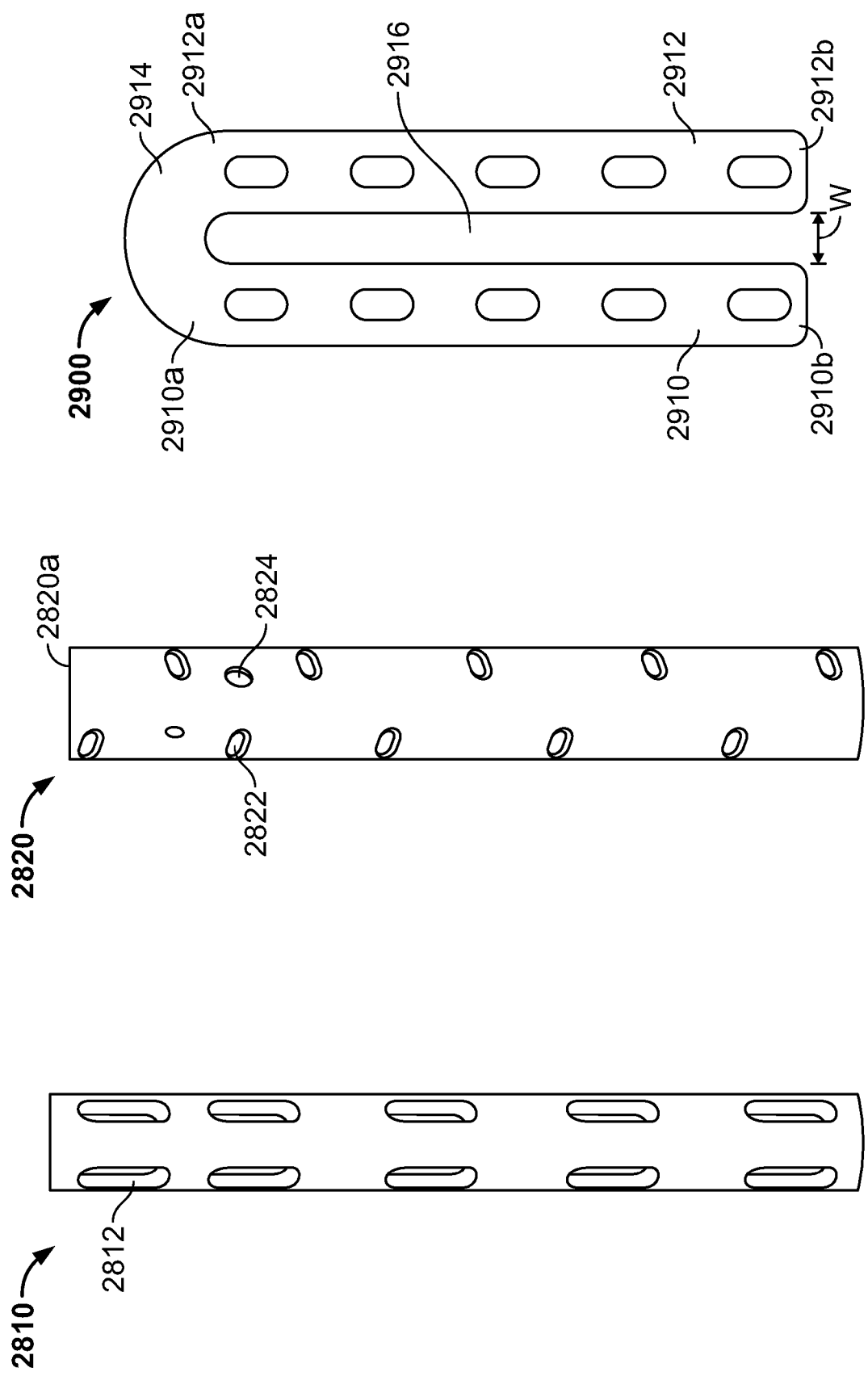

STENT FEATURES FOR COLLAPSIBLE PROSTHETIC HEART VALVES

The present application is a continuation of U.S. patent application Ser. No. 15/868,031, filed Jan. 11, 2018, which is a continuation of U.S. patent application Ser. No. 15/181,708, filed Jun. 14, 2016, now U.S. Pat. No. 9,901,447, which is a continuation of U.S. patent application Ser. No. 14/304,293, filed on Jun. 13, 2014, now U.S. Pat. No. 9,387,072, which is a continuation of U.S. patent application Ser. No. 13/203,627, filed on Dec. 7, 2011, now U.S. Pat. No. 8,808,366, which is a national phase entry under 35 U.S.C. § 371 of International Application No. PCT/US2010/000561, filed Feb. 25, 2010, published in English, which claims the benefit of the filing date of U.S. Provisional Patent Application No. 61/208,834, filed Feb. 27, 2009, the disclosures of which are hereby incorporated herein by reference.

BACKGROUND OF THE INVENTION

The present disclosure relates to prosthetic heart valves and, more specifically, to prosthetic heart valves having a collapsible stent frame.

Current collapsible prosthetic heart valve designs are for use within high-risk patients who may need a cardiac valve replacement, but who are not appropriate candidates for conventional open-chest, open-heart surgery. To address this problem, collapsible and re-expandable prosthetic heart valves have been developed that can be implanted transapically or percutaneously through the arterial system. However, such collapsible valves may have important clinical issues because of the nature of the patient's native stenotic leaflets that may not be resected as with the standard surgical practice of today. Additionally, patients with uneven calcification, bicuspid disease, and/or aortic insufficiency may not be treated well with the current collapsible prosthetic valve designs. The limitation of relying on evenly calcified leaflets has several issues, such as: (1) perivalvular leakage (PV leak), (2) valve migration, (3) mitral valve impingement, (4) conduction system disruption, etc., all of which can have adverse clinical outcomes. To reduce these adverse events, the optimal valve would seal and anchor to the cardiac tissue adequately without the need for excessive radial force that could harm nearby anatomy and physiology. An optimal solution may be to employ a stent that exerts a radial outward force just large enough to hold open the native stenotic/insufficient leaflets, and to use additional anchoring features more reliant on another anchoring methodology while reducing leaflet/stent stresses.

After multiple clinical valve failures during the late 1960's and early 1970's, a series of investigations on leaflet failure (e.g., dehiscence at the commissures) and stent post flexibility began and continue to be explored today. (Reis, R. L., et al., "The Flexible Stent: A New Concept in the Fabrication of Tissue Heart Valve Prostheses", *The Journal of Thoracic and Cardiovascular Surgery,* 683-689, 1971.) In-vitro, animal, and clinical investigations showed that "a flexible stent greatly reduces stress on the valve," which was as large as a 90% reduction of the closing stresses near the commissures when flexibility and coaptation area were maximized.

In more recent years, several groups have shown (e.g., via numerical computations) the importance of stent post flexibility during opening and closing phases to reduce leaflet stress and therefore tissue failure. (Christie, G. W., et al., "On Stress Reduction in Bioprosthetic Valve Leaflets by the Use of a Flexible Stent," *Journal of Cardiac Surgery*, Vol. 6, No. 4, 476-481, 1991; Krucinski, S., et al., "Numerical Simulation of Leaflet Flexure in Bioprosthetic Valves Mounted on Rigid and Expansile Stents," *Journal of Biomechanics*, Vol. 26, No. 8, 929-943, 1993.) In response to several rigid Ionescu-Shiley clinical valve failures in which the leaflets tore free at the commissures, Christie et al. (cited above) explored what would happen if a similar design was made with optimal flexibility. Stresses at the post tops were shown to be five times greater than at the belly of a leaflet. Thus, to optimize the design, the stent was made more flexible until the stresses in the leaflets were comparable to those in the leaflet belly. It was shown that a 0.2-0.3 mm deflection was all that was needed to make a significant reduction in stress, but that a deflection of approximately 1.1 mm would reduce the stress by up to 80%. Furthermore, it was explained that deflection beyond 1.1 mm was not only difficult to achieve with the available material and design, but did not result in additional stress reduction.

Krucinski et al. (also cited above) have shown that a 10% expansion (as may be the case during the opening phase of a Nitinol stent) may reduce sharp flexural stresses by up to 40% (e.g., "hooking"). This is likely due to the stent functioning in harmony with the patient's aortic root, or in other words, the commissures of the native valve moving outward during systole.

Although the above analyses and data may not be directly applicable to the collapsible valve designs detailed later in this specification, the basic understanding and theory about how pericardial tissue leaflets interact with a stent design as it functions are important to incorporate into any design where durability is paramount. It is possible that with good engineering design of the post and leaflet attachment, commissural dehiscence will not be a primary failure mechanism.

BRIEF SUMMARY OF THE INVENTION

The present disclosure relates to prosthetic heart valves. In one embodiment, a prosthetic heart valve includes a stent having a proximal end, a distal end, an expanded condition and a collapsed condition. The stent includes a plurality of distal cells at the distal end, a plurality of proximal cells at the proximal end, a plurality of support struts coupling the proximal cells to the distal cells, and at least one support post connected to a multiplicity of the proximal cells. The proximal cells are longitudinally spaced apart from the distal cells. A valve structure is connected to the at least one support post.

In another embodiment, a prosthetic heart valve includes a stent having a proximal end, a distal end, an expanded condition and a collapsed condition. The stent includes a plurality of distal cells at the distal end, a plurality of proximal cells at the proximal end, and at least one support post connected to a multiplicity of proximal cells. At least a portion of the proximal cells are directly connected to the distal cells. A valve structure is connected to the at least one support post.

In a further embodiment, a prosthetic heart valve includes a stent having a proximal end, a distal end, an expanded condition and a collapsed condition. The stent includes a plurality of cells at the proximal end, a plurality of support struts at the distal end, and at least one support post connected to a multiplicity of the cells. Each support strut has a first end connected to one of the cells and a free end. A valve structure is connected to the at least one support post.

In yet another embodiment, a prosthetic heart valve includes a stent having a proximal end, a distal end, an expanded condition and a collapsed condition. The stent includes a plurality of cells, at least one support post connected to a multiplicity of the cells, and a reinforcement secured to the at least one support post. A valve structure is connected to the at least one support post, the reinforcement being adapted to secure leaflets of the valve.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 6A is a developed view of a stent in an unexpanded condition with a plurality of posts each connected to cells at three locations;

FIG. 6B is a developed view of the stent of FIG. 6A in an expanded condition;

FIG. 8A is a developed view of a stent in an unexpanded condition and including a plurality of posts and a plurality of spacers interconnecting certain cells;

FIG. 8B is a front elevational view of the stent of FIG. 8A in an expanded condition;

FIG. 10A is a partial developed view of a stent in an unexpanded condition and including a plurality of substantially rigid posts and an interlocking feature;

FIG. 10B is a partial front elevational view of a stent in an expanded condition and including a plurality of substantially rigid posts and an interlocking feature;

FIG. 10C is a partial front elevational view of a stent in an expanded condition and including a plurality of substantially rigid posts and an interlocking feature;

FIG. 12A is a partial developed view of a stent in an unexpanded condition and including at least one shortened post;

FIG. 12B is an enlarged view of an alternate post for incorporation into the stent of FIG. 12A;

FIG. 12C is an enlarged view of an alternate post for incorporation into the stent of FIG. 12A;

FIG. 13A is a partial developed view of a stent in an unexpanded condition and including a post with a slidable portion;

FIG. 13B is a partial developed view of the stent of FIG. 13A in an expanded condition;

FIG. 15A is a partial developed view of a stent in an unexpanded condition with an elongated support post having a collapsible post feature;

FIG. 15B is a partial developed view of the stent of FIG. 15A in an expanded condition;

FIG. 17A is a developed view of a stent in an unexpanded condition with support struts connected to a proximal cell spaced from the elongated support post;

FIG. 17B is a developed view of a proximal portion of the stent of FIG. 17A;

FIG. 23A is a partial perspective view of an embodiment of the stent of FIG. 22 in an expanded condition with support struts having C-shaped distal portions;

FIG. 23B is a partial perspective view of an embodiment of the stent of FIG. 22 in an expanded condition with support struts having hook-shaped distal portions;

FIG. 28A is a side elevational view of a secondary post with a substantially circular cross-section;

FIG. 28B is a perspective view of the secondary post of FIG. 28A;

FIG. 28C is a side elevational view of a secondary post with a substantially rectangular cross-section;

FIG. 28D is a perspective view of the secondary post of FIG. 28C;

FIG. 28E is a side elevational view of a secondary post with a substantially triangular cross-section;

FIG. 28F is a perspective view of the secondary post of FIG. 28E;

FIG. 29A is a side elevational view of a secondary post with a hollow core;

FIG. 29B is a side elevational view of a secondary post with a hollow core and two different kinds of eyelets;

FIG. 30 is a side elevational view of a reinforcement for a stent including two columns connected by an arch;

DETAILED DESCRIPTION

As used herein, the term "proximal" refers to the end of a stent closest to the heart when placing the stent in a patient, whereas the term "distal" refers to the end of the stent farthest from the heart when placing the stent in a patient.

Figure 1:
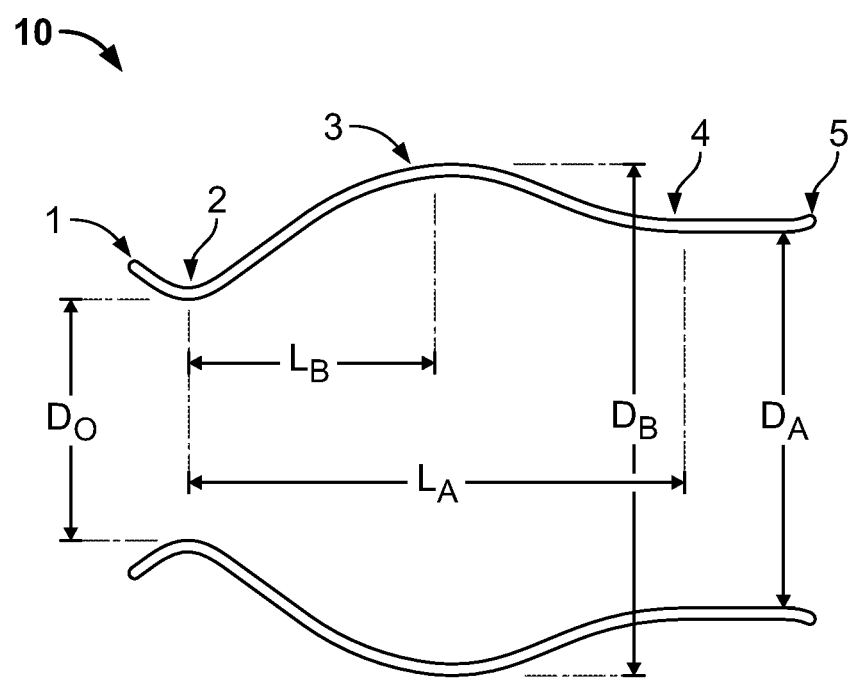
FIG. 1 is a schematic longitudinal cross-section of an aortic root.

FIG. 1 illustrates the anatomy of an aortic root 10 to aid in the understanding of how the stent/valve interacts with the aortic root. (FIG. 1 is from Reul, H., et al., "The geometry of the aortic root in health, at valve disease and after valve replacement," *Journal of Biomechanics*, Vol. 23, No. 2, 181-91, 1990). The aortic root is the part of the aorta attached to the heart. The aorta is the largest artery in the body, which extends from the left ventricle of the heart down to the abdomen, where it branches off into two smaller arteries. The aorta supplies oxygenated blood to all parts of the body. The aortic root contains the aortic valve and gives rise to the coronary arteries, which are the arteries that supply blood to the heart muscle. As shown in FIG. 1, the aortic root 10 has several features, namely: a left ventricular outflow tract (LVOT) 1; an annulus 2; a sinus 3; sinotubular junction (STJ) 4; and an ascending aorta 5. FIG. 1 further depicts several geometrical parameters of aortic root 10, to wit: $D_O$=orifice diameter; $D_A$=aortic diameter distal to the sinus 3; $D_B$=maximum projected sinus diameter; $L_A$=length of the sinus 3; and $L_B$=distance between $D_O$ and $D_B$.

Flexibility of Stent Via Post Connections

Figure 2:
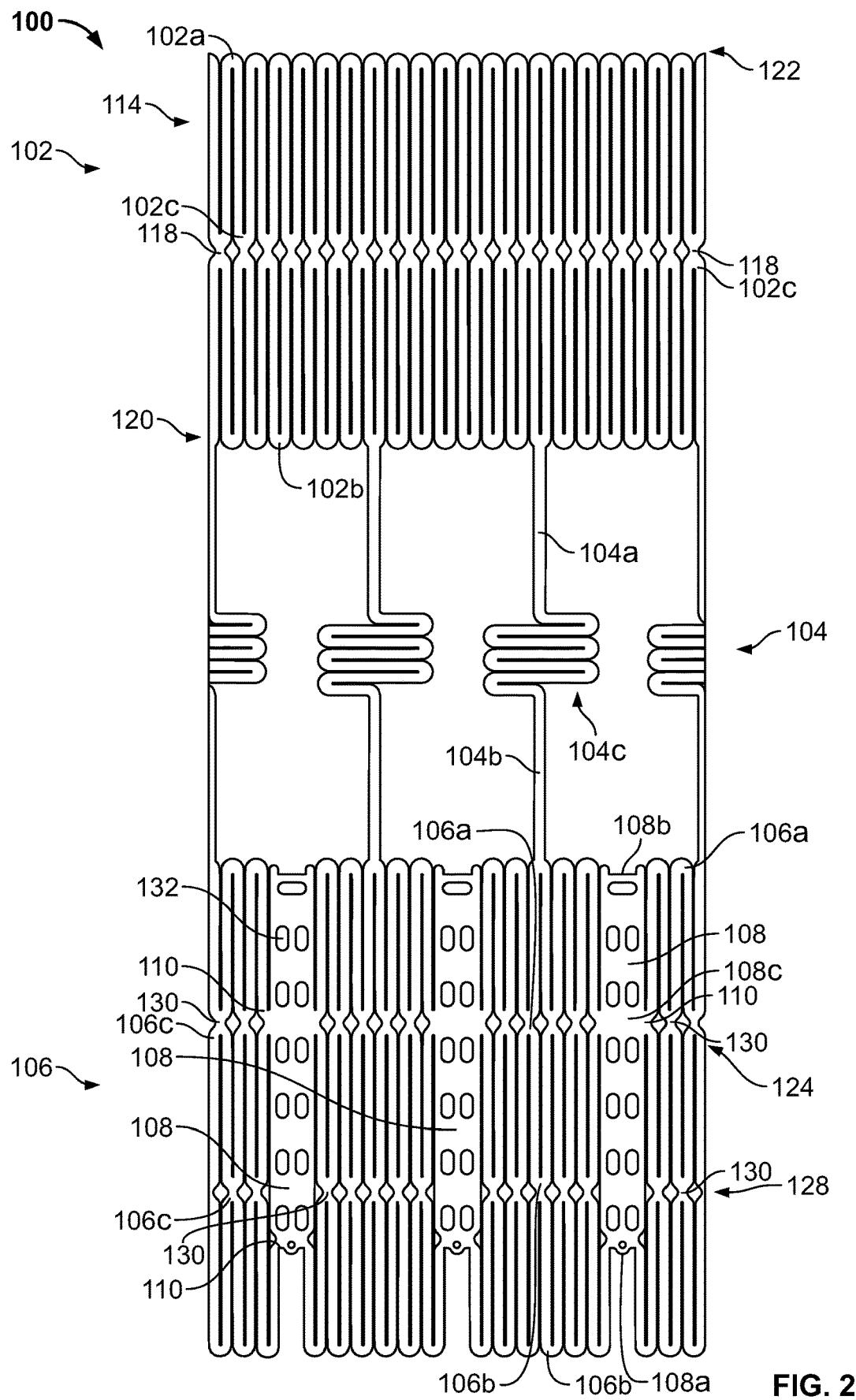
FIG. 2 is a developed view of a stent with a plurality of posts each connected to cells at two locations.

In all the embodiments disclosed herein, the stents are part of a prosthetic heart valve. The stents have an expanded condition and a collapsed condition. In the expanded condition, at least a portion of the stent may have a substantially cylindrical shape. FIG. 2 depicts a developed view of stent 100 in an unexpanded condition, i.e., in a flat, rolled out condition as seen when laser cut from a tube. Stent 100 generally includes one or more rows of distal cells 102, at least one support strut 104, one or more rows of proximal cells 106, at least one elongated support post 108, and at least one post connection 110 coupling a support post 108 to at least some of the proximal cells 106. One or more support struts 104 connect distal cells 102 to proximal cells 106. In some embodiments, three support struts 104 may interconnect proximal cells 106 and distal cells 102. Stent 100 may nonetheless include more or fewer support struts 104. Regardless of the specific number of support struts 104, support struts 104 longitudinally separate proximal cells 106 from distal cells 102 and, therefore, proximal cells 106 are located proximally relative to distal cells 102.

Stent 100 or any other embodiment disclosed herein may be wholly or partly formed of any biocompatible material, such as metals, synthetic polymers, or biopolymers capable of functioning as a stent. Suitable biopolymers include, but are not limited to, collagen, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, and polyaramides. For example, stent 100 may be made of polyetheretherketone (PEEK).

Distal cells 102 are adapted to be positioned distally relative to sinus 3 to anchor at or near the ascending aorta 5 and sinotubular junction 4. In certain embodiments, distal cells 102 may be arranged in longitudinal rows. In the embodiment shown in FIG. 2, stent 100 includes a single row 114 of distal cells 102. The row 114 of distal cells 102 may be oriented substantially perpendicular to support struts 104. While FIG. 1 shows a single row 114 of distal cells 102, stent 100 may include multiple rows of distal cells 102.

Each distal cell 102 has a distal end 102a, a proximal end 102b, and a middle portion 102c between the distal end 102a and the proximal end 102*b*. A cell connection 118 couples two adjacent distal cells 102. As seen in FIG. 2, each cell connection 118 is positioned at a middle portion 102*c* of a distal cell 102. Aside from the two adjacent distal cells 102, cell connection 118 is not coupled to any other distal cell 102.

All distal cells 102 collectively have a first end portion 120 and a second end portion 122. In the embodiment shown in FIG. 2, first end portion 120 is aligned with the proximal ends 102*b* of the distal cells 102, while the second end portion 122 is aligned with the distal ends 102*a* of the distal cells 102. Distal cells 102 are connected to support struts 104 at the first end portion 120. In some embodiments, support struts 104 are coupled to the proximal ends 102*b* of some distal cells 102.

Support struts 104 interconnect distal cells 102 and proximal cells 106. As discussed above, stent 100 may include one or more support struts 104. As depicted in FIG. 2, stent 100 may include one support strut 104 for every five proximal cells 106. Stent 100 may also include one support strut 104 for every seven distal cells 102. However, these ratios are not critical, and will depend on the size of proximal cells 106 and distal cells 102, the desired stiffness of stent 100 and other considerations.

Each support strut 104 has a first end portion 104*a*, a second end portion 104*b*, and a middle portion 104*c* located between the first and second end portions. The first end portion 104*a* of each support strut 104 is connected to the proximal end 102*b* of a distal cell 102. The second end portion 104*b* of each support strut 104 is connected to the distal end 106*a* of a proximal cell 106. Thus, a single support strut 104 may couple a single distal cell 102 to a single proximal cell 106.

As shown in FIG. 2, the first and second end portions 104*a*, 104*b* of each support strut 104 may have straight or linear configurations, while the middle portion 104*c* may have a non-linear configuration. In the embodiment depicted in FIG. 2, the middle portion 104*c* of each support strut 104 has a sinusoidal or wave shape, but middle portions 102*c* of one or more support struts 104 may have other non-linear configurations. First and second end portions 104*a*, 104*b* of support struts 104 may be oriented substantially parallel to each other, and may be either longitudinally aligned or not aligned with each other. For example, first and second end portions 104*a*, 104*b* of support struts 104 may be longitudinally aligned with each other, as seen in FIG. 2. Alternatively, portions 104*a* and 104*b* may be laterally offset from each other, for instance, with portion 104*b* connected to the distal end 106*a* of a next adjacent proximal cell 106 to the left or right of the connection depicted in FIG. 2.

As discussed above, at least one support strut 104 is connected to one proximal cell 106. Each proximal cell 106 has a distal end 106*a*, a proximal end 106*b* and a middle portion 106*c* between the distal end 106*a* and the proximal end 106*b*. Together, proximal cells 106 are configured to impart radial force against the leaflets of a heart valve. Proximal cells 106 may be arranged in longitudinal rows. For example, stent 100 may include a first row 124 of proximal cells 106 positioned distally of a second row 128 of proximal cells 106. At least one support strut 104 is connected to a proximal cell 106 located in the first row 124.

A cell connection 130 couples two adjacent proximal cells 106 positioned in the same row. The proximal cells 106 in the first row 124 are joined to the proximal cells 106 in the second row 128 by sharing one or more common cell legs.

The cells in the first row 124 and the cells in the second row 128 may not form continuous chains of cells. That is, the chain of cells forming the first row 124 and the chain of cells forming the second row 128 may each be disrupted by one or more elongated support posts 108. Support posts 108 are intended to support the commissures along which the valve leaflets are joined to one another. In this embodiment, as in all of the embodiments described herein, the stent typically has three such support posts 108, one for supporting each of the commissures of the aortic valve. However, where the stent is intended for use in a prosthetic valve other than an aortic valve, the stent may include a greater or lesser number of support posts.

Stent 100 may include sets of proximal cells 106 between elongated support posts 108. For example, as shown in FIG. 2, stent 100 may include an elongated support post 108 between two sets of five proximal cells 106 in first row 124. However, the number of cells between support posts 108 will depend on the size of proximal cells 106, the number of cell rows and other such considerations. Support posts 108 may extend longitudinally adjacent first cell row 124, second cell row 128 or both cell rows. Similarly, support posts 108 may be connected to proximal cells in first cell row 124, second cell row 128 or both cell rows.

Stent 100 may include one support strut 104 for every set of proximal cells 106 located between two elongated support posts 108. For instance, stent 100 may have one support strut 104 for every set of five proximal cells 106 located between two elongated support posts 108. In this embodiment, the second end portion 104*b* of each support strut 104 is connected to the proximal cell 106 located midway between two elongated support posts 108. Support strut 104 is not connected to a proximal cell 106 located adjacent to an elongated support post 108.

The support posts 108 may be connected to one or more proximal cells 106 via post connections 110. Each elongated support post 108 has a proximal end 108*a*, a distal end 108*b*, and a middle 108*c*. A plurality of eyelets or apertures 132 are formed in each support post 108 and used for suturing the valve leaflets to stent 100. As seen in FIG. 2, apertures 132 may have different sizes, shapes and positions.

In the embodiment depicted in FIG. 2, post connections 110 are located at or near the middle 108*c* of elongated support post 108 to allow for post flexibility during valve cycling, thereby reducing dynamic loading and the resulting in-leaflet stress. Specifically, the middle portions 106*c* of two proximal cells 106 located in the first row 124 are attached to opposite sides of the middle portion 108*c* of each elongated support post 108. Two proximal cells 106 arranged in the second row 128 are attached near their middle portions 106*c* to opposite sides of the proximal end 108*a* of each elongate support post 108. Although FIG. 2 shows post connections 110 at very specific locations, stent 100 may include post connections 110 at other locations.

In operation, a user may place a stent 100 (or any other stent disclosed herein) using any conventional methods. For instance, the user may first place stent 100 in a crimped condition and then insert it into a delivery instrument or system. The delivery instrument may be advanced through the patient's vasculature or through a transapical procedure until stent 100 reaches the desired destination near the aortic valve. Subsequently, the user deploys and expands stent 100 at the target site. The structure of stent 100 described above provides very flexible support posts 108 which reduce the maximum amount of stress at the commissural interfaces on valve cycling. That is, since the distal ends of the support posts 108 are free from connections to the proximal cells 106, these ends can move freely like a cantilever beam.

Figure 3:
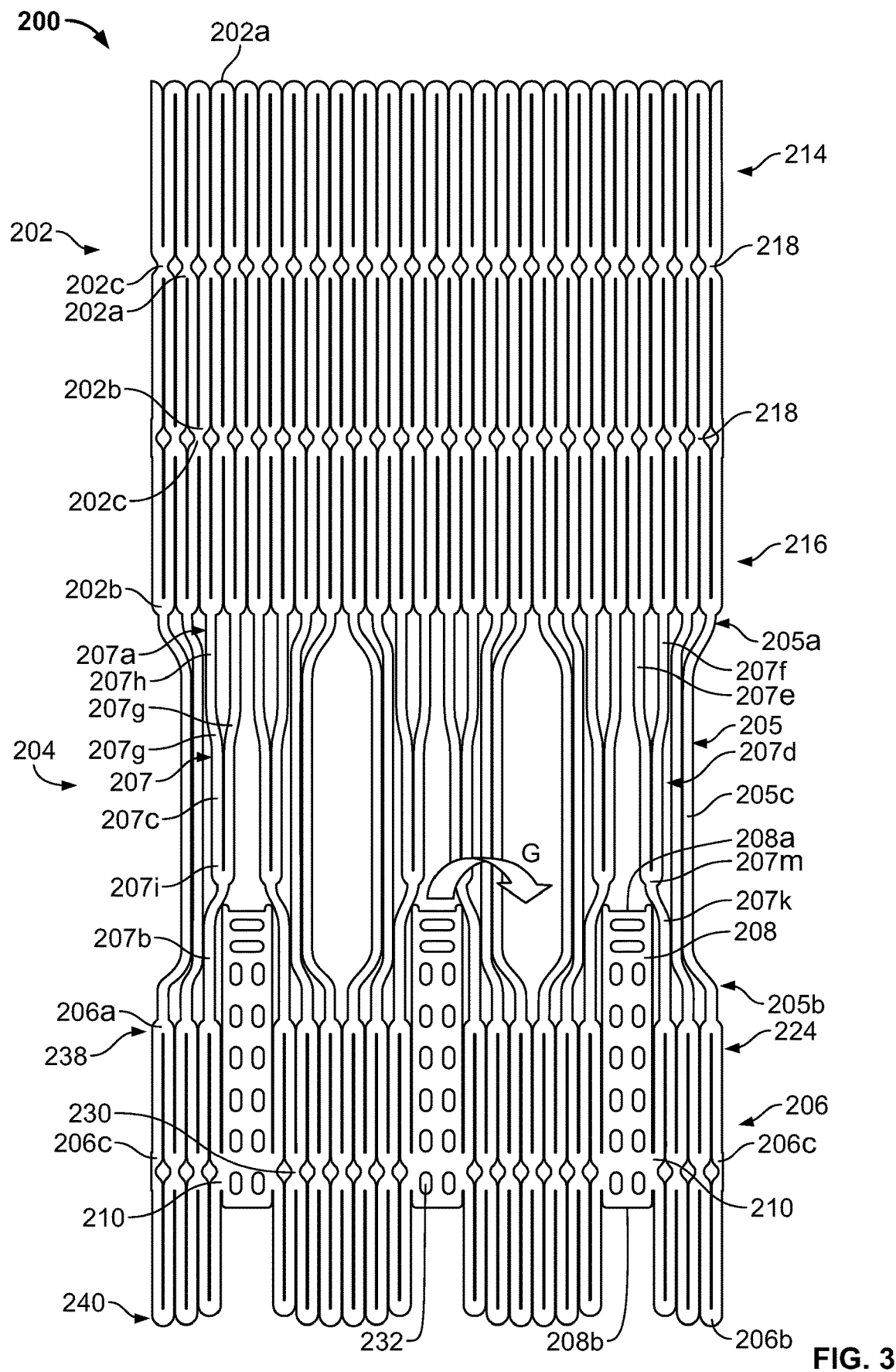
FIG. 3 is a developed view of a stent with a plurality of posts each connected to cells only at their proximal ends.

FIG. 3 shows another embodiment of a stent 200 with post connections 210 coupling proximal cells 206 to elongated support posts 208 at different locations than for stent 100. Stent 200 is similar to stent 100 and generally includes distal cells 202, proximal cells 206, and support strut arrays 204 interconnecting the distal cells 202 and the proximal cells 206. In some embodiments, stent 200 may include a first longitudinal row 214 of distal cells 202, a second longitudinal row 216 of distal cells 202, and a single longitudinal row 224 of proximal cells 206.

Each distal cell 202 has a distal end 202a, a proximal end 202b, and a middle portion 202c between the distal end 202a and the proximal end 202b. Cell connections 218 located at the middle portions 202c of the distal cells 202 in each row join two adjacent distal cells in that row together. The distal cells 202 in the first row 214 are joined to the distal cells 202 in the second row 216 by sharing one or more common cell legs.

The proximal ends 202b of every distal cell 202 located in the second row 216 may be connected to a support strut (205 or 207) of the support strut arrays 204. In the embodiment depicted in FIG. 3, stent 200 includes three support strut arrays 204 each connected to eight distal cells 202 and six proximal cells 206. Each support strut array 204 may alternatively be connected to more or fewer distal cells 202 and proximal cells 206. Regardless, each support strut array 204 includes one or more support struts (205 or 207) coupled to the proximal cells 206 adjacent to an elongated support post 208 to halt any significant distribution of the strains from post deflection to the remaining stent frame.

Each support strut array 204 may include two kinds of support struts, namely support struts 205 and support struts 207. In some embodiments, each support strut array 204 may include four support struts 205 and two support struts 207. Two support struts 207 may be positioned between two sets of two support struts 205. It is envisioned, however, that support strut arrays 204 may each include more or fewer support struts 205 and 207.

Each support strut 205 has a first end portion 205a, a second end portion 205b, and a middle portion 205c between the first and second end portions. First end portion 205a may be connected to a proximal end 202b of a distal cell 202 in the second row 216. Second end portion 205b may be connected to a distal end 206a of a proximal cell 206. Middle portion 205c has a straight or linear configuration and interconnects first and second end portions 205a, 205b. The first end portion 205a of each support strut 205 defines an oblique angle relative to middle portion 205c. This oblique angle may vary from one support strut 205 to another. The second end portion 205b of each support strut 205 may also define an oblique angle relative to middle portion 205c. This oblique angle may also vary from one support strut 205 to another.

Support struts 207 each have a first end portion 207a, a second end portion 207b, and a middle portion 207c between the first and second end portions. Each support strut 207 includes a bifurcated section 207d extending from the middle portion 207c to the first end portion 207a. Bifurcated section 207d of each support strut 207 includes two branches 207e, 207f. Branches 207e, 207f are oriented substantially parallel to each other, except in a transition or angled portion 207g of the bifurcated section 207d in which the branches define an oblique angle with respect to each other and to first and second portions 207h and 207i. Each branch 207e, 207f includes a first portion 207h, a second portion 207i, and the transition or angled portion 207g positioned between the first and second portions. In the first portion 207h of the bifurcated section 207d, branches 207e, 207f are positioned farther apart from each other than in the second portion 207i.

Each branch 207e, 207f is connected to the proximal end 202b of a distal cell 202 in the second row 216. Branches 207e, 207f of each bifurcated section 207d converge into a single support member 207k at converging point 207m. Each single support member 207k of support struts 207 may be connected to the distal end 206a of a single proximal cell 206 adjacent a support post 208.

As discussed above, each support strut array 204 is connected to the distal ends 206a of a plurality of proximal cells 206. Specifically, support struts 207 are connected to proximal cells 206 positioned adjacent a support post 208, while support struts 205 are connected to the proximal cells 206 which are not adjacent a support post 208.

Each proximal cell 206 has a distal end 206a, proximal end 206b and a middle portion 206c between the distal end 206a and the proximal end 206b. The proximal cells 206 collectively define a first end 238 closer to support strut arrays 204 and a second end 240 farther from support strut arrays 204. Proximal cells 206 are arranged in a single longitudinal row. Cell connections 230 located at middle portions 206c join adjacent proximal cells 206 together.

Some of the proximal cells 206 are connected to an elongated support post 208. As seen in FIG. 3, one or more elongated support posts 208 may extend beyond the first end 238 collectively defined by all the proximal cells 206 but may not extend past the second end 240. Stent 200 may have, for example, one elongated post 208 for every six proximal cells 206.

Each elongated support post 208 has a distal end 208a, a proximal end 208b and a plurality of eyelets or apertures 232 for suturing the valve leaflets to the stent 200. As shown in FIG. 3, apertures 232 may extend from distal end 208a to proximal end 208b and may have different shapes and sizes. In certain embodiments, apertures 232 may have substantially elliptical shapes.

Elongated support posts 208 are connected to proximal cells 206 by post connections 210. In the embodiment shown in FIG. 3, post connections 210 are located only at or near the proximal end 208b of elongated support post 208 for allowing the elongated support post to deflect inwardly in the direction indicated by arrow G under diastolic backpressure. Although FIG. 3 shows post connections 210 at precise positions near proximal ends 208b, post connections 210 may be positioned closer or farther from proximal ends 208b to allow for more or less post flexibility. Each elongated support post 208 may be connected to proximal cells 206 through two post connections 210 located on opposite sides of the elongated support post.

Figure 4:
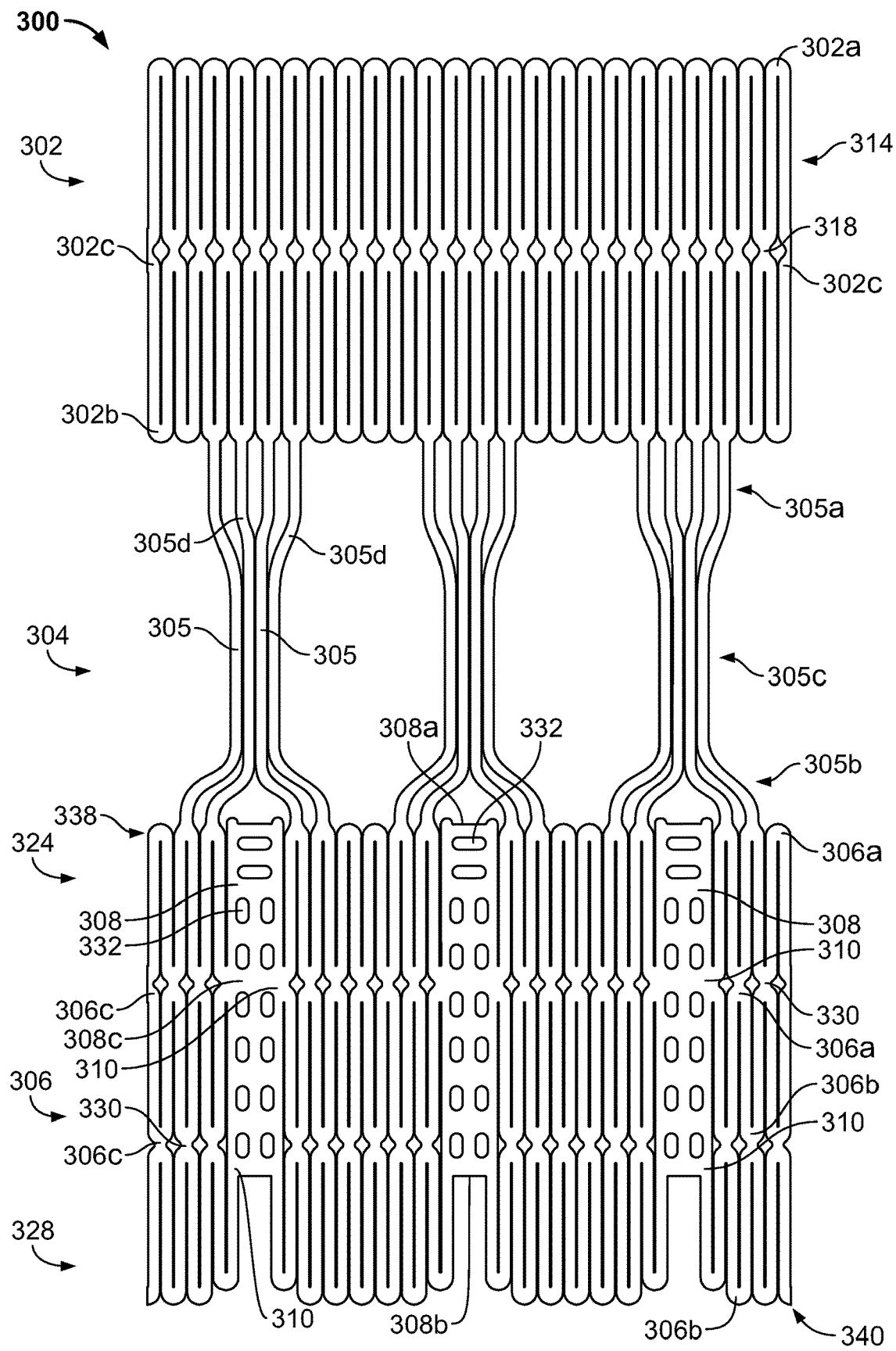
FIG. 4 is a developed view of a stent with a plurality of posts each connected to cells at their proximal ends and middle portions.

FIG. 4 shows a stent 300 including distal cells 302, proximal cells 306, support strut arrays 304, elongated support posts 308 and post connections 310 at two locations along each elongated support post 308. The positions of post connections 310 reduce post flexibility and the strains experienced in post connections 310 as compared to the post connections 210 in stent 200.

In the embodiment depicted in FIG. 4, stent 300 includes a single row 314 of distal cells 302. Each distal cell 302 has a distal end 302a, a proximal end 302b and a middle portion 302c between the proximal end 302b and the distal end 302a. Cell connections 318 join adjacent distal cells 302 at their middle portions 302c.

Stent 300 may include one support strut array 304 for every eight distal cells 302. Each support strut array 304 may include four support struts 305 joined to four distal cells 302. Each support strut array 304 may nonetheless include more or fewer support struts 305. In either event, support strut arrays 304 interconnect distal cells 302 and proximal cells 306.

Each support strut 305 has a first end portion 305a, a second end portion 305b, and a middle portion 305c located between the first and second end portions. The first end portion 305a of each support strut 305 is connected to the proximal end 302b of at least one distal cell 302, whereas the second end portion 305b of each support strut 305 is connected to the distal end 306a of at least one proximal cell 306.

The middle portion 305c of each support strut 305 has a transition section 305d connected to the first end portion 305a. Transition section 305d is oriented at an oblique angle relative to the middle portion 305c. The middle portions 305c of support struts 305 are oriented substantially parallel to each other except at the transition sections 305d. The first end portions 305a of support struts 305 are also oriented substantially parallel to each other.

The second end portion 305b of each support strut 305 is connected to the distal end 306a of at least one proximal cell 306. Each second end portion 305b has a substantially curved configuration or profile. In some embodiments, each support strut array 304 may include four support struts 305 connected to the two proximal cells 306 adjacent to an elongated support post 308 and to the two next adjacent proximal cells. That is, two support struts 305 may be connected to a proximal cell 306 adjacent to one side of elongated support post 308 and to the next adjacent proximal cell, respectively, while another two support struts 305 may be connected to a proximal cell 306 adjacent to the opposite side of the same elongated support post 308 and to the next adjacent proximal cell, respectively.

Proximal cells 306 each have a distal end 306a, a proximal end 306b and a middle portion 306c between the distal end 306a and the proximal end 306b. Stent 300 may include a first row 324 of proximal cells 306 and a second row 328 of proximal cells 306. First row 324 and second row 326 of proximal cells 306 are oriented substantially parallel to each other. First row 324 is located distally relative to second row 328. All of the proximal cells 306 collectively define a first end 338 closer to the support strut arrays 304 and a second end 340 farther from support strut arrays 304. The first end 338 of all the proximal cells 306 is defined by the distal ends 306a of the proximal cells located in first row 324, whereas the second end 340 is defined by the proximal ends 306b of the proximal cells 306 located in the second row 328.

A cell connection 330 joins the middle portions 306c of adjacent proximal cells 306 in the first row 324. Other cell connections 330 join the middle portions 306c of adjacent proximal cells 306 in the second row 328. The proximal cells 306 in the first row 324 are joined to the proximal cells in the second row 328 by sharing one or more common cell legs.

Elongated support posts 308 are connected to some proximal cells 306 by post connections 310. In the embodiment depicted in FIG. 4, each elongated support post 308 traverses the longitudinal length of the proximal cells 306 in the first row 324 and at least a portion of the length of the proximal cells 306 in the second row 328. Each elongated support post 308 has a distal end 308a, a proximal end 308b, and a middle 308c. In addition, each elongated support post 308 includes a plurality of eyelets or apertures 332 for suturing stent 300 to valve leaflets. Apertures 332 may have different shapes and sizes. At least one elongated support post 308 may extend slightly beyond the first end 338 collectively defined by all the proximal cells 306, as seen in FIG. 4.

Post connections 310 may be positioned at two locations along each elongated support post 308. As noted above, such positioning reduces post flexibility and the strains experienced in post connections 310. Two post connections 310 may be positioned on opposite sides of the proximal end 308b of an elongated support post 308 and join the elongated support post 308 to the proximal ends 306b of certain proximal cells 306 in the second row 328. Another two post connections 310 may be located on opposite sides at or near the middle 308c of an elongated support post 308 and join the middle of the support post to the middle portions 306c of certain proximal cells 306 in the first row 324.

Figures 5A, 5B:
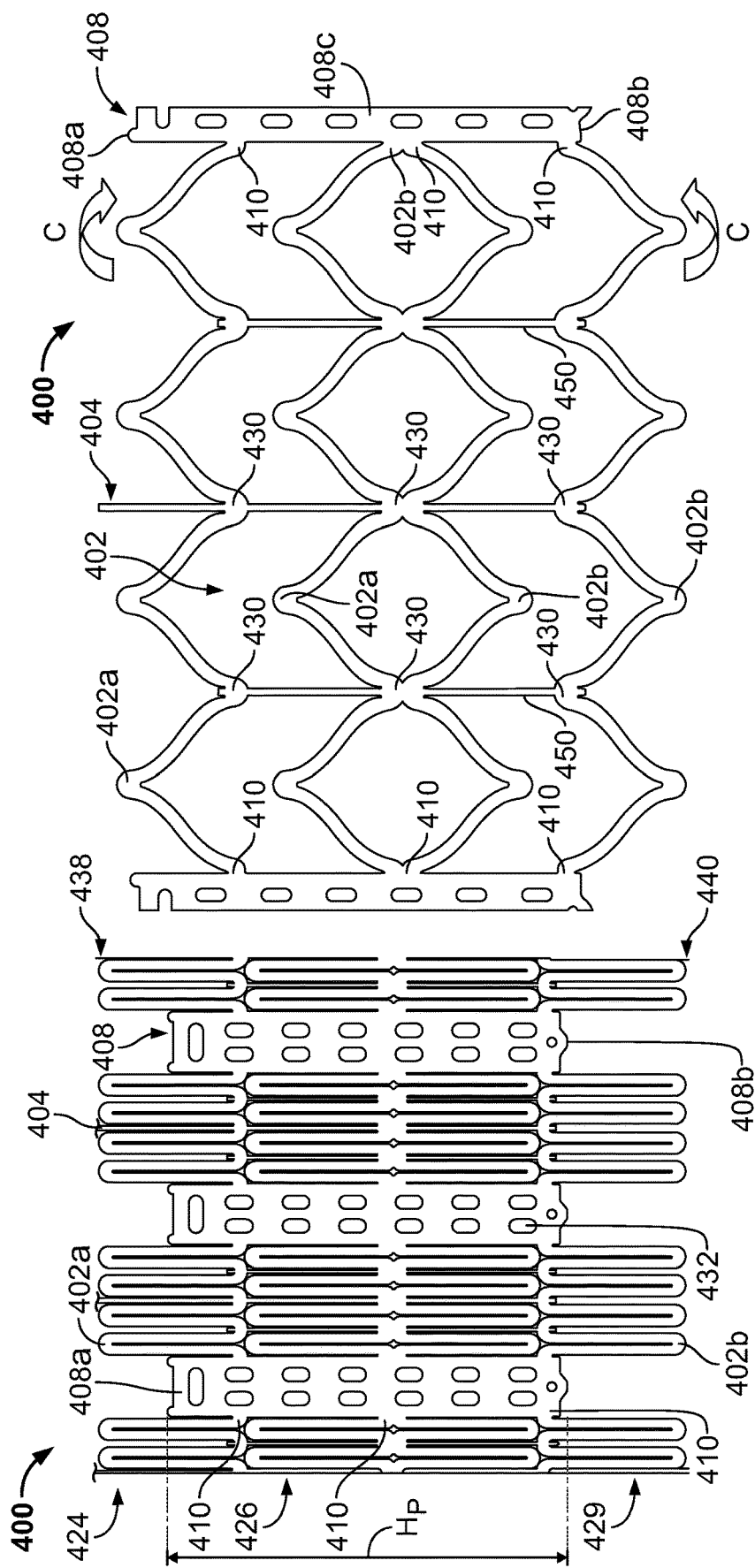
FIG. 5A is a developed view of a stent in an unexpanded condition with a plurality of posts each connected to cells at three locations.
FIG. 5B is a developed view of the stent of FIG. 5A in an expanded condition.

With reference to FIGS. 5A and 5B, a stent 400 includes a plurality of cells 402, a plurality of support struts 404, one or more elongated support posts 408 and post connections 410 coupling the elongated posts 408 to cells 402. FIG. 5A shows stent 400 in a flat, rolled out, unexpanded condition, whereas FIG. 5B depicts stent 400 in a flat, rolled out, fully-expanded condition. Post connections 410 are positioned at three locations along each elongated support post 408. Stent 400 further includes at least one runner or bar 450 extending longitudinally along cells 402. Bars 450 enable the length of stent 400 to change substantially uniformly between the unexpanded and expanded conditions. The height and width of bars 450 may vary to accommodate various strength needs.

As discussed above, stent 400 includes a plurality of cells 402. Several cell connections 430 join cells 402 to one another. Cells 402 may have a distal end 402a, a proximal end 402b, or both a distal end and a proximal end. All the cells 402 collectively define a first end 438 and a second end 440 and may be arranged in one or more longitudinal rows. For instance, stent 400 may include a first row 424, a second row 426 and a third row 429 of cells 402 oriented substantially parallel to one another. The first row 424, second row 426 and third row 429 of cells 402 are not continuous and may be disrupted by one or more elongated support posts 408 interposed in the rows.

Each elongated support post 408 includes a distal end 408a, a proximal end 408b, a middle 408c, and a plurality of eyelets or apertures 432 for suturing stent 400 to the valve leaflets. The height $H_p$ of each elongated support post 408 defines the distance between distal end 408a and proximal end 408b. In the embodiment shown in FIG. 5A, all elongated support posts 408 are positioned between the first end 438 and the second end 440 collectively defined by cells 402. The distal ends 402a of the cells 402 in the first row 424 extend distally beyond the distal ends 408a of each elongated support post 408 in the unexpanded condition. The proximal ends of the cells 402 in the third row 429 extend proximally beyond the proximal ends 408b of each elongated support post 408 in the unexpanded condition. As a result, cells 402 in rows 424 and 429 can be bent outwardly into a C-shape in the directions indicated by arrows C so that stent 400 holds onto the stenotic native valve leaflets when the stent is positioned in the valve annulus 2.

Post connections 410 join elongated support posts 408 to cells 402. As shown in FIG. 5B, stent 400 includes post connections 410 at three locations along each elongated support post 408. First post connections 410 are located on opposite sides of (or near) the proximal end 408b of elongated posts 408. Second post connections 410 are also positioned on opposite sides of (or near) the middle 408c of elongated support posts 408. Third post connections 410 are located on opposite sides of elongated support posts 408 near distal ends 408a. The post connections 410 near distal ends 408a may, for example, be positioned at about three-quarters of height $H_p$.

As discussed above, stent 400 may further include one or more bars 450 for facilitating uniform expansion of the stent. Bars 450 join cells 402 from first row 424 through the third row 429. As seen in FIG. 5B, each bar 450 passes through cell connections 430 but does not extend past the first end 438 or the second end 440 collectively defined by cells 402. Bars 450 pass through the valleys formed between cells 402.

Stent 400 also includes one or more support struts 404 connected to a portion of the valleys formed between the distal ends 402a of cells 402 in the first row 424. Alternatively, support struts 404 may be connected directly to the distal ends 402a of cells 402. In some embodiments, support struts 404 may connect cells 402 to another group of cells (not shown).

FIG. 6A shows a stent 500 in a flat, rolled out, unexpanded state, while FIG. 6B illustrates stent 500 in a flat, rolled out, expanded state. Stent 500 includes a plurality of cells 502, one or more elongated support posts 508, and one or more bars 550 for enabling the length of stent 500 to change substantially uniformly between the unexpanded and expanded states. The structure and operation of stent 500 are similar to the structure and operation of stent 400, but stent 500 includes post connections 510 specifically located on opposite sides of the distal ends 508a of each elongated support post 508, rather than inward of the distal ends as with stent 400. Stent 500 may further include one or more support struts 504 joining the distal ends 502a of some cells 502 to another set of cells (not shown).

Cells 502 of stent 500 are arranged in rows, namely first row 524 and second row 528. First row 524 and second row 528 of cells 502 are oriented substantially parallel to each other, as seen in FIG. 6A. Several cell connections 530 join cells 502 to one another. Each cell connection 530 usually forms a valley or a peak between two cells 502. Bars 550 interconnect adjacent cells 502 positioned in different rows. In some embodiments, bars 550 may be connected to three cell connections 530. Cells 502 collectively define a first end 538 and a second end 540.

Elongated support posts 508 are interposed between sets of cells 502 and traverse both rows of cells. Each support post 508 has a distal end 508a, a proximal end 508b, a middle 508c, and a plurality of eyelets or apertures 532 for suturing stent 500 to the valve leaflets. The proximal end 508b of each elongated post 508 does not extend beyond the second end 540 collectively defined by all cells 502. The distal end 508a extends slightly beyond the first end 538 collectively defined by all cells 502.

As seen in FIGS. 6A and 6B, stent 500 includes post connections 510 joining each elongated support post 508 to adjacent cells 502 at three particular locations along the length of the support post. First post connections 510 join opposite sides near the proximal end 508b of an elongated support post 508 to the adjacent cells 502 located in the second row 528. Second post connections 510 join opposite sides of the middle 508c of each elongated support post 508 to the segments common to the adjacent cells 502 in the first row 524 and the second row 528. Third post connections 510 join opposite sides of the distal end 508a of an elongated support post 508 to the adjacent cells 502 located in the first row 524. These last post connections 510 may be located at the very end of the support post 508.

Figure 7B:
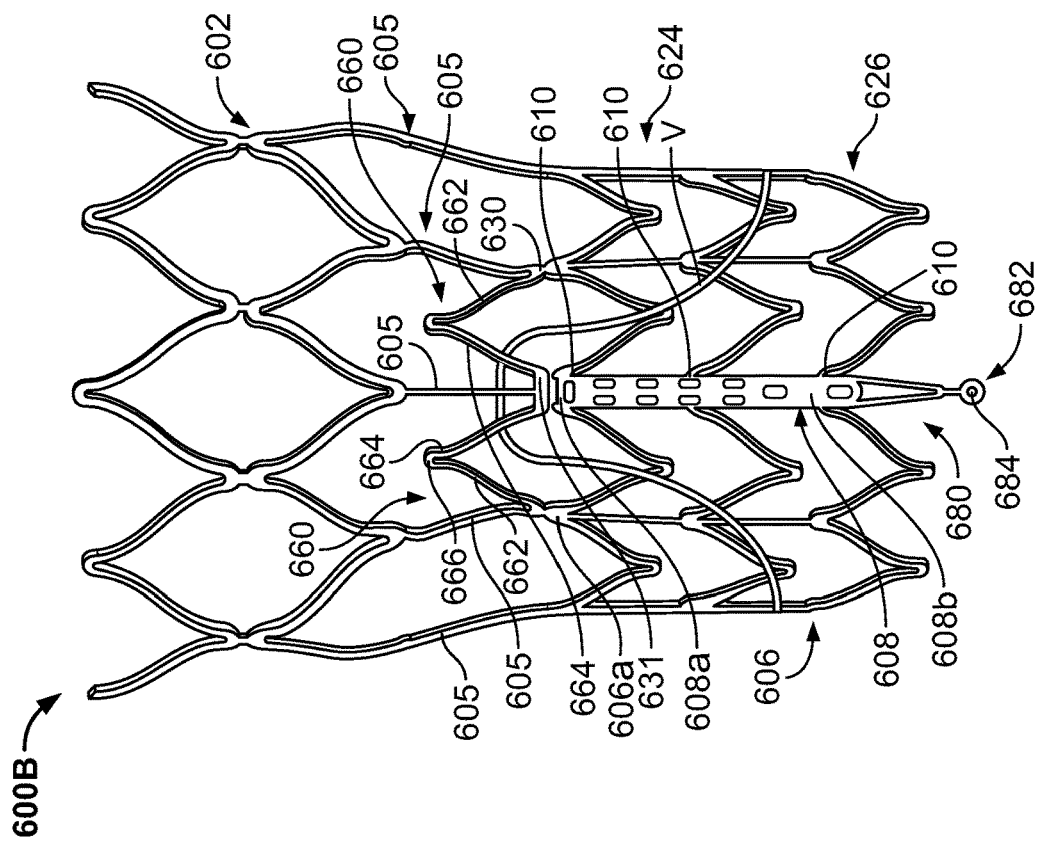
FIG. 7B is a partial front elevational view of a stent showing a post connected to cells at three locations.
Figure 7A:
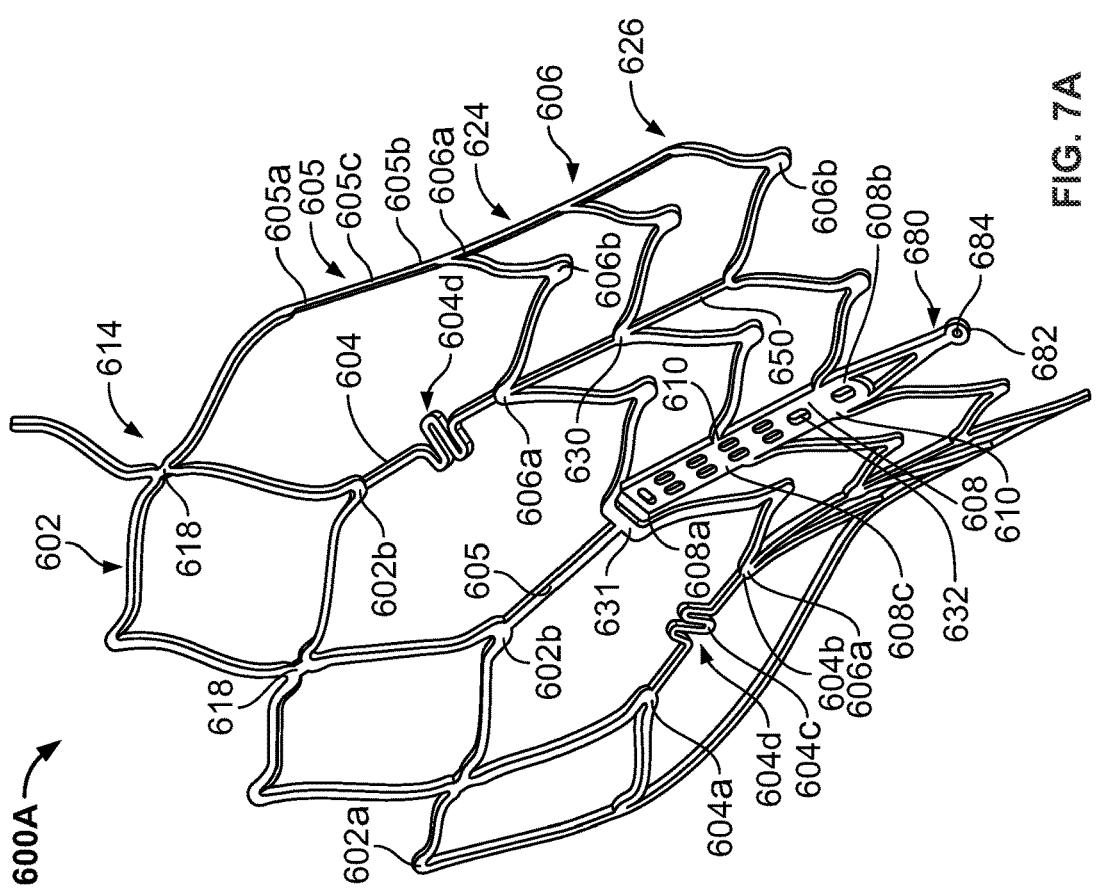
FIG. 7A is a partial perspective view of a stent showing a post connected to cells at two locations.

FIGS. 7A and 7B show similar stents 600A and 600B with different numbers of post connections 610. With reference to FIG. 7A, stent 600A includes distal cells 602, proximal cells 606 and support struts 604, 605 interconnecting the distal cells and proximal cells. Distal cells 602 and proximal cells 606 are continuously connected around the entire circumference of stent 600A, thereby allowing symmetric expansion and increased radial force.

Distal cells 602 may be arranged in one or more longitudinal rows. For example, stent 600A may include only one row 614 of distal cells 602. Each distal cell 602 has a distal end 602a and a proximal end 602b, and may have a diamond shape upon expansion. Distal cells 602 are connected to one another along row 614 via cell connections 618. Each cell connection 618 is positioned at a valley formed between two adjacent distal cells 602. The proximal ends 602b of distal cells 602 may be coupled in an alternating pattern to two different kinds of support struts 604 and 605.

Support strut 605 has a distal end 605a, a proximal end 605b, and a middle portion 605c between the distal end and the proximal end. The distal end 605a of each support strut 605 is connected to the proximal end 602b of a distal cell 602, whereas the proximal end 605b of each support strut 605 is connected to the distal end 606a of a proximal cell 606.

Support strut 604 has a distal end 604a, a proximal end 604b, and a middle portion 604c between the distal end and the proximal end. The distal end 604a of each support strut 604 is connected to the proximal end 602b of a distal cell 602. The proximal end 604b of each support strut 604 is coupled to the distal end 606a of a proximal cell 606. The middle portion 604c of each support strut 604 includes a section 604d featuring a non-linear shape. For example, non-linear section 604d may have a sinusoidal or wave shape.

Proximal cells 606 are arranged in one or more longitudinal rows. For instance, stent 600A may include a first row 624 and a second row 626 of proximal cells 606. First row 624 and second row 626 of proximal cells 606 are oriented substantially parallel to each other.

Each proximal cell 606 may have an arrow shape in the expanded condition defined by a pair of peaks 606a on opposite sides of a valley 606b in one stent section, another pair of peaks 606a on opposite sides of a valley 606b in another stent section, and a pair of bars 650 connecting the stent sections together.

Cell connections 630 interconnect proximal cells 606 positioned in the same row. Each cell connection 630 may be positioned at a peak 606a shared by two adjacent proximal cells 606 located in the same row.

Bars 650 not only define proximal cells 606, but also interconnect proximal cells 606 located in adjacent rows, thereby allowing uniform expansion of proximal cells 606. Each bar 650 may be connected to one or more cell connections 630.

Stent 600A further includes one or more elongated support posts 608. Each elongated support post 608 has a distal end 608a, a proximal end 608b, and a middle 608c, and includes one or more eyelets or apertures 632 for suturing stent 600A to the valve leaflets.

Stent 600 may further include an interlocking feature 680 protruding proximally from the proximal end 608b of elongated support post 608. Interlocking feature 680 may have a substantially triangular shape and is configured to be attached to a delivery instrument or another cell. In one embodiment, interlocking feature 680 has a circular portion 682 having an aperture 684.

Post connections 610 join each elongated support post 608 to proximal cells 606 located adjacent to the support post. In the embodiment shown in FIG. 7A, stent 600A includes two post connections 610 on opposite sides of the middle 608c of each elongated support post 608 and another two post connections 610 on opposite sides near the proximal end 608b of each elongated support post 608. As a result, the distal ends 608a of elongated support posts 608 are free and disconnected from any proximal cell 606. This configuration provides stent 600A with a high degree of flexibility and reduces the likelihood of distortion in the distal portion of elongated support post 608 contorting the commissure region and thus the valve function.

The proximal cells 606 adjacent to the distal end 608a of elongated support post 608 may be joined to each other by a particular kind of cell connection 631. Cell connection 631 does not form a peak but rather a straight line in the annular direction of stent 600A. As seen in FIG. 7A, cell connection 631 is not connected to elongated support post 608, thereby enabling the distal end 608a of the stent post to flex.

Referring to FIG. 7B, stent 600B is substantially similar to stent 600A. However, stent 600B may include post connections 610 at three locations along elongated support post 608. For example, stent 600B may include post connections 610 on opposite sides of the distal end 608a of each elongated support post 608, other post connections 610 on opposite sides of the middle 608c of each elongated support post 608, and other post connections 610 on opposite sides near the proximal end 608b of each elongated support post 608. As discussed above, post connections 610 join elongated support post 608 to proximal cells 606 adjacent to elongated support post 608.

In the embodiment shown in FIG. 7B, stent 600B only includes struts 605 interconnecting the distal cells 602 and the proximal cells 606 and does not contain any struts 604 with a non-linear section 604d. It is envisioned, however, that stent 600B may include both struts 604 and struts 605.

Stent 600B may include additional cell structural members 660 located distally of each elongated support post 608. Each cell structural member 660 includes a first support member 662 and a second support member 664 joined at a peak or distal end 666. First support member 662 and second support member 664 together form a triangular structure connected to proximal cells 606 located on opposite sides of the distal end 608a of elongated support post 608. Each first support member 662 may be connected to a distal end peak 606a of a proximal cell 606 via a cell connection 630. Each second support member 664 may be connected to a straight connection 631. In the embodiment shown in FIG. 7B, connection 631 is not connected to proximal cells 606 or to an elongated support post 608, and is only coupled to the second support members 664 of each cell structural member 660. As shown in FIG. 7B, the connection 631 and the connected portions of support members 664 and struts 605 may be fitted over an existing surgical or collapsible bioprosthetic valve V to lock the new valve in place. In lieu of elongated support post 608, stent 600A or stent 600B may include continuous proximal cells 606 disjointed in the area where the leaflet commissures would be attached.

FIG. 8A shows a stent 700 in a flat, rolled out, unexpanded condition and FIG. 8B shows stent 700 in an expanded condition. Stent 700 generally includes distal cells 702, proximal cells 706, and a plurality of support struts 704 interconnecting distal cells 702 and proximal cells 706.

Distal cells 702 are arranged in one or more longitudinal rows. In the embodiment shown in FIGS. 8A and 8B, stent 700 includes one longitudinal row 714 of distal cells 702. Cell connections 718 join adjacent distal cells 702 arranged in the same row. Some adjacent distal cells 702, however, are connected by spacers 770. Spacers 770 allow symmetric expansion of distal cells 714 and additional spacing for the coronary arteries. Each spacer 770 may further include an interlocking feature, eyelets, radiopaque material, a landing-zone/latch-site for implanting another similar expandable valve, or a combination thereof.

Although both spacers 770 and cell connections 718 connect adjacent distal cells 702, spacers 770 separate adjacent distal cells 702 farther from each other than cell connections 718. In some embodiments, three cell connections 718 may continuously couple four adjacent distal cells 702 before a spacer 770 joins the next adjacent distal cell. Spacers 770 may be arranged between cells 702 so as to be positioned in axial alignment with support posts 708.

Each distal cell 702 has a distal end 702a and a proximal end 702b. Upon expansion of stent 700, each distal cell 702 may have a diamond shape, as shown in FIG. 8B.

The proximal ends 702b of each distal cell 702 may be connected to a support strut 704. Each support strut 704 has a distal end 704a and proximal end 704b. The distal end 704a of each support strut 704 is coupled to a distal cell 702. The proximal end 704b of each support strut 704 is connected to a proximal cell 706. Specifically, the proximal end 704b of each support strut 704 is coupled to a cell connection 730 located at a valley formed between two adjacent proximal cells 706.

As seen in FIG. 8B, the proximal end 704b of each support strut 704 is positioned proximally of the distal ends 708a of elongated support posts 708. As a consequence, the outward flaring of stent 700 in an expanded condition can start proximally to the distal end of the cylindrical region (i.e., proximal cells 706).

Proximal cells 706 may be arranged in one or more longitudinal rows. In some embodiments, stent 700 may include a first row 724 and a second row 726 oriented substantially parallel to each other. Each proximal cell 706 may feature an arrow shape in the expanded condition defined by a distal end or peak 706a between two valleys 706b and 706c in one stent section, another peak 706a between two valleys 706b and 706c in another stent section, and a pair of bars 750 connecting the stent sections together.

Cell connections 730 couple adjacent proximal cells 706 arranged in the same row. Each cell connection 730 may be located at a valley 706b, 706c shared by two adjacent proximal cells 706 in the same row.

Bars 750 not only define proximal cells 706, but also connect proximal cells 706 located in adjacent rows. Each bar 750 may interconnect several cell connections 730 and permit uniform expansion of proximal cells 706. In some embodiments, each bar 750 passes through at least three cell connections 730 and is oriented substantially parallel to the elongated support posts 708.

Each elongated support post 708 of stent 700 has a distal end 708a, a proximal end 708b, and a middle 708c. Proximal cells 706 may be connected to an elongated support post 708 at three locations via connecting members 710. A first pair of connecting members 710 may couple opposite sides of the distal end 708a of an elongated support post 708 to two cell connections 730 attached to support struts 704. A second pair of connecting members 710 may couple opposite sides of the middle 708c of the elongated support post 708 to two cell connections 730 located at the proximal ends 706b, 706c of two different proximal cells 706. A third pair of connecting members 710 may couple opposite sides near the proximal end 708b of the elongated support post 708 to two cell connections 730 located at the proximal ends 706b, 706c of two other proximal cells 706 located in the second row 726.

Stent 700 further includes an interlocking feature 780 protruding proximally from the proximal end 708b of one or more elongated support posts 708. Interlocking feature 780 is configured to be attached to a delivery system and/or another valve. For instance, a delivery system may hold onto stent 700 through interlocking feature 780. In addition, another valve may be integrated with or attached to stent 700 via interlocking feature 780. Interlocking feature 780 may have any suitable shape. In the illustrated embodiment, interlocking feature 780 has a triangular shape and a circular end portion 782 defining an aperture 784. The stent 700 of a new valve may be fitted over an existing surgical or collapsible bioprosthetic valve V to lock the new valve in place.

Figure 9B:
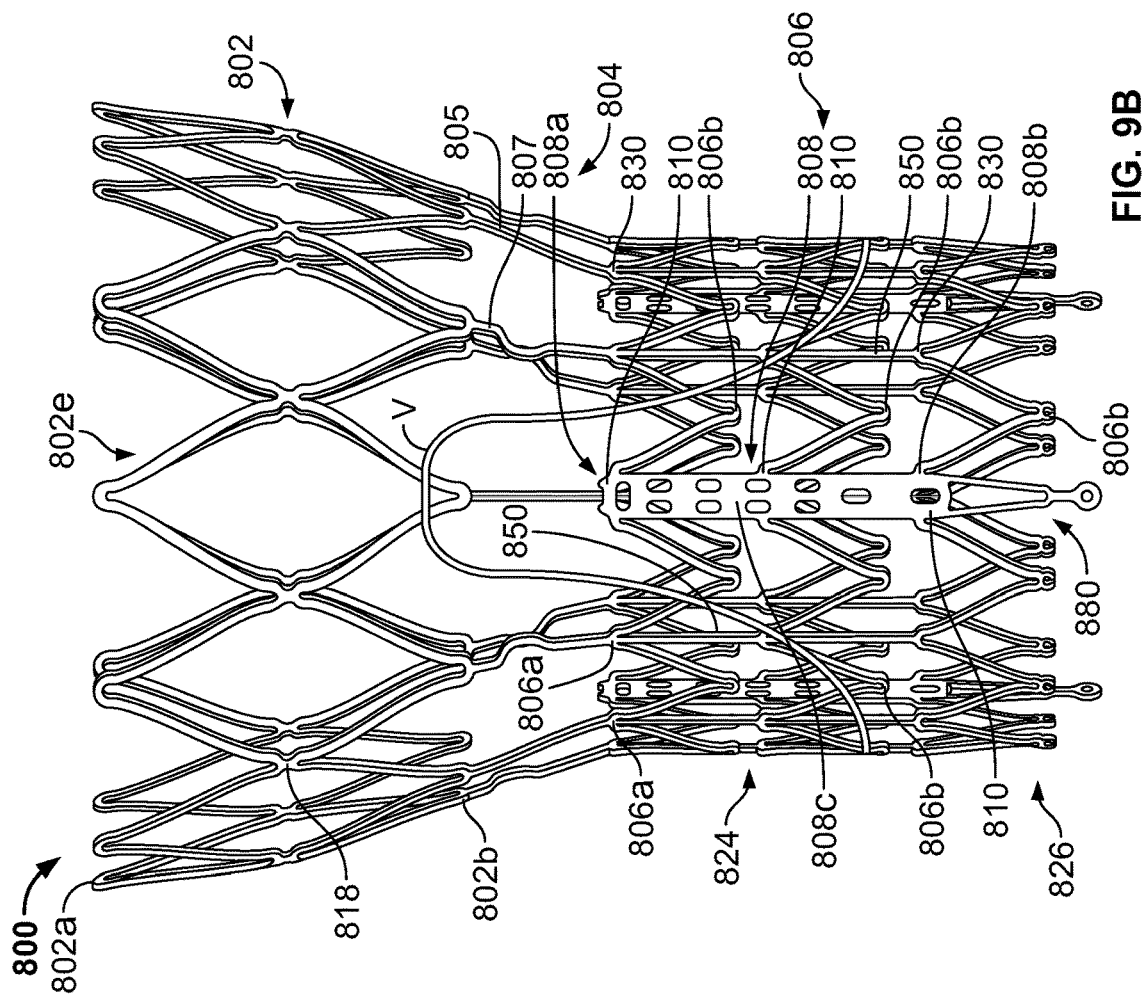
FIG. 9B is a front elevational view of the stent of FIG. 9A in an expanded condition.
Figure 9A:
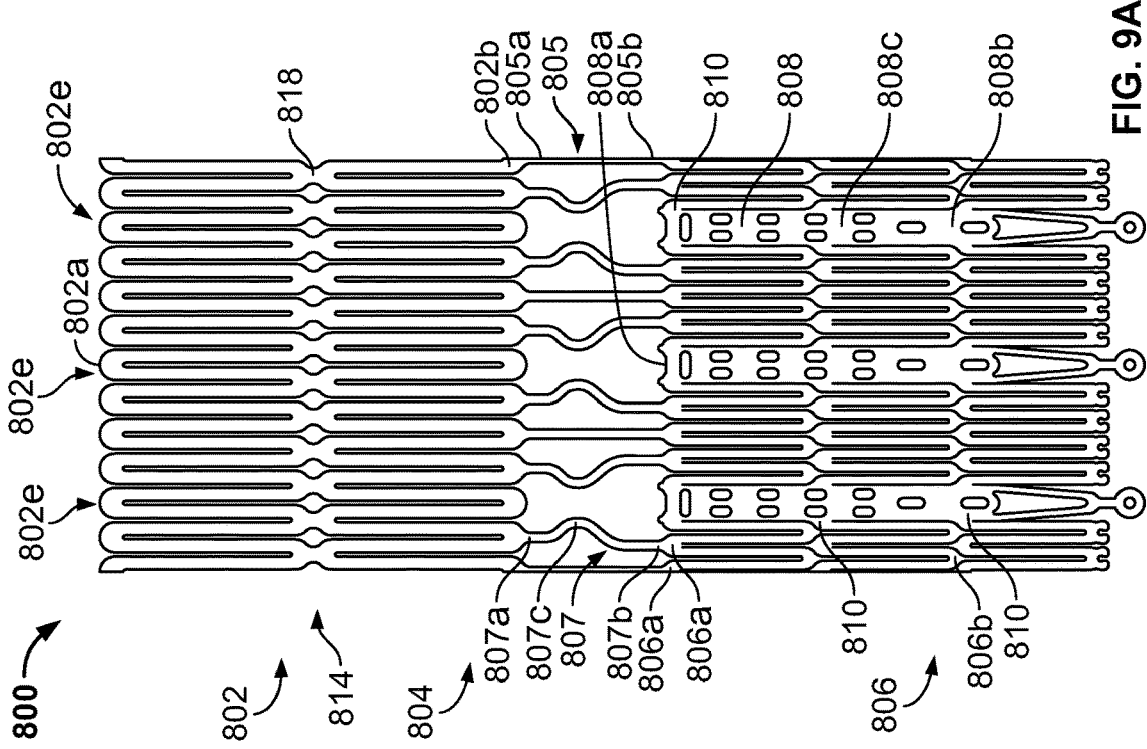
FIG. 9A is a developed view of a stent in an unexpanded condition including support struts each having a curved middle portion.

FIG. 9A shows a stent 800 in a flat, rolled out, unexpanded condition and FIG. 9B depicts stent 800 in an expanded condition. Stent 800 is substantially similar to stent 700 described above and generally includes distal cells 802, proximal cells 806 and support strut arrays 804 interconnecting distal cells 802 and proximal cells 806. Each support strut array 804 includes two kinds of support struts, namely a support strut 805 and two support struts 807.

Each distal cell 802 has a distal end 802a and a proximal end 802b. All distal cells 802 are arranged in one or more longitudinal rows 814. Cell connections 818 join adjacent distal cells 802 in the same row 814. In the embodiment shown in FIGS. 9A and 9B, stent 800 includes only one row 814.

Some distal cells 802 are not connected to any support struts, while other distal cells 802 are attached to a support strut 805 or 807. The distal cells 802e that are not attached to any support strut 805 or 807 allow further expansion of the longitudinal row 814 of distal cells. In some embodiments, stent 800 includes three distal cells 802 connected to support struts 805, 807 for every distal cell 802e that is not attached to any support strut 805 or 807. Each distal cell 802e that is not connected to any support strut 805 or 807 may be positioned between a series of distal cells 802 which is not connected to the support strut 805 or 807. For example, in one embodiment, a single distal cell 802e which is not connected to support struts 805 or 807 may be located between and adjacent two distal cells 802 attached to support struts 807. In this embodiment, shown in FIG. 9A, each distal cell 802 coupled to a support strut 807 is located adjacent to a distal cell 802 connected to a support strut 805.

As discussed above, each support strut array 804 includes two kinds of support struts—a support strut 805 and a pair of support struts 807. Each support strut 805 has a distal end 805a and a proximal end 805b and may be formed of a substantially flexible material. Support struts 805 may have a linear configuration along their entire length. The distal end 805a of each support strut 805 is connected to a distal cell 802, while the proximal end 805b of each support strut 805 is connected to a proximal cell 806.

In some embodiments, support struts 805 may not be connected to all distal cells 802. For example, support struts 805 may be coupled to one of every four distal cells 802. Each support strut 805 may be positioned between two support struts 807.

Each support strut 807 has a distal end 807a, a proximal end 807b and a middle portion 807c between the distal end and the proximal end. The distal end 807a and the proximal end 807b of each support strut 807 have substantially linear or straight configurations. At least part of middle portion 807c of each support strut 807 has a curved profile or configuration. In some embodiments, middle portions 807c have a C-shape or an inverted C-shape.

The distal end 807a of each support strut 807 may be connected to a single distal cell 802. The proximal end 807b of each support strut 807 may be coupled to a proximal cell 806. In certain embodiments, support struts 807 may be connected only to the proximal cells 806 adjacent to an elongated support post 808. As shown in FIGS. 9A and 9B, one support strut 807 with a C-shaped middle portion 807c may be connected to a proximal cell 806 located adjacent one side of an elongated support post 808, while another support strut 807 with an inverted C-shaped middle portion 807c may be connected to a proximal cell 806 positioned adjacent the opposite side of that elongated support post 808.

Each proximal cell 806 may have an inverted arrow shape upon expansion defined by a pair of peaks 806a on opposite sides of a valley 806b in one stent section, another pair of peaks 806a on opposite sides of a valley 806b in another stent section, and a pair of bars 850 connecting the stent sections together. Proximal cells 806 may be arranged in one or more longitudinal rows. In some embodiments, stent 800 includes proximal cells 806 in a first row 824 and in a second row 826. Cell connections 830 interconnect adjacent proximal cells 806 positioned in the same row. Each cell connection 830 may be located at a peak 806a shared by two adjacent proximal cells 806 located in the same row. The valleys 806b at the proximal ends of the cells in the second row 824 may also form the valleys 806b at the distal ends of the adjacent cells in the first row 826.

As seen in FIGS. 9A and 9B, all support struts 805 and 807 may be connected to the peaks 806a of the proximal cells 806 in first row 824. Alternatively, some or all support struts 805 and 807 may be attached to the valleys 806b of the proximal cells 806 in the first row 824.

Bars 850 not only define proximal cells 806, but also connect proximal cells 806 located in adjacent rows. Specifically, each bar 850 may connect several cell connections 830. In some embodiments, a bar 850 may join at least three cell connections 830 located in different rows and therefore permit uniform expansion of stent 800.

Some proximal cells 806 may be attached to an elongated support post 808. Stent 800 may have one or more elongated support posts 808. In the embodiment shown in FIG. 8A, stent 800 has three such support posts 808. Each support post 808 has a distal end 808a, a proximal end 808b, and a middle 808c. Post connections 810 attach some proximal cells 806 to opposite sides of the distal end 808a, the proximal end 808b and the middle 808c of the elongated support post 808.

Stent 800 may further include an interlocking feature 880 protruding proximally from the proximal end 808b of each elongated support post 808. Interlocking feature 880 may be substantially similar to the interlocking feature 780 of stent 700. The stent 800 of a new valve may be fitted over an existing surgical or collapsible bioprosthetic valve V to lock the new valve in place or may be used to lock the stent 800 at the sinotubular junction 4.

FIGS. 10A, 10B, and 10C illustrate several embodiments of stents with substantially rigid posts or bars. These stents also have different interlocking features configured to be engaged to a delivery system and/or another valve.

FIG. 10A depicts a portion of a stent 900 in a flat, rolled out, unexpanded condition. Stent 900 generally includes distal cells 902, proximal cells 906, and support struts 904 and 905 interconnecting distal cells 902 and proximal cells 906. Some proximal cells 906 are attached to one or more elongated support posts 908 made wholly or partly of a substantially solid or rigid material.

Distal cells 902 are arranged in one or more longitudinal rows. Stent 900 may include one longitudinal row 914 of distal cells 902. Each distal cell 902 has a distal end 902a, a proximal end 902b, and a middle portion 902c between the distal end and the proximal end. Cell connections 918 join adjacent distal cells 902 at their middle portions 902c.

At least one compartment 903 is interposed between the series of distal cells 902 in row 914. Preferably, stent 900 includes one compartment 903 for each elongated support post 908. Each compartment 903 includes a distal end 903a, a proximal end 903b, and a middle portion 903c between the proximal end and the distal end. The distal end 903a and the proximal end 903b of each compartment 903 may have substantially linear or straight configurations oriented substantially parallel to each other at least in the unexpanded condition of stent 900. Thus, in the unexpanded condition, compartment 903 has a generally rectangular shape. Cell connections 918 may join opposite sides of the middle portion 903c of the compartment 903 to neighboring distal cells 902.

The distal end 903a of compartment 903 may include an interlocking feature 980 configured to be attached to a delivery system and/or another valve. Interlocking feature 980 protrudes proximally from the distal end 903a into the interior of compartment 903. In the embodiment shown in FIG. 10A, interlocking feature 980 includes rounded protrusion 982 having an aperture 984.

As discussed above, stent 900 includes support struts 904 and support struts 905. At least some of support struts 904 and support struts 905 may be made partially or entirely of a substantially rigid material to minimize a change in stent length, thereby reducing the risk of valve damage during crimping of the prosthetic valve and providing a more consistent valve function in various implant diameters. Support struts 904 interconnect the proximal end 902b of a distal cell 902 to the distal end 906a of a proximal cell 906. In some embodiments, every distal cell 902 may be connected to a proximal cell 906 via a support strut 904.

Support struts 905 couple the proximal end 903b of compartment 903 to the distal end 908a of the elongated support post 908. In some embodiments, stent 900 may include two support struts 905 connecting a single elongated support post 908 to a single compartment 903. Each of the support struts 905 may have a distal end 905a and a proximal end 905b, and the struts may collectively form a triangular shape in the unexpanded condition of stent 900. The proximal ends 905b of the two support struts 905 may be connected to spaced apart portions of the same elongated support post 908. The distal ends 905a of the two support struts 905 may converge for attachment to the proximal end 903b of compartment 903 at a single point. In this arrangement, support struts 905 define an oblique angle relative to one another.

All proximal cells 906 are arranged in one or more longitudinal rows and some are attached to at least one elongated support post 908. Cell connections 930 connect proximal cells 906 arranged on the same row, while bars or runners 950 join adjacent proximal cells 906 located in different rows.

As noted above, stent 900 includes one or more elongated support posts 908. Each elongated support post 908 includes a distal end 908a, a proximal end 908, and a middle 908c. Post connections 910 join some proximal cells 906 to an elongated support post 908 at three locations. First post connections 910 connect two proximal cells 906 to opposite sides of the distal end 908a of the elongated support post 908. Second post connections 910 connect two proximal cells 906 to opposite sides of the middle 908c of the elongated support post 908. Third post connections 910 coupled two proximal cells 906 to opposite sides near the proximal end 908b of the elongated support post 908.

FIG. 10B illustrates a stent 1000A and FIG. 10C illustrates a stent 1000B which are substantially similar to one another. Stents 1000A and 1000B have interlocking features 1080 at different locations and different kinds of elongated support posts.

As shown in FIG. 10B, stent 1000A includes at least one elongated support post 1008, distal cells 1002 and proximal cells 1006 but does not include support struts. In other words, distal cells 1002 are connected directly to proximal cells 1006.

Distal cells 1002 may be arranged in one or more longitudinal rows. In some embodiments, stent 1000A may include a first row 1014, a second row 1016 and a third row 1022 of distal cells 1002 oriented substantially parallel to each other. Each distal cell has a distal end or peak 1002a, a proximal end or valley 1002b, and middle portions 1002c. The valley 1002b of a distal cell 1002 in one row may join the peak 1002a of a distal cell in another row which is not adjacent to the one row. Upon expansion, each distal cell 1002 may have a diamond shape. Distal cells 1002 may be formed of a substantially flexible material and therefore the cells can lengthen and expand to larger diameters.

Cell connections 1018 join adjacent distal cells 1002 in the same row. Distal cells 1002 in adjacent rows are joined by sharing common cell segments. Stent 1000A further includes one or more cell spacers 1070 each interconnecting two adjacent distal cells 1002 of the first row 1014. Preferably, stent 1000A includes a cell spacer 1070 for each elongated support post 1008. In the embodiment shown in FIG. 10B, a cell spacer 1070 may form a distal portion or end of a distal cell 1002 which is located in the second row 1016 and connected to an elongated support post 1008. Cell spacer 1070 permits further expansion of stent 1000A, and may provide clearance between distal cells 1002 to accommodate the coronary arteries.

As noted above, the proximal ends 1002b of a distal cell 1002 in the second row 1016 are connected to the distal end 1008a of an elongated support post 1008. In addition, two distal cells 1002 in the third row 1022 may be connected by their middle portions 1002c to opposite sides of the distal end 1008a of the elongated support post 1008. Post connections 1010 thus join the distal end 1008a of elongated support post 1008 to both a distal cell 1002 in second row 1016 and to two distal cells 1002 in third row 1022 positioned on opposite sides of elongated support post 1008.

The distal cells 1002 in third row 1022 are directly connected to the proximal cells 1006 in a first row 1024 by a runner or bar 1050. Bar 1050 is connected at one end to a cell connection 1018 in the third row 1022 of distal cells 1002, and at the other end to cell connection 1030 in the first row 1024 of proximal cells 1006.

Proximal cells 1006 may have a substantially inverted arrow shape upon expansion defined by a pair of distal peaks 1006a on opposite sides of a valley 1006b in one stent section, another pair of distal peaks 1006a on opposite sides of a valley 1006b in another stent section, and a pair of bars 1050 connecting the stent sections together. As seen in FIG. 10B, proximal cells 1006 may be arranged in longitudinal rows, such as first row 1024 and second row 1026. Cell connections 1030 located at distal peaks 1006a interconnect adjacent proximal cells 1006 located in the same row.

Bars 1050 not only define proximal cells 1006, but also interconnect proximal cells 1006 located in adjacent rows.

In particular, each bar 1050 may connect several cell connections 1030 located in different rows. Bars 1050 may be formed of a substantially solid or rigid material, thereby minimizing or limiting the change in stent length during expansion of stent 1000A.

As previously noted, each elongated support post 1008 has a distal end 1008a. Additionally, each elongated stent post 1008 has a proximal end 1008b and a middle 1008c, and may include a plurality of eyelets or apertures 1032. Elongated support posts 1008 may be formed of a substantially solid or rigid material, thereby minimizing or limiting changes in the stent length during expansion of stent 1000A.

In addition to the post connections 1010 described above, stent 1000A may include post connections 1010 joining two proximal cells 1006 to opposite sides of the middle 1008c of the elongated support post 1008. Other post connections 1010 may connect two proximal cells 1006 to opposite sides of the elongated support post 1008 near proximal end 1008b.

Stent 1000A further includes an interlocking feature 1080 protruding proximally from the proximal end 1008b of the elongated support post 1008. As discussed below, interlocking feature 1080 may be positioned at other locations. Interlocking feature 1080 is configured to be attached to a delivery system or another valve. In the embodiment shown in FIG. 10B, interlocking feature 1080 has a triangular shape and a circular portion 1082 having an aperture 1084.

Referring to FIG. 10C, stent 1000B is substantially similar to stent 1000A shown in FIG. 10B. However, stent 1000B includes an interlocking feature 1080 protruding distally from spacer 1070. Moreover, stent 1000B includes an elongated support post 1008 having a different configuration than the elongated support post of stent 1000A. The elongated support post 1008 of stent 1000B includes a post section 1008d which has a narrower width relative to the rest of elongated support post 1008, thereby enhancing the flexibility of the elongated support post. In addition, the proximal end 1008b of the elongated support post 1008 shown in FIG. 10C does not include eyelets or apertures 1032, as do the distal end 1008a and middle 1008c.

Figure 10D:
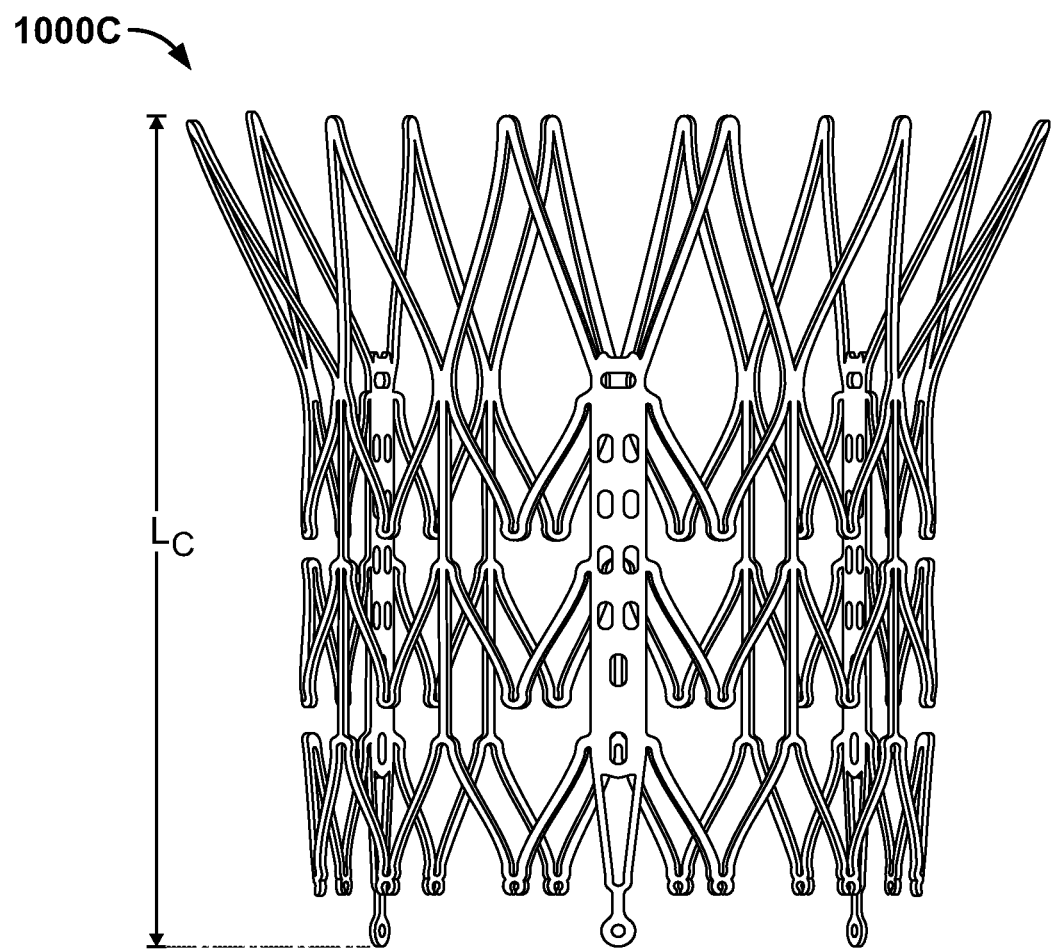
FIG. 10D is front elevational view of a stent flared to anchor at a sinotubular junction.
Figure 10E:
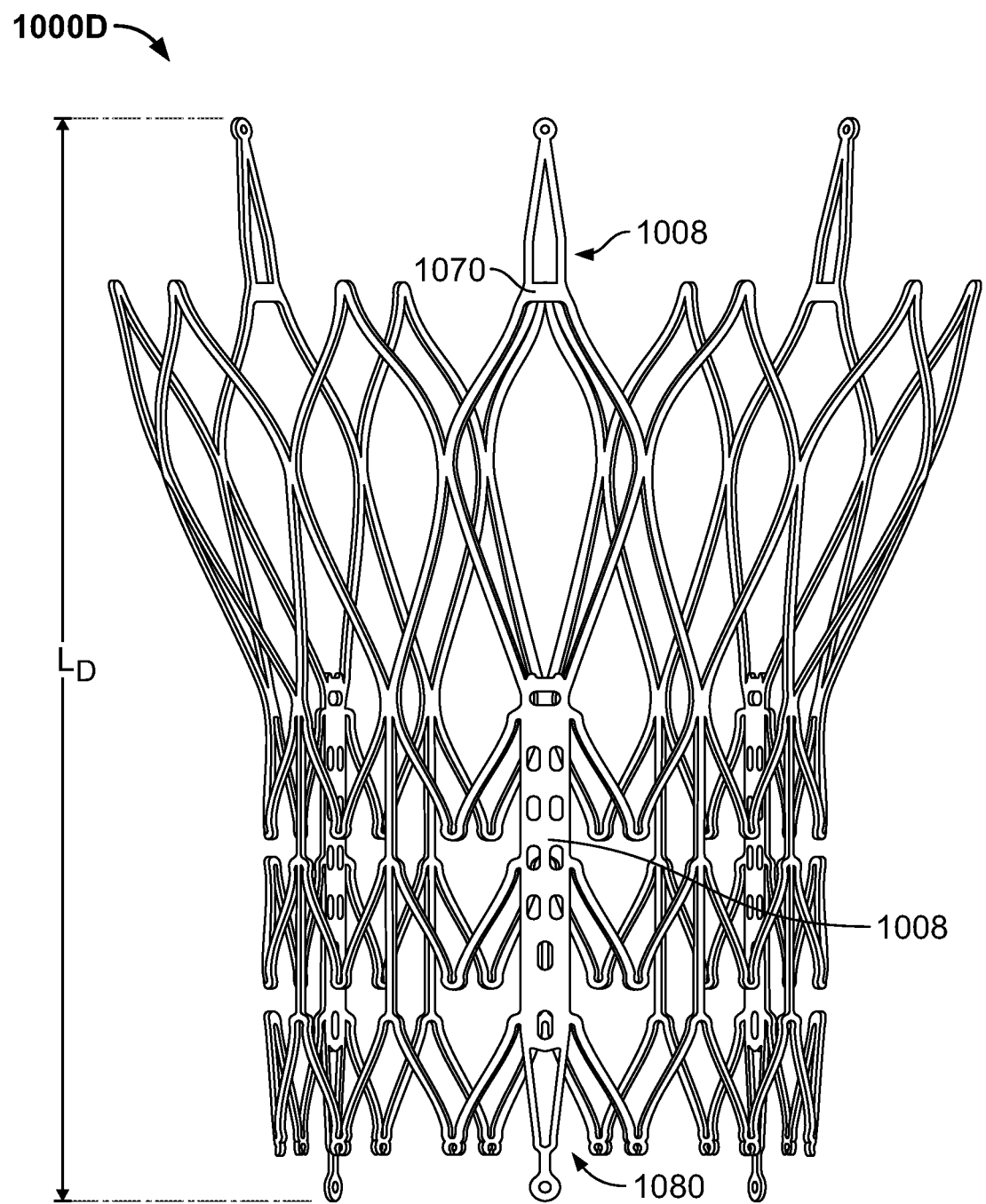
FIG. 10E is a front elevational view of a stent flared to anchor just above the sinotubular junction and at the base of the aorta.
Figure 10F:
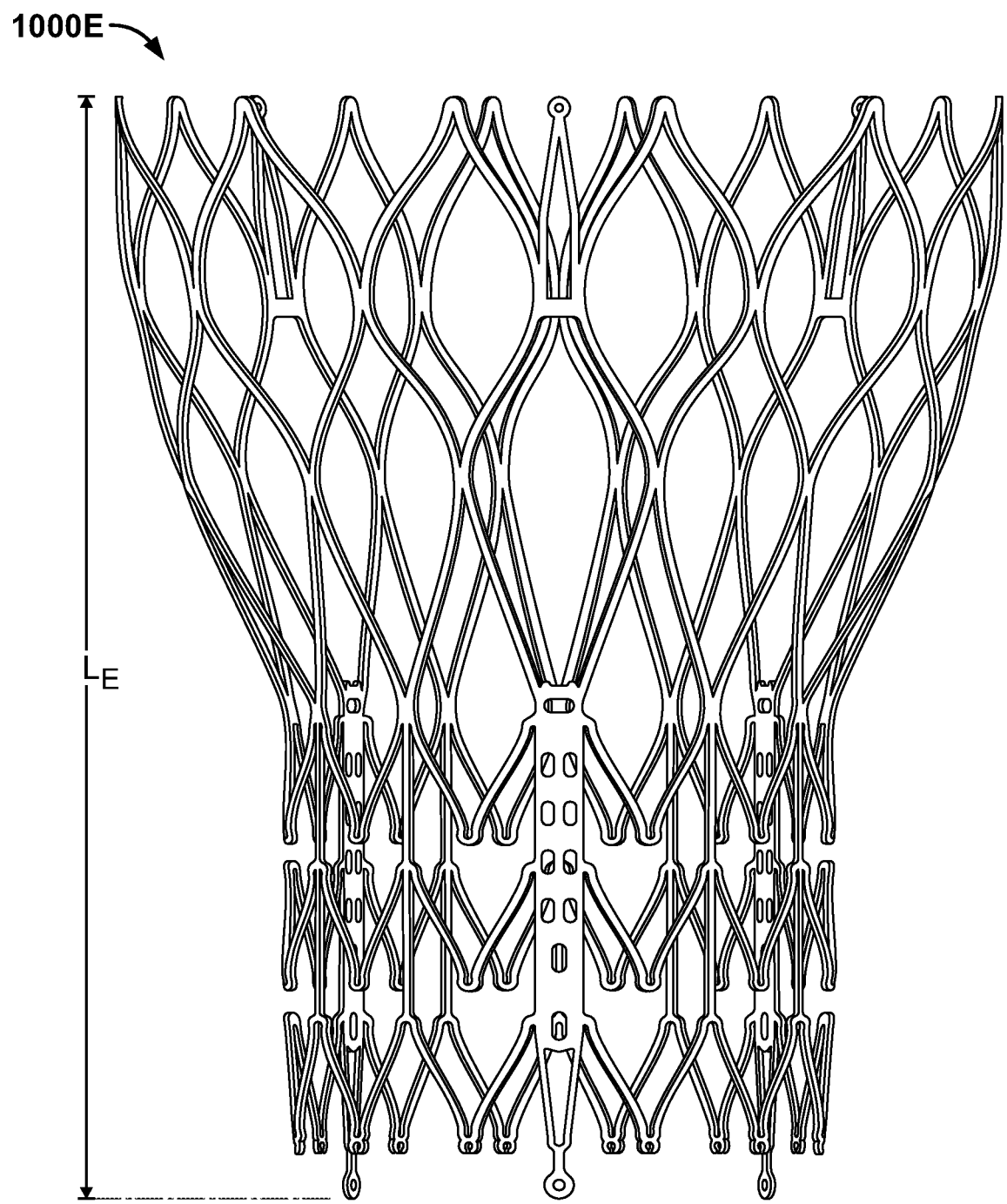
FIG. 10F is a front elevational view of a stent flared to anchor within the ascending aorta.

The stent designs depicted in FIGS. 10A, 10B, and 10C may be configured to have shorter lengths than depicted in the figures to anchor at different locations of the aortic root anatomy. For example, in FIG. 10D, stent 1000C is substantially similar to stent 1000A of FIG. 10B but has a suitable stent length $L_C$ (with fewer rows of distal cells) and a flared configuration for anchoring at the sinotubular junction 4 of the aortic root 10 in the expanded condition. (See FIG. 1.) With reference to FIG. 10E, stent 1000D is substantially similar to stent 1000A shown in FIG. 10B. Stent 1000D nonetheless features a suitable stent length $L_D$ and a flared configuration anchoring just above the sinotubular junction 4 and at the base of the aortic root 10 in the expanded condition. Stent 1000D includes an interlocking feature 1080 protruding proximally from each elongated support post 1008 and another interlocking feature protruding distally from each spacer 1070. Referring to FIG. 10F, stent 1000E is substantially similar to stent 1000D illustrated in FIG. 10E, but includes an additional row of distal cells, such as illustrated previously in FIG. 1000A. Stent 1000E may thus have a suitable stent length $L_E$ and a flared configuration for anchoring within the ascending aorta.

FIGS. 11A-11D show several stent designs with different kinds of support post connections. These several types of support post connections reduce the amount of fatigue occurring at the joints connecting the support posts to the remainder of the stent, and provide a desired amount of post flexibility.

Figure 11B:
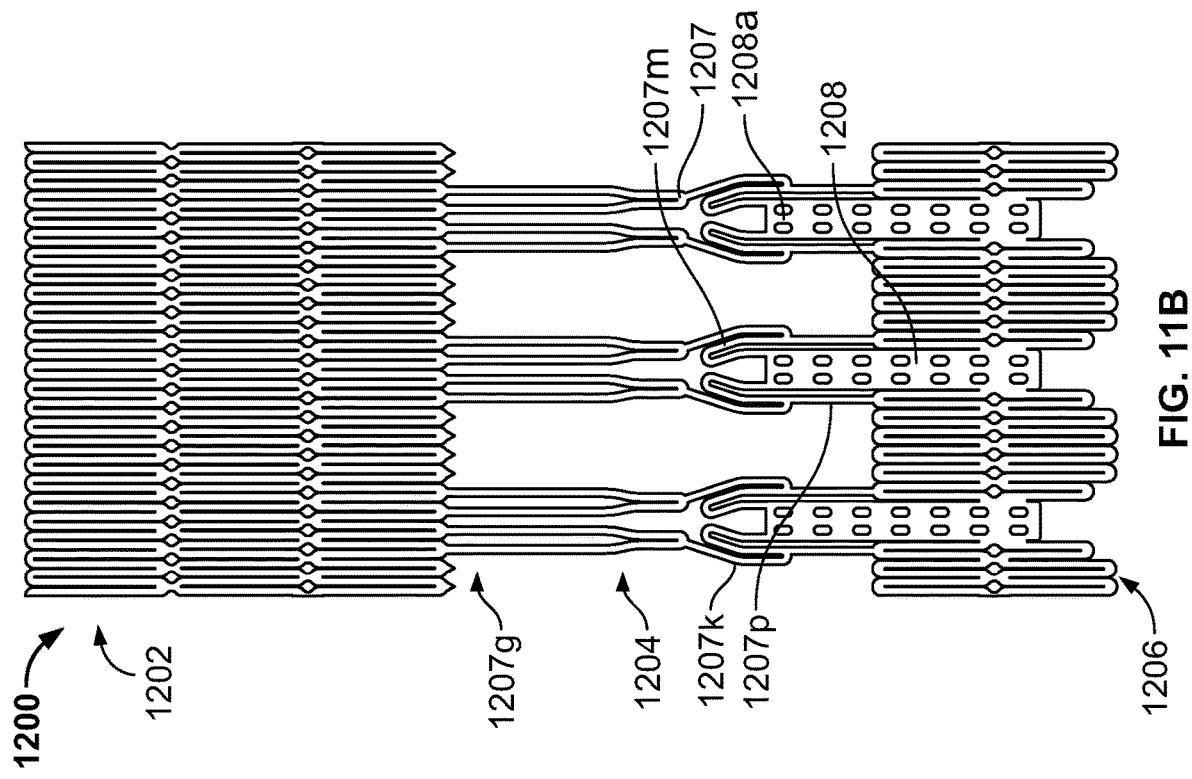
FIG. 11B is a developed view of a stent in an unexpanded condition and including a plurality of posts and a plurality of support strut sets, each set being connected directly to a post and to cells adjacent the post.
Figure 11A:
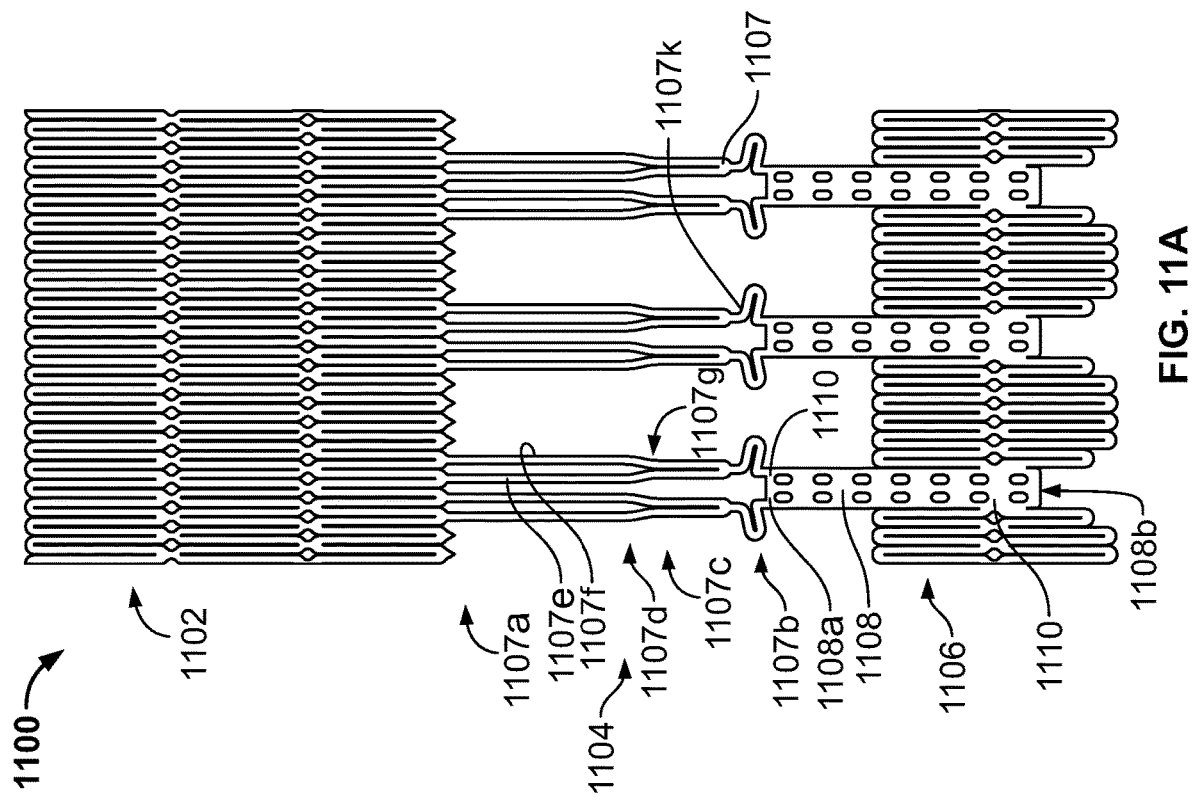
FIG. 11A is a developed view of a stent in an unexpanded condition and including a plurality of posts each connected at one end only to support struts.

Referring specifically to FIG. 11A, stent 1100 is similar to stent 200 of FIG. 3. Stent 1100, however, includes support struts 1107 directly connected to the distal end 1108a of the elongated support post 1108. Specifically, stent 1100 includes support strut arrays 1104 interconnecting distal cells 1102 and elongated support posts 1108. Each support strut array 1104 may include two support struts 1107. Although the drawings show each support strut array 1104 as having two support struts 1107, support strut arrays 1104 may include more or fewer support struts 1107.

Each support strut 1107 has a distal end portion 1107a, a proximal end portion 1107b, and a middle portion 1107c between the distal end portion and the proximal end portion. As seen in FIG. 11A, each support strut 1107 includes a bifurcated section 1107d with a first branch 1107e and a second branch 1107f. Each of the first branch 1107e and the second branch 1107f is connected to a single distal cell 1102. Accordingly, each support strut 1107 is attached to two distal cells 1102. First and second branches 1107e and 1107f are oriented substantially parallel to each other except at a transition or angled region 1107g. At the transition region 1107g, the first branch 1107e and second branch 1107f define an oblique angle relative to one another. In a portion of bifurcated section 1107d located distally to transition region 1107g, the first branch 1107e and second branch 1107f are farther apart from each other than in the portion of bifurcated section 1107d located proximally of transition region 1107g.

The first branch 1107e and second branch 1107f converge into a single support member 1107k at or near the proximal end portion 1107b of each support strut 1107. Each single support member 1107k is coupled to the distal end 1108a of the elongated support post 1108. Single support members 1107k each have a folded configuration, such as a tightly folded C-shape. Post connections 1110 join two single support members 1107k to the opposite sides of the distal end 1108a of the elongated support post 1108. Other post connections 1110 couple two proximal cells 1106 to opposite sides of the elongated support post 1108 near proximal end 1108b.

With reference to FIG. 11B, stent 1200 is substantially similar to stent 1100. Stent 1200 includes distal cells 1202, proximal cells 1206, at least one elongated support post 1208 attached between the proximal cells 1206, and at least one support strut array 1204 coupling the distal cells 1202 to both the elongated support posts 1208 and the proximal cells 1206. Preferably, there is a support strut array 1204 for each elongated support post 1208.

Each support strut array 1204 is similar to support strut array 1104 of stent 1100. For example, each support strut array 1204 includes one or more support struts 1207 with a bifurcated section 1207g and a single support member 1207k. In this embodiment, single support member 1207k is not directly connected to an elongated support member 1208. Rather, each single support member 1207k divides into two arms—a first arm 1207p and a second arm 1207m. First arm 1207p extends proximally from single support member 1207k and is directly connected to a proximal cell 1206 adjacent to elongated support post 1208. Second arm 1207m extends distally from single support member 1207k and may double back upon itself to form an inverted U-shape before directly connecting to the distal end 1208a of the elongated support post 1208.

Figure 11D:
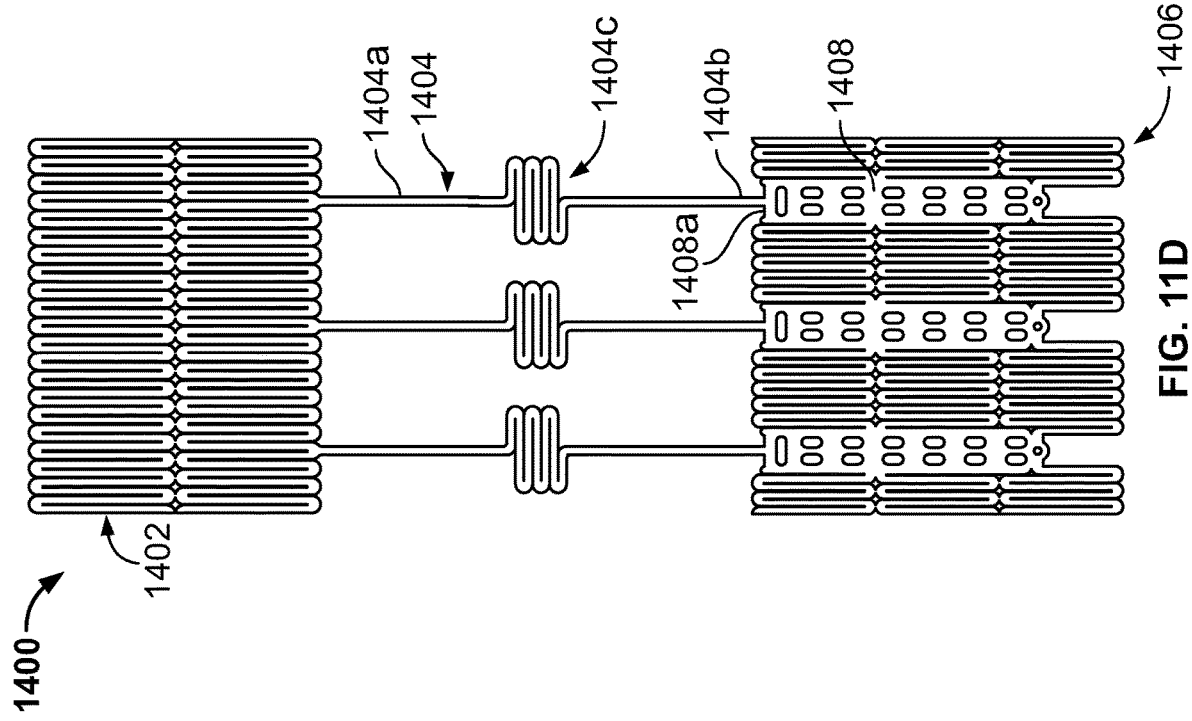
FIG. 11D is a developed view of a stent in an unexpanded condition and including a plurality of posts and a plurality of support struts, each support strut being connected directly to a distal end of a single post.
Figure 11C:
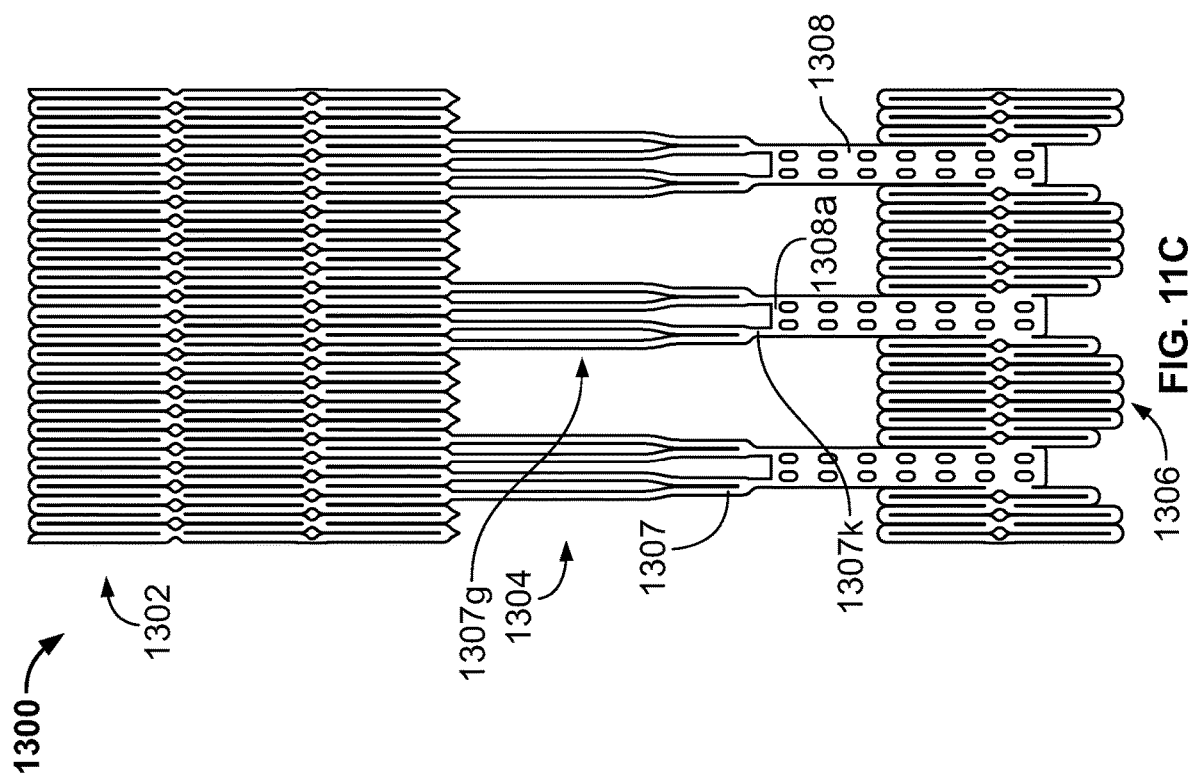
FIG. 11C is a developed view of a stent in an unexpanded condition and including a plurality of posts and a plurality of support strut sets, each support strut set being directly connected to a single post.

With reference to FIG. 11C, stent 1300 is substantially similar to the stent 1100 shown in FIG. 11A. Stent 1300 includes distal cells 1302, proximal cells 1306, at least one elongated support post 1308 attached between the proximal cells 1306, and at least one support strut array 1304 connecting the distal cells 1302 to the elongated support post 1308. Preferably, there is a support strut array 1304 for each elongated support post 1308. Each support strut array 1304 includes one or more support struts 1307. In the embodiment illustrated in FIG. 11C, each support strut array 1304 includes two support struts 1307. In any event, each support strut 1307 has a bifurcated section 1307g connected to distal cells 1302 and a single support member 1307k attached to the distal end 1308a of the elongated support post 1308. Bifurcated section 1307g of each support strut 1307 has two branches, each of which connects to a single distal cell 1302. Single support member 1307k connects directly to the distal end 1308a of the elongated support post 1308 and is substantially shorter in length than the bifurcated section 1307g. The single support members 1307k of two support struts 1307 may be connected to opposite sides of the distal end 1308a of the elongated support post 1308.

FIG. 11D illustrates a stent 1400 substantially similar to stent 100 depicted in FIG. 2. Stent 1400, however, includes at least one support strut 1404 with its proximal end 1404b connected to the distal end 1408a of an elongated support post 1408. Preferably, stent 1400 includes a support strut 1404 for each elongated support post 1408. Each support strut 1404 has a distal end 1404a, a proximal end 1404b and a middle portion 1404c between the distal end and the proximal end. The distal end 1404a of each support strut 1404 is connected to a single distal cell 1402. The middle portion 1404c of each support strut 1404 has a sinusoidal or wave shape.

With reference to FIG. 12A, stent 1500 includes a support post 1508 with a shorter post length as compared to the support post lengths of the previously described stents. Shortened support post 1508 has a distal end 1508a and a proximal end 1508b and, during use, reduces the amount of space taken up by the stent and valve material when in the unexpanded condition. The design of stent 1500 allows for a strong structural anchoring of the valve leaflets V at the distal end 1508a of the shortened support post 1508. As seen in FIG. 12A, leaflets V gradually taper away from shortened support post 1508. Since leaflet V is not connected all the way to the proximal end 1508b of the post 1508, a reduced amount of leaflet material engages stent 1500, permitting stent 1500 to be crimped down to a smaller diameter.

Two post connections 1510 couple two proximal cells 1506 to opposite sides of the distal end 1508a of the shortened support post 1508. Another post connection 1510 joins a single central point of the proximal end 1508b of the shortened support post 1508 to two additional proximal cells 1506. There is no stent material proximally of the post connection 1510 at the proximal end 1508b of shortened post 1508. Indeed, stent 1500 has a gap 1590 defined between the proximal cells 1506 positioned proximally of the proximal end 1508b of the shortened support post 1508. Accordingly, stent 1500 has a less stiff cantilevered post 1508 and can be flexible even though post 1508 is connected to proximal cells 1506 at both its distal end 1508a and its proximal end 1508b.

Stent 1500 may alternatively incorporate a full-length or elongated support post 1509 as shown in FIG. 12B. Elongated support post 1509 is longer and narrower than shortened support post 1508 and includes reduced width portion 1509d. Reduced width portion 1509d is located near the proximal end 1509b of the elongated support post 1509 and allows stent 1500 to be more compactly crimped. The overall reduced width of elongated support post 1509 also allows a user to secure the knots connecting a valve to elongated support post 1509 away from the cells. In addition to the reduced width portion 1509d, elongated support post 1509 includes eyelets or apertures 1532 and a base portion 1509e. Eyelets 1532 extend from the distal end 1509a of elongated support post 1509 along the section located distally of the reduced width portion 1509d. Reduced width portion 1509d and base portion 1509e do not have eyelets 1532. Base portion 1509e is wider than reduced width portion 1509d and may have a rectangular or paddle shape. In use, base portion 1509e may function as an interlocking feature configured to be attached to a delivery system or another valve.

Referring to FIG. 12C, stent 1500 may alternatively incorporate elongated support post 1511, which is substantially similar to elongated support post 1509. Elongated support post 1511 is narrower than both the shortened support post 1508 of FIG. 12A and the elongated support post 1509 of FIG. 12B, thus enabling an even smaller overall diameter when crimped. In addition, elongated support post 1511 has a reduced width portion 1511d, a base portion 1511e and a plurality of merged eyelets 1533. Merged eyelets 1533 constitute two eyelets 1532 as shown in FIG. 12B merged together. Eyelets 1533 are larger than eyelets 1532 of FIG. 12A, thus making elongated support post 1511 more flexible than elongated support post 1509. Base portion 1511e can function as an interlocking feature configured to be attached to a delivery system or another valve.

With reference to FIGS. 13A and 13B, a stent 1600 includes a plurality of cells 1602 and an elongated support post 1608. Some of these cells 1602 are connected to the elongated support post 1608 via post connections 1610. One group of post connections 1610 couple two cells 1602 to opposite sides of the distal end 1608a of the elongated support post 1608. Another group of post connections 1610 join two other cells 1602 to opposite sides of the proximal end 1608b of the elongated support post 1608.

Ordinarily, because of the fixed length of elongated support post 1608, the cells 1602 immediately adjacent to the support post would not be able to expand away from the support post to create a space therebetween. To overcome this, however, and provide for the full expansion of stent 1600, elongated support post 1608 may be provided with a sliding mechanism 1660 that enables the length of the elongated support post to shorten upon expansion of stent 1600. Sliding mechanism 1660 includes a central longitudinal slot 1666 which extends distally from the proximal end 1608b of elongated support post 1608, and a finger 1670 adapted for sliding engagement in slot 1666. FIG. 1670 is fixedly connected to a cross-member 1672 positioned proximally of the elongated support post 1608. A pair of concave indentations 1668 on opposite sides of longitudinal slot 1666 can be used to secure a ring, suture, clip, or other structure that may be used as a guide. Upon expansion of stent 1600, finger 1670 is able to slide into slot 1666, thereby allowing elongated support post 1608 to shorten. As a consequence, the cells 1602 immediately adjacent to elongated support post 1608 are able to expand away from the support post. Sliding mechanism 1660 also allows different amounts of post deflection during use of stent 1600 in a prosthetic valve. As seen in FIG. 13B, the leaflet attachments and contour V allow movement of elongated support post 1608 in an area that does not affect the leaflet.

Figure 14B:
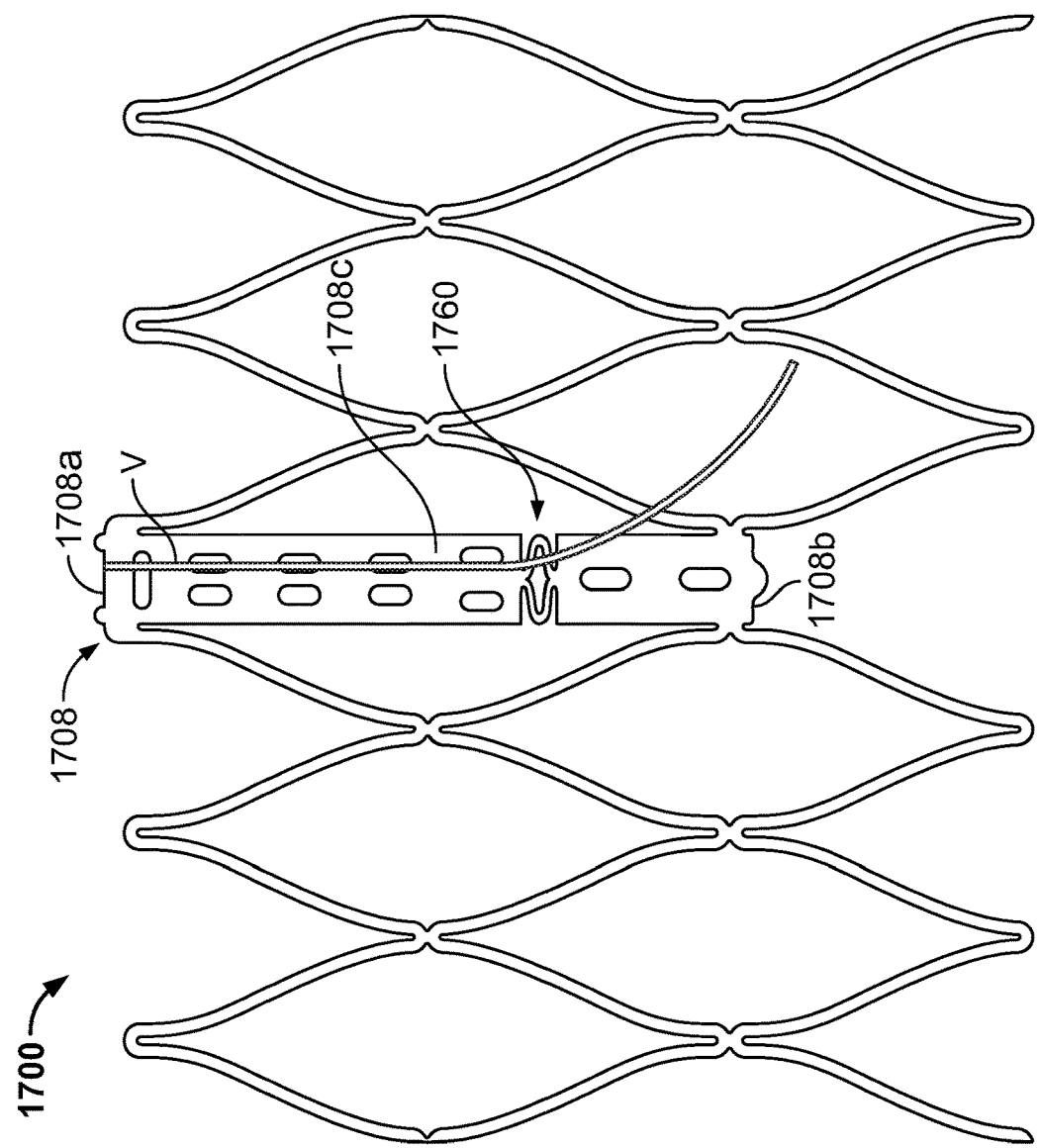
FIG. 14B is a partial developed view of the stent of FIG. 14A in an expanded condition.
Figure 14A:
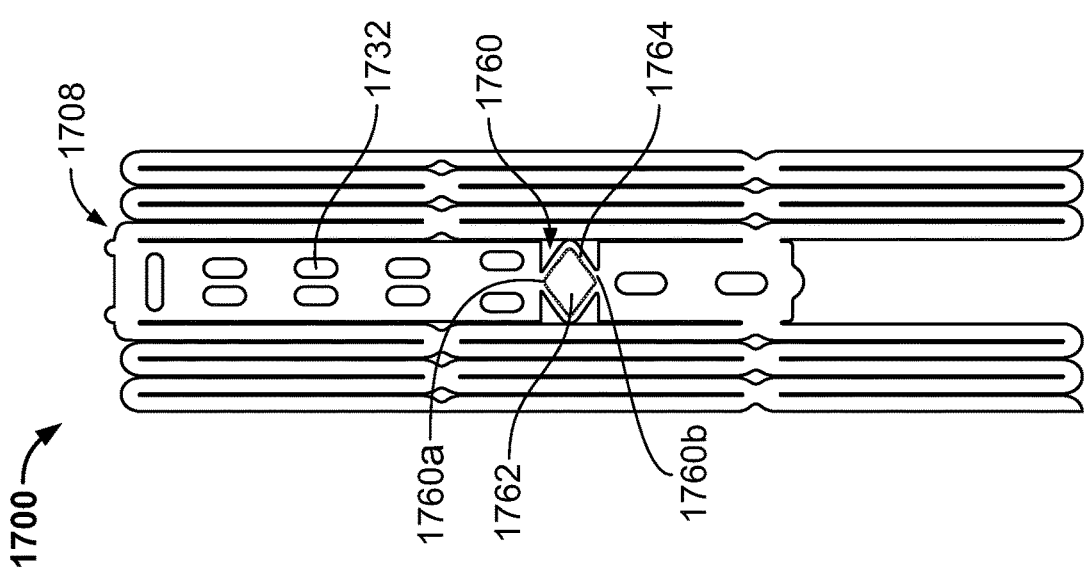
FIG. 14A is a partial developed view of a stent in an unexpanded condition with an elongated support post having a diamond-shaped collapsible post structure.

FIG. 14A shows a stent 1700 in a flat, rolled out, unexpanded condition and FIG. 14B illustrates stent 1700 in a flat, rolled out, expanded condition. Stent 1700 is substantially similar to stent 1600 but does not include a sliding mechanism. Instead, stent 1700 includes an elongated support post 1708 having a collapsible feature 1760 which enables the length of the support post to shorten upon expansion of the stent. As with previous embodiments, elongated support post 1708 has a distal end 1708a, a proximal end 1708b, and a middle 1708c. In addition, elongated support post 1708 includes eyelets or apertures 1732. As shown in FIG. 14B, since the leaflet attachments of valve V only need the eyelets 1732 positioned near the distal end 1708a of elongated support post 1708, collapsible feature 1760 may be located between the middle 1708c and the proximal end 1708b of the elongated support post. Nevertheless, collapsible feature 1760 may be positioned at any suitable location along the length of elongated support post 1708. Irrespective of its position, collapsible feature 1760 enables elongated support post 1708 to shorten axially during expansion of stent 1700, as shown in FIGS. 14A and 14B.

Collapsible feature 1760 may have a first end 1760a and a second end 1760b. The first end 1760a of the collapsible feature 1760 may be connected to a portion of the elongated support post 1708 close to its middle 1708c, while the second end 1760b of the collapsible feature may be connected to a portion of the elongated support post 1708 near its proximal end 1708b. Collapsible feature 1760 may have a plurality of legs 1764 arranged substantially in a diamond shape between its first end 1760a and its second end 1760b, with a central opening 1762 defined in the interior of legs 1764. Legs 1764 may be formed from a flexible or bendable material that can readily deform upon the expansion or crimping of stent 1700. The central opening 1762 allows collapsible feature 1760 to collapse when stent 1700 expands or to expand when stent 1700 is collapsed. Consequently, elongated support post 1708 may lengthen or shorten as stent 1700 expands or collapses.

Referring to FIGS. 15A and 15B, stent 1800 is substantially similar to stent 1700 but includes a different kind of collapsible post structure. Stent 1800 includes cells 1802 and an elongated support post 1808 with a collapsible feature 1860. Elongated support post 1808 has a distal end 1808a, a proximal end 1808b and a middle 1808c between the distal end and the proximal end. Collapsible feature 1860 may be located between the middle 1808c and the proximal end 1808b of the elongated support post 1808 and may include a first collapsible member 1862 having a serpentine or sinusoidal shape and a second collapsible member 1864 having a similar serpentine or sinusoidal shape, with a central opening 1866 defined between them. As shown in FIGS. 15A and 15B, collapsible members 1862 and 1864 are flexible and therefore can freely move between an expanded condition and a collapsed condition. Central opening 1866 facilitates the movement of collapsible members 1862 and 1864 between the expanded and the collapsed conditions. Collapsible members 1862 and 1864 allow elongated support post 1808 to shorten upon expansion of stent 1800. In operation, collapsible feature 1860 axially extends when stent 1800 is collapsed to a smaller diameter, and axially shortens when stent 1800 is expanded to a larger diameter.

Figure 16B:
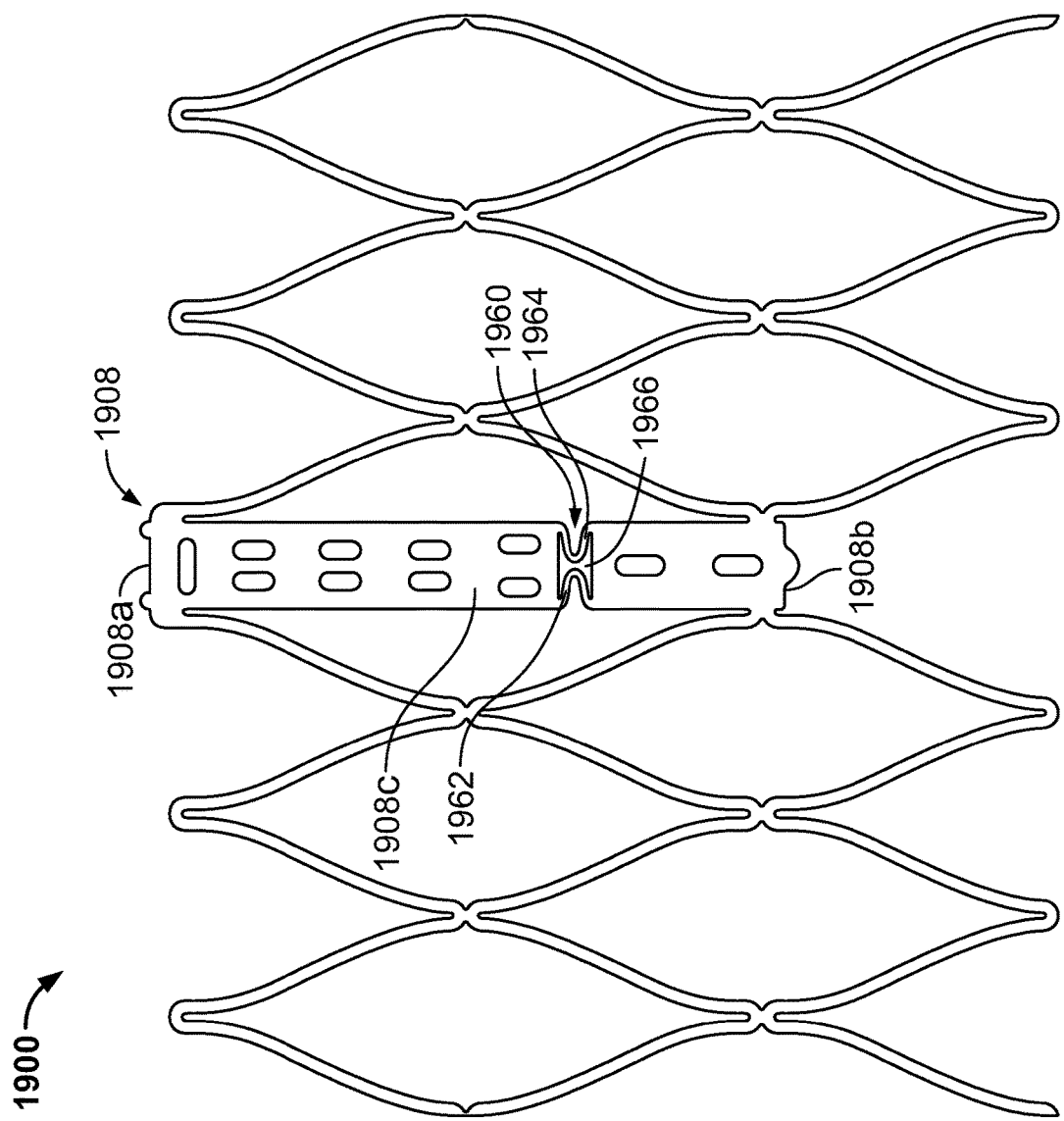
FIG. 16B is a partial developed view of the stent of FIG. 16A in an expanded condition.
Figure 16A:
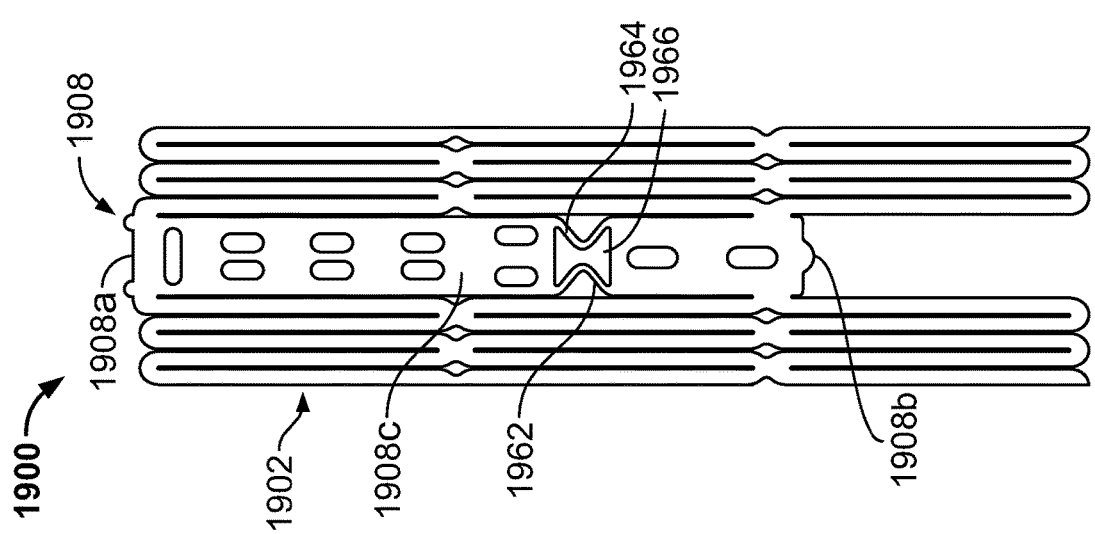
FIG. 16A is a partial developed view of a stent in an unexpanded condition with an elongated support post having an hourglass-shaped collapsible post feature.

With reference to FIGS. 16A and 16B, stent 1900 is substantially similar to stent 1800 shown in FIGS. 15A and 15B, but includes a different kind of collapsible post structure. Stent 1900 includes cells 1902 and an elongated support post 1908 with a collapsible feature 1960. Elongated support post 1908 has a distal end 1908a, a proximal end 1908b, and a middle 1908c between the distal end and the proximal end. The collapsible feature 1960 may be located between the middle 1908c and the proximal end 1908b of the elongated support post 1908. Collapsible feature 1960 may include a first collapsible member 1962 and a second collapsible member 1964, with a central opening 1966 defined between them. Collapsible members 1962 and 1964 are flexible and together may define an hourglass shape. Collapsible feature 1960 may move between a lengthened condition (FIG. 16A) with stent 1900 in an unexpanded state, and a shortened condition (FIG. 16B) with stent 1900 in an expanded state, allowing the elongated support post 1908 to change its length when a stent 1900 is expanded or crimped.

Flexibility of Stent Via Support Strut Connections

The support strut location and type is another primary design parameter that can change the amount of flexibility of the support post. As the support strut is connected farther from the support post, it allows the load from the commissural region during back-pressure to be distributed along the stent body gradually, instead of abruptly at the commissures and struts connected to the stent. This not only decreases the dynamic loading on the valve leaflets, but also reduces strain on the stent. The highest dynamic loads are experienced in the embodiments in which the support struts are connected directly to the support posts (e.g., FIGS. 11A-11D). Embodiments with support strut connections adjacent to the support posts (e.g., FIGS. 3 and 4) experience slightly less dynamic loads, while embodiments with support strut connections located farther from the support posts (e.g., FIGS. 17A and 17B) experience even less dynamic loads. Embodiments with support strut connections located halfway between two adjacent support posts (e.g., FIGS. 5A, 5B and 18A, 18B, and 18C) experience the least dynamic loads.

FIG. 17A shows a stent 2000 in a flat, rolled out, unexpanded condition and FIG. 17B shows a proximal portion of stent 2000 in a flat, rolled out, fully-expanded condition. Stent 2000 generally includes a distal sinusoidal or serpentine pattern of half-cells 2002, proximal cells 2006, support struts 2004 interconnecting distal half-cells 2002 and proximal cells 2006, and elongated support posts 2008 attached to some proximal cells 2006. Stent 2000 may include only half-cells 2002 (not complete cells) to reduce its overall length due to the possibility of aortic arch bend constraints.

Each support strut 2004 has a distal end 2004a connected to a distal half-cell 2002, a proximal end 2004b attached to a proximal cell 2006, and a middle portion 2004c between the distal end and the proximal end. The middle portion 2004c of each support strut 2004 may have a serpentine or sinusoidal shape, as shown in FIG. 17A.

Proximal cells 2006 may be arranged in one or more rows. In the illustrated embodiment, stent 2000 includes a first row 2024 of proximal cells 2006 and a second row 2026 of proximal cells. Some proximal cells 2006 in the first row 2024 and the second row 2026 are attached to an elongated support post 2008. The first row 2024 includes certain proximal cells 2006 which are joined to support struts 2004. The proximal end 2004b of each support strut 2004 is connected to a proximal cell 2006f located one cell beyond the proximal cell 2006 adjacent to the elongated support post 2008.

A plurality of cell connections 2030 may join adjacent proximal cells 2006 in the same row. Proximal cells 2006 in different rows may be joined by sharing common cell segments. Cell connections 2030 may be positioned at the distal end of a proximal cell 2006 in the second row 2026, which is coextensive with a middle portion of an adjacent proximal cell located in the first row 2024. Cell connections 2030 may also be positioned at the proximal end of a proximal cell 2006 in the first row 2024, which is coextensive with the middle portion of an adjacent proximal cell 2006 in the second row 2026. Some proximal cells 2006 in the second row 2026 may be discontinuous in their middle portions, such as through a disconnection or break 2090 at a cell connection 2030, to allow cell expansion in a different way as compared to previous embodiments.

Synergistic Physiological Stent Behavior Via Post Connections

The configuration and connections of the support struts may have an effect on the annulus portion (i.e., proximal cells) of the stent and therefore the valve function. For instance, the annulus section can function virtually independently in the torsional degree-of-freedom when the heart twists relative to the aorta during beating if the support struts are designed and connected to the cells as shown in FIGS. 18A, 18B and 18C.

Figure 18A:
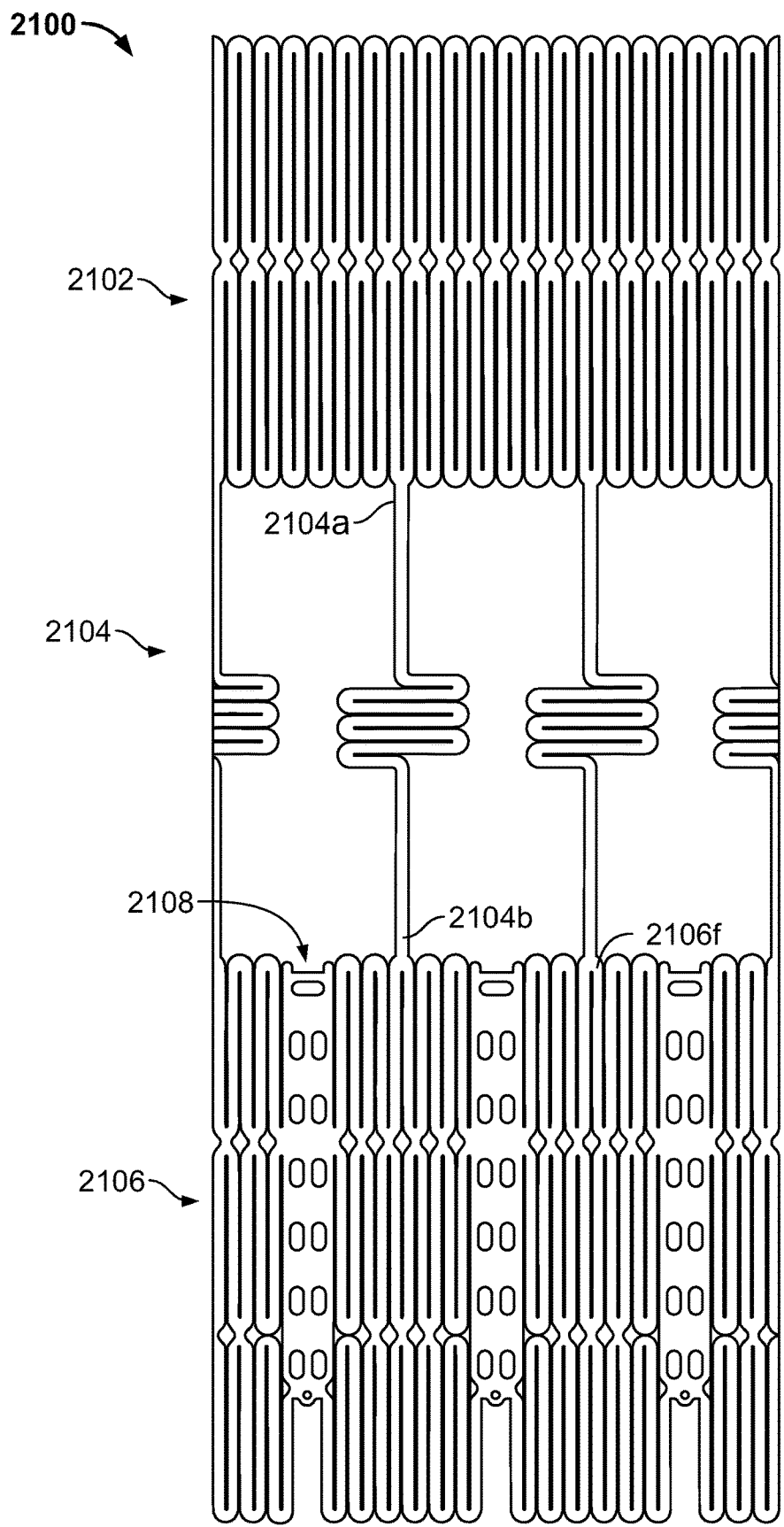
FIG. 18A is a developed view of a stent with a support strut connected to a proximal cell located halfway between two elongated support posts.
Figure 18B:
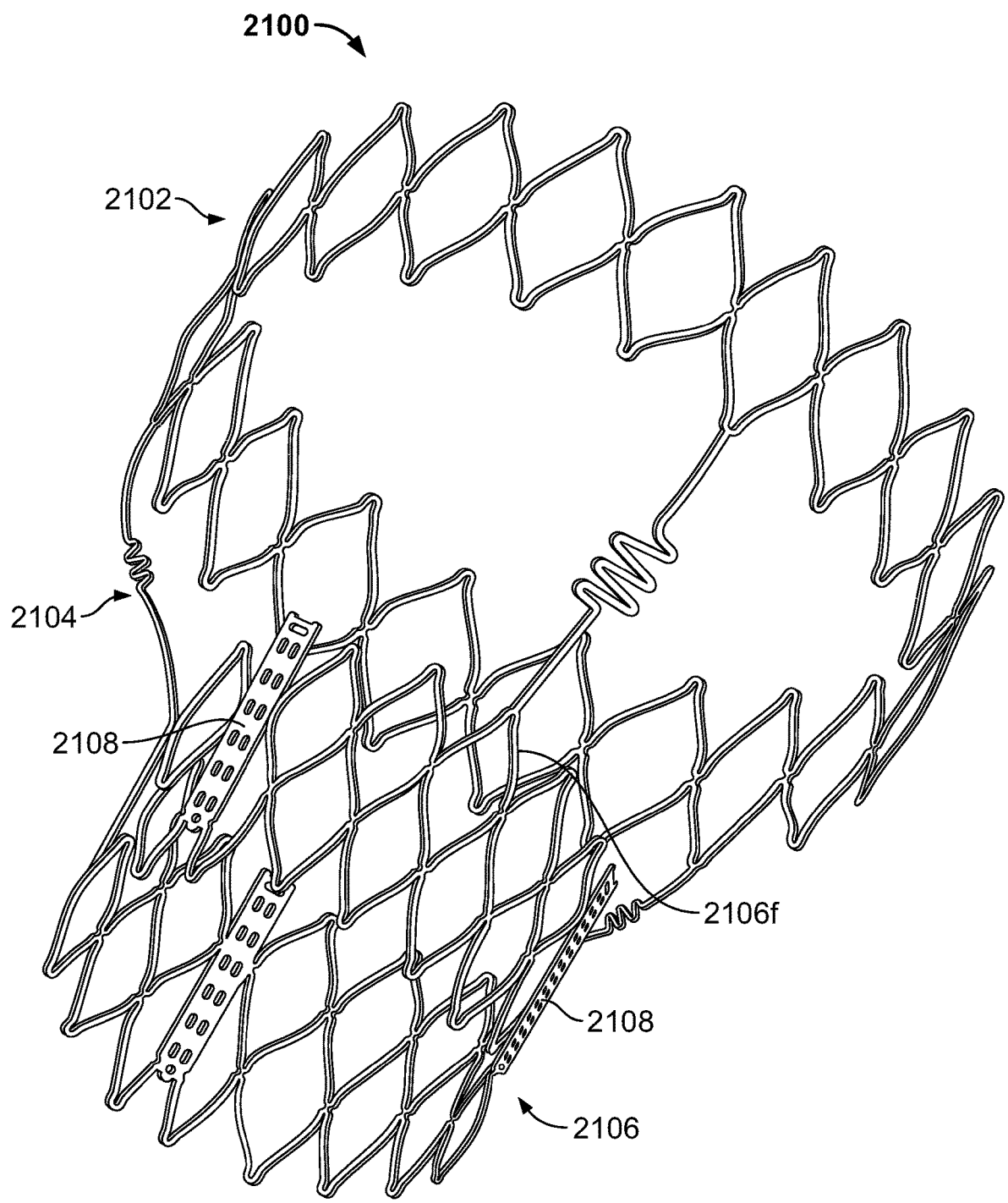
FIG. 18B is a perspective view of the stent of FIG. 18A in an expanded condition.
Figure 18C:
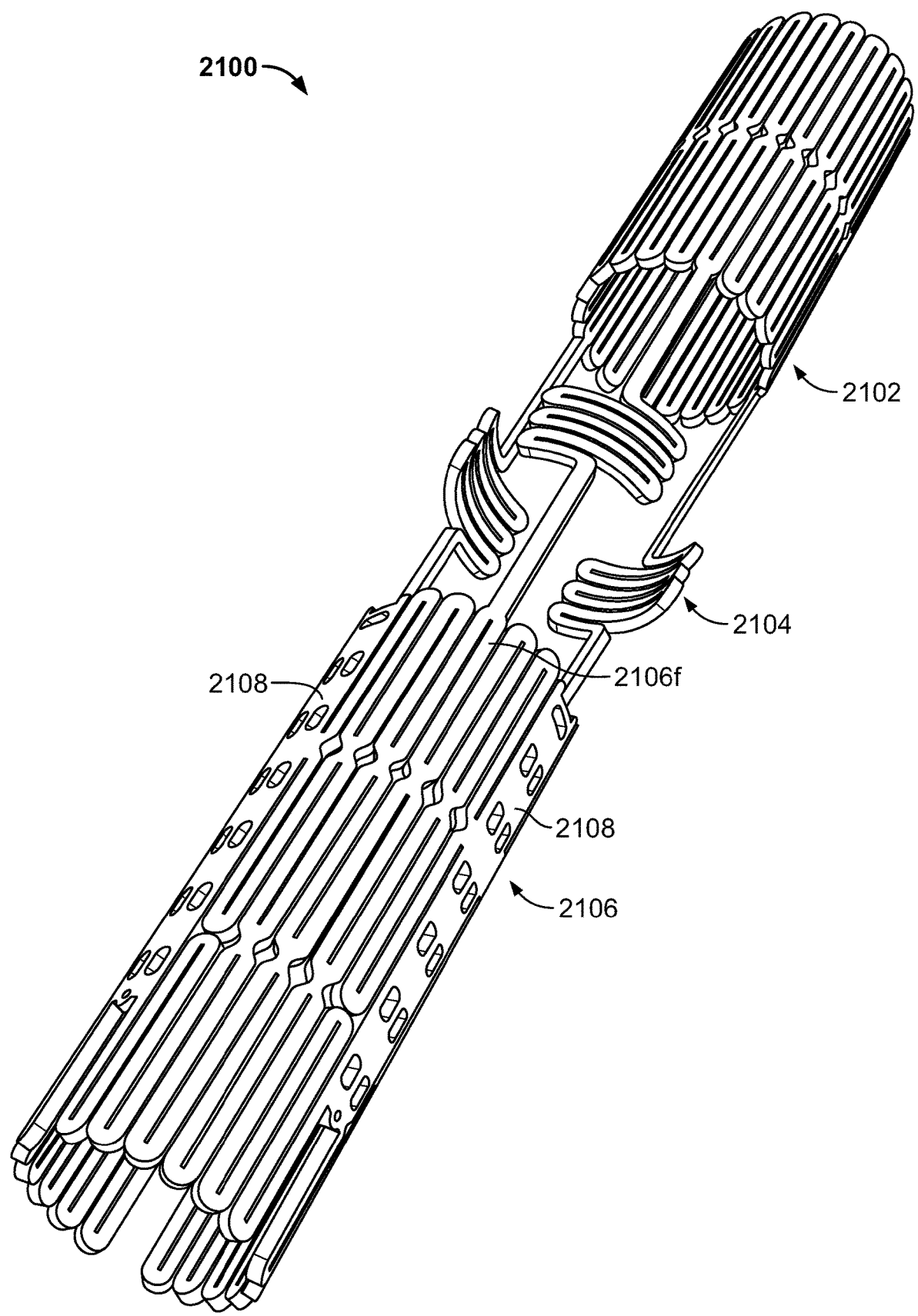
FIG. 18C is a perspective view of the stent of FIG. 18A in an unexpanded condition.

FIGS. 18A, 18B, and 18C show a stent 2100 which is substantially similar to stent 100 shown in FIG. 2. Stent 2100 includes support struts 2104 connected to proximal cells 2106 located midway between two elongated support posts 2108. FIG. 18A illustrates stent 2100 in a flat, rolled out, unexpanded condition; FIG. 18B shows stent 2100 perspectively in a fully expanded and deployed condition; and FIG. 18C depicts stent 2100 perspectively in an unexpanded condition. Stent 2100 generally includes distal cells 2102, proximal cells 2106, support struts 2104 interconnecting distal cells 2102 and proximal cells 2106, and elongated support posts 2108 attached to some proximal cells 2106.

Each support strut 2104 has a distal end 2104a, a proximal end 2104b and a middle portion 2104c between the distal end and the proximal end. The distal end 2104a of each support strut 2104 is connected to a distal cell 2102. The proximal end 2104b of each support strut 2104 is connected to a proximal cell 2106. Specifically, each support strut 2104 is connected to a proximal cell 2106f located midway between two elongated support posts 2108 in order to increase flexibility and minimize the dynamic loads exerted on the elongated support posts. Stent 2100 may include at least three support struts 2104 connected to three proximal cells 2106f, as seen in FIGS. 18A, 18B and 18C, for providing a stable connection of the aorta portion to the annulus portion while providing the greatest amount of stent frame flexibility. Preferably, stent 2100 has the same number of support struts 2104 as elongated support posts 2108.

Figure 19:
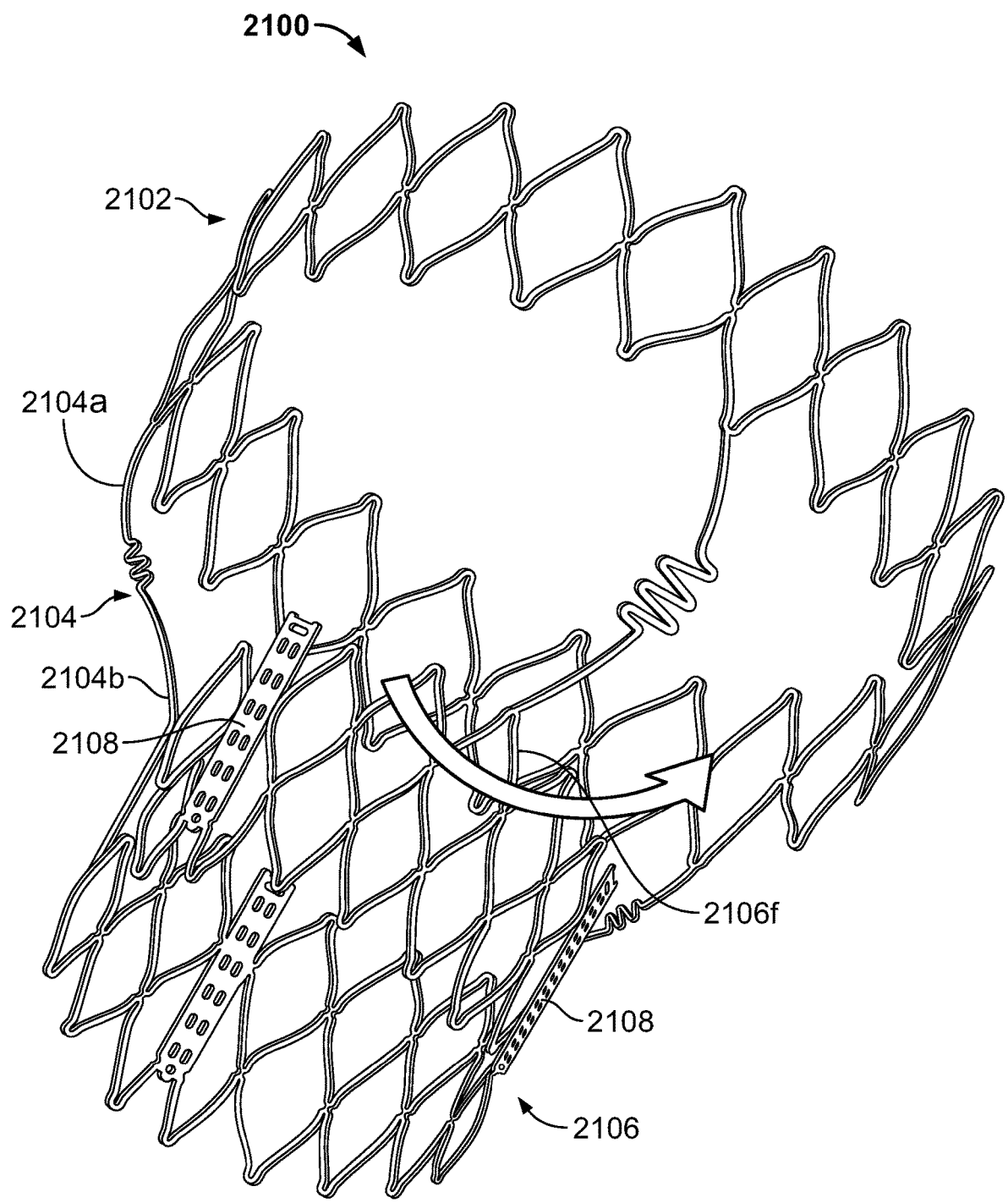
FIG. 19 is a perspective view of the stent of FIG. 18A in an expanded condition and subjected to a torsional force.

FIG. 18B illustrates stent 2100 in a substantially straight configuration as if the heart is not twisting during beating relative to the aorta, and the aortic arch bend is not an issue. FIG. 19 depicts the same stent 2100 with the valve section (i.e., proximal cells 2106) operating relatively free of adverse contortion from the twisting of the heart while still not allowing the stent to migrate.

Figure 20A:
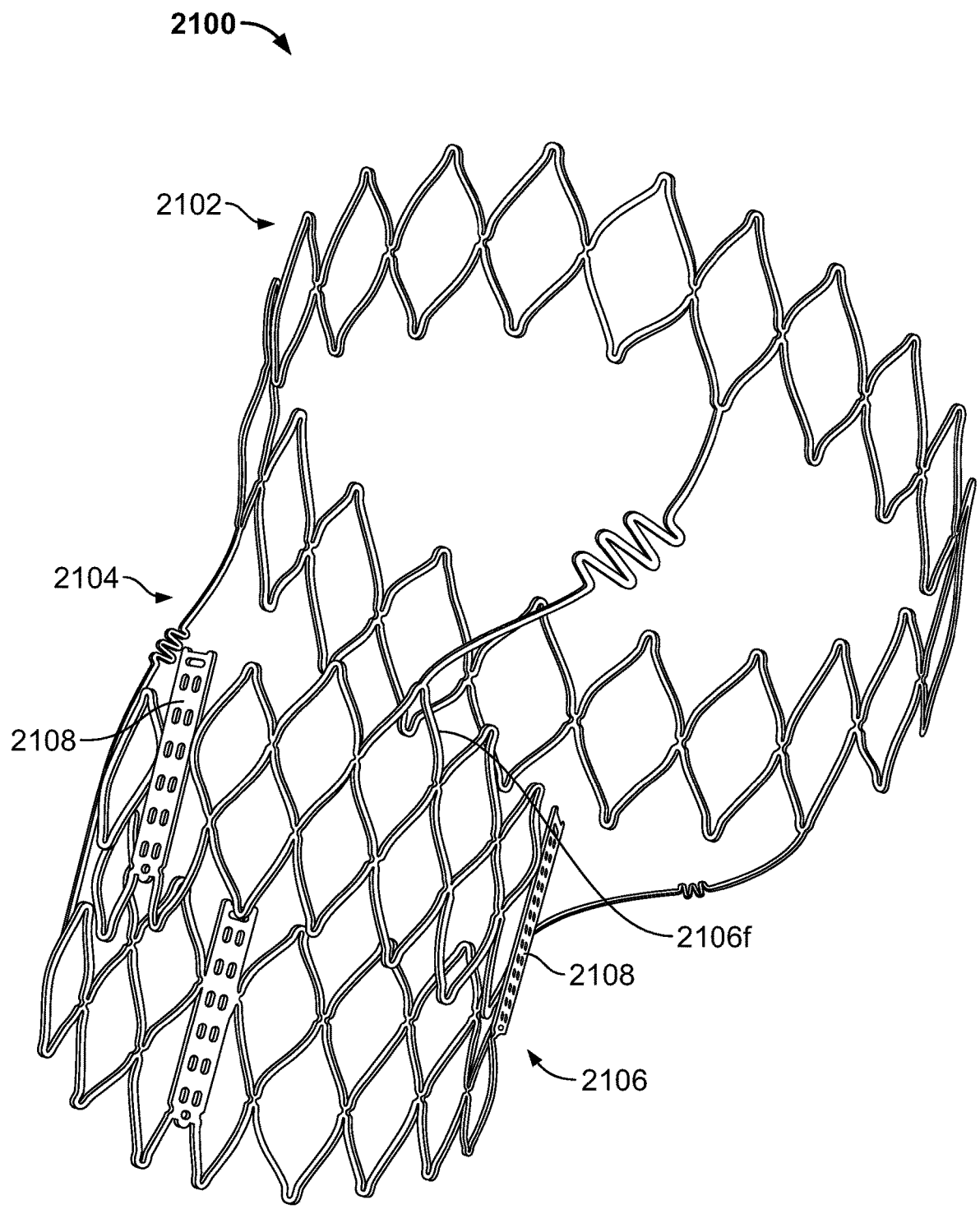
FIG. 20A is a perspective view of the stent of FIG. 18A in an expanded condition and being twisted.
Figure 20B:
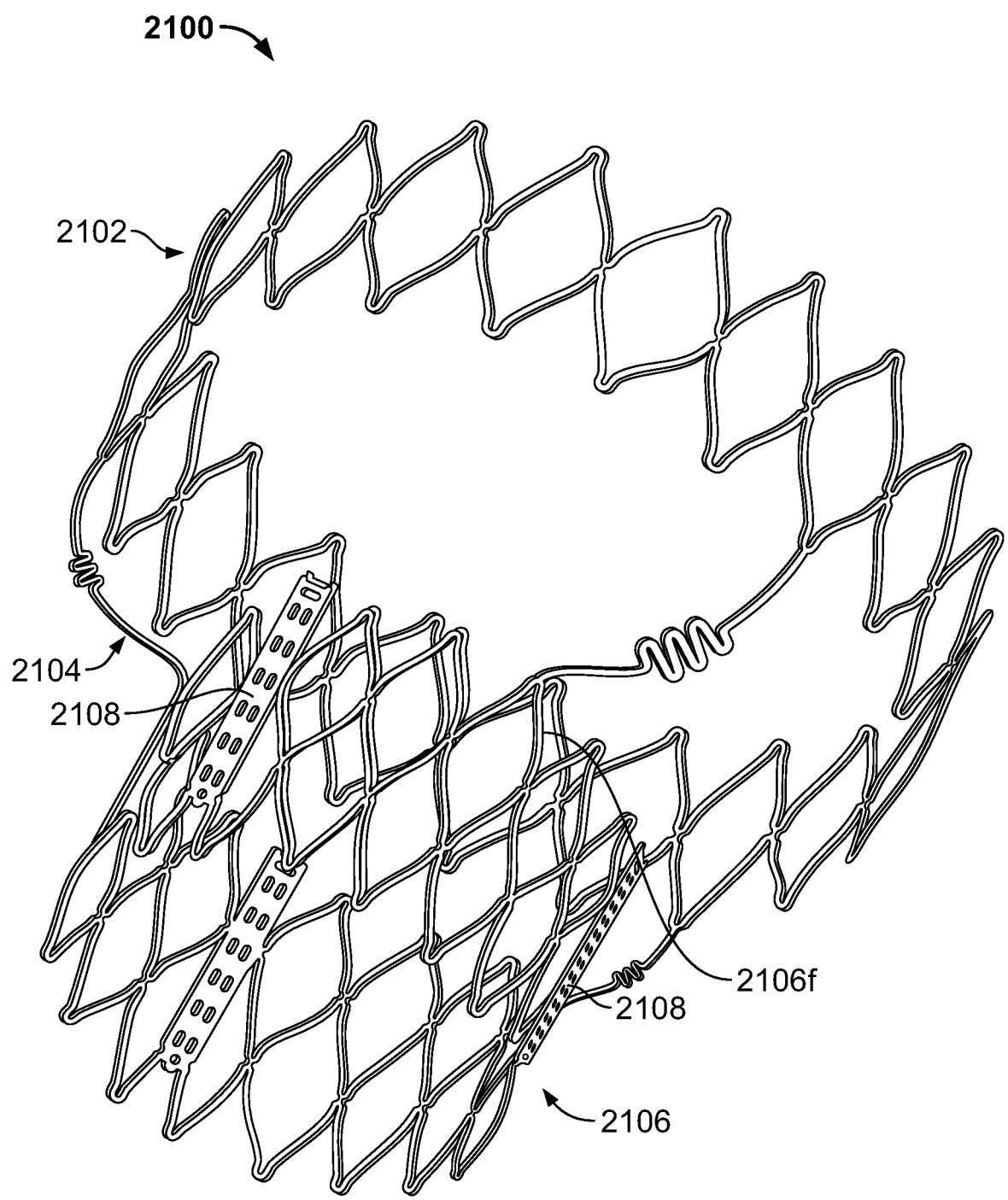
FIG. 20B is a perspective view of the stent of FIG. 18A in an expanded condition and under longitudinal compression.

Additional physiological concerns may arise due to translational (shortening or lengthening) motion and the bending and straightening of the ascending aorta. As seen in FIGS. 20A and 20B, however, the type and locations of the support struts 2104 of stent 2100 also aid in maintaining proper physiological motion, reduce leaflet stress, improve relatively independent valve function, and reduce certain stent strains, all while maintaining the necessary valve anchoring. FIG. 20A illustrates the ability of stent 2100 to conform to an aortic arch bend with little effect on its valve-functioning part (i.e., proximal cells 2106). FIG. 20B shows stent 2100 with the valve section (i.e., proximal cells 2106) functioning relatively free of adverse contortion from shortening and lengthening motions of the relative anatomical structures.

Any of the presently disclosed embodiments of stent may include different kinds of support struts depending on the desired post flexibility and anatomical conformance. See e.g., FIGS. 21A-21J. Each of the support struts illustrated in FIGS. 21A-21J has its own directional advantage. The flexibility of the illustrated support struts aids in the ability to deliver the valve around tortuous vascular anatomy and the aortic arch when collapsed.

Figure 21A:
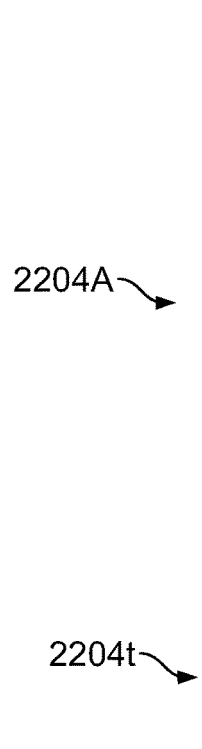
FIG. 21A is a side elevational view of a support strut with a tapered proximal end.
Figure 21B:
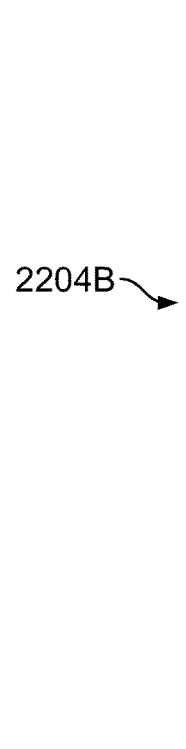
FIG. 21B is a side elevational view of a support strut with a uniform width.
Figure 21C:
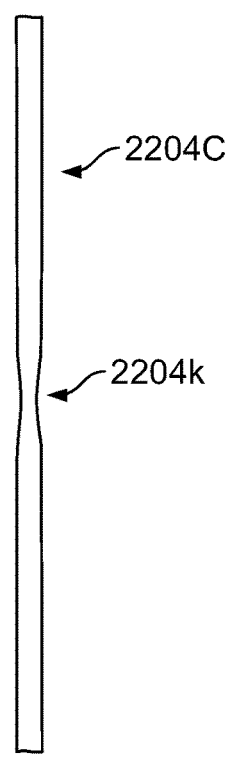
FIG. 21C is a side elevational view of a support strut with a tapered middle portion.

FIG. 21A shows a support strut 2204A with a tapered proximal portion 2204t. FIG. 21B illustrates a support strut 2204B featuring a uniform diameter or cross-section along its entire length. FIG. 21C depicts a support strut 2204C with a tapered middle portion 2204k. The support struts shown in FIGS. 21A, 21B, and 21C can bend and twist but cannot elongate.

Figure 21D:
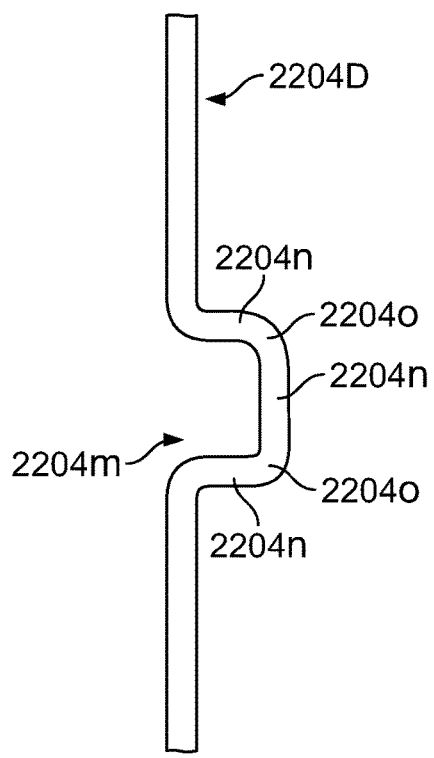
FIG. 21D is a side elevational view of a support strut with an inverted C-shaped middle portion.
Figure 21E:
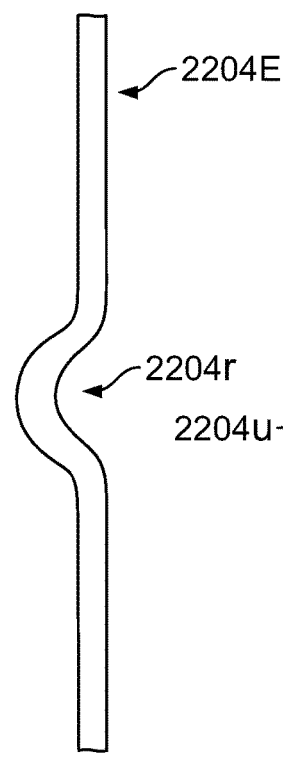
FIG. 21E is a side elevational view of a support strut with a C-shaped middle portion.

FIG. 21D shows a support strut 2204D with a bent middle portion 2204m. Middle portion 2204m has a generally rectangular inverted C-shape with three sides 2204n and two corners 2204o. Two sides 2204n may be oriented substantially parallel to each other and substantially orthogonal to the remainder of strut 2204D, while the third side interconnecting the first two sides may be substantially parallel to the remainder of strut 2204D. Corners 2204o interconnect the different sides 2204n and may be rounded. FIG. 21E illustrates a support strut 2204E with a bent middle portion 2204r. Middle portion 2204r has a generally rounded C-shaped profile. The support struts shown in FIGS. 21D and 21E can bend and twist more than the struts of FIGS. 21A, 21B, and 21C, and can also shorten and elongate.

Figure 21F:
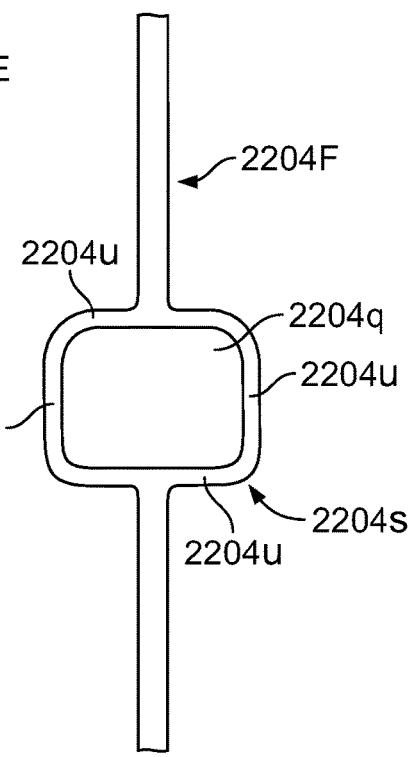
FIG. 21F is a side elevational view of a support strut with a rectangular middle portion.

FIG. 21F shows a support strut 2204F with a rectangular middle portion 2204s. Middle portion 2204s has a substantially rectangular shape and includes four sides 2204u connected to one another and collectively defining a central opening 2204q. Support strut 2204F can bend, twist, shorten and elongate. The middle portion 2204s provides redundant support to strut 2204F.

Figure 21G:
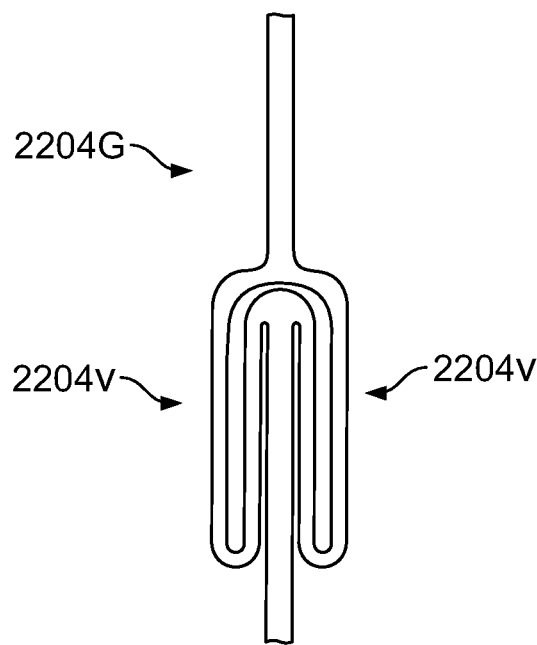
FIG. 21G is a side elevational view of a support strut with nested longitudinal cells.
Figure 21H:
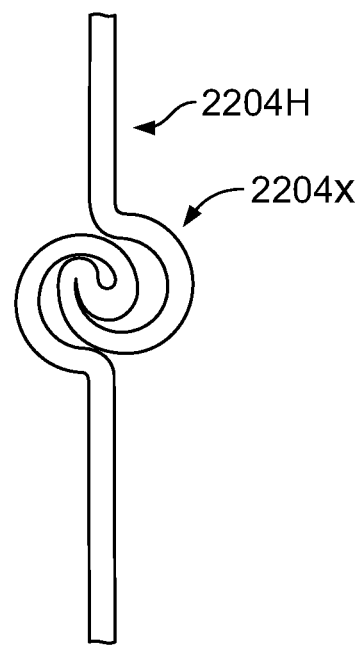
FIG. 21H is a side elevational view of a support strut with a nested coil of cells.

FIG. 21G shows a support strut 2204G with nested longitudinal cells 2204v in its middle portion and extending toward the proximal end of the support strut. Support strut 2204G can bend more easily than previous embodiments, but may have limited elongation capabilities. FIG. 21H shows a support strut 2204H with a nested coil of cells 2204x in its middle portion. The nested coil of cells 2204x can bend, twist and elongate via a circular nested mechanism.

Figure 21I:
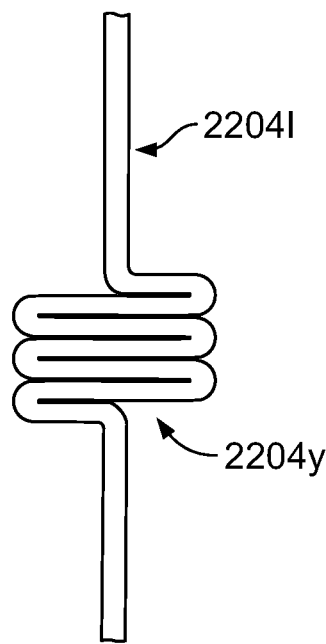
FIG. 21I is a side elevational view of a support strut with a sinusoidal-shaped middle portion.
Figure 21J:
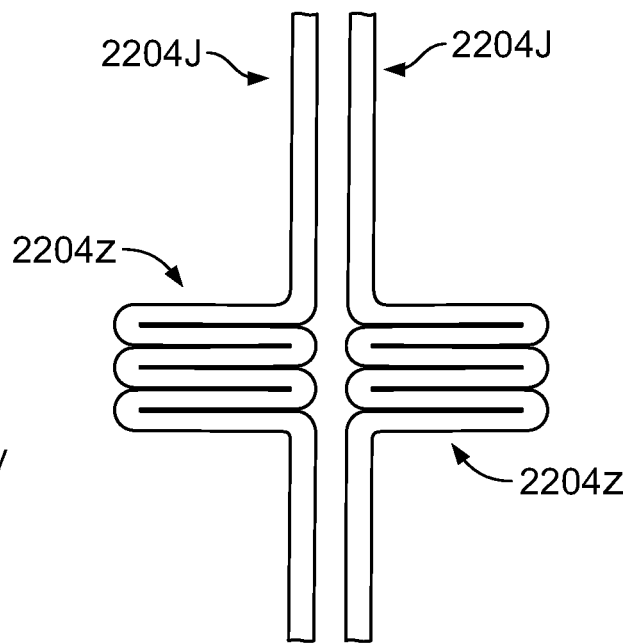
FIG. 21J is a side elevational view of a pair of support struts with offset sinusoidal-shaped middle portions.

FIG. 21I illustrates a support strut 2204I with a single serpentine or sinusoidal link 2204y in its middle portion. Support strut 2204I can bend and twist and can also elongate more easily than previous embodiments. FIG. 21J shows a pair of support struts 2204J each having serpentine-shaped links 2204z in their middle portions. The serpentine-shaped link 2204z of one support strut 2204J is offset to the left (or away from the other support strut 2204J), while the serpentine-shaped link 2204z of the other support strut 2204J is offset to the right (or away from the other support strut 2204J).

Flexibility of Stent Post and Anatomical Conformance Via Independent Post Connections Stents may not only have both an annular portion (i.e., proximal cells) and an aortic/sinotubular junction portion (i.e., distal cells), but may alternatively have independently contouring support struts to conform to the differences in anatomy/physiology around the circumference of the aortic root. This can help to anchor the valve with the least amount of unwanted load transfer to the support post area of the valve.

Figure 22:
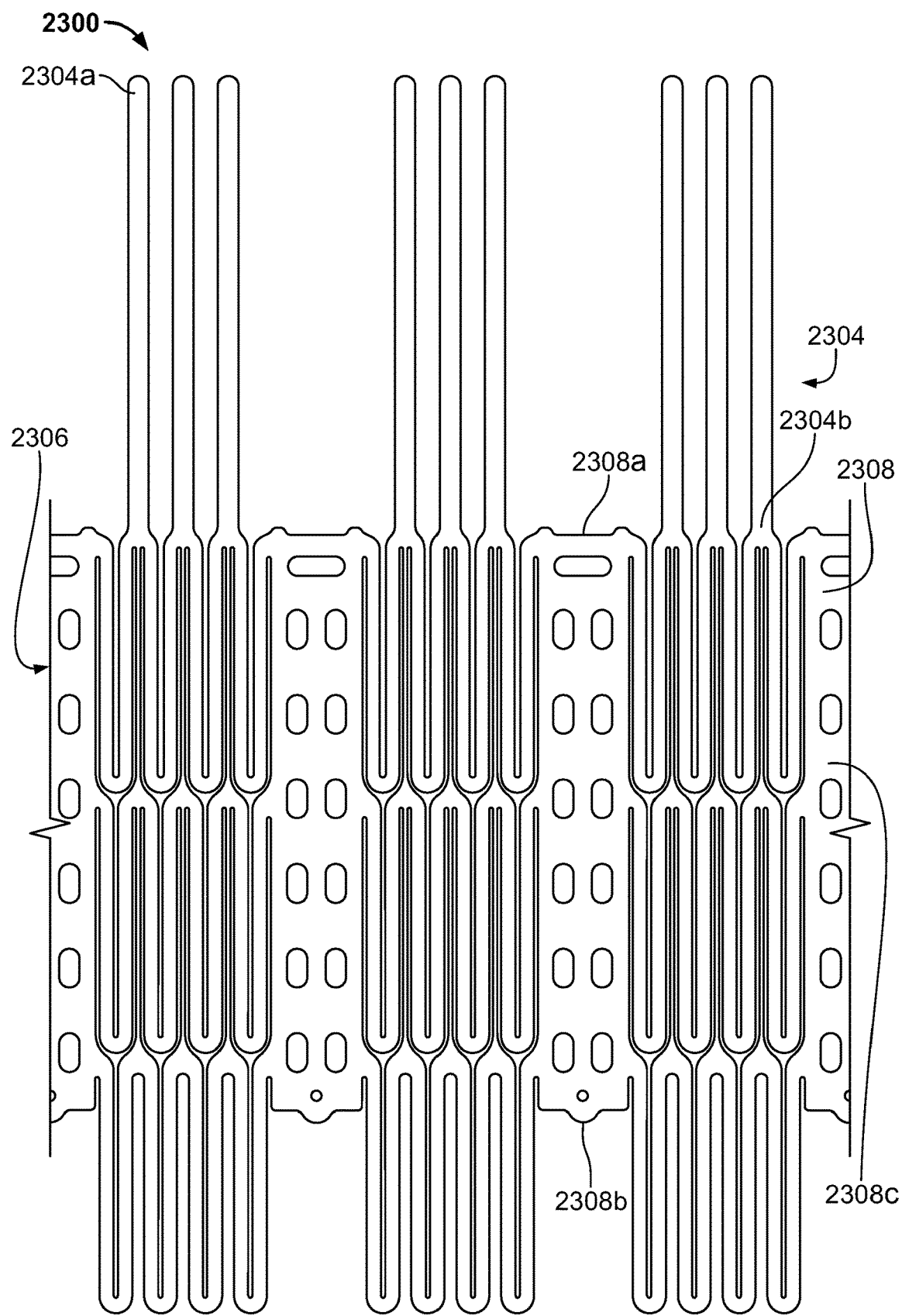
FIG. 22 is a developed view of a stent with support struts cantilevered from proximal cells.

Referring to FIG. 22, stent 2300 generally includes proximal cells 2306, elongated support posts 2308, and a plurality of support struts 2304 each connected at a proximal end 2304b to a proximal cell 2306, and extending distally therefrom in a cantilevered fashion to a free distal end 2304a. Each elongated support post 2308 is attached at its distal end 2308a, proximal end 2308b and middle 2308c to some of cells 2306. Each support strut 2304 is free to move independently and to contour to the anatomy/physiology of the patient's aortic root. Since the support struts 2304 can be independently contoured to the anatomy, the distal end 2304a of each support strut 2304 can anchor in the aorta, above and/or below the sinotubular junction, around the free edge of the valve leaflets. Stent 2300 does not have distal cells. The absence of distal cells provides stent 2300 with greater post flexibility while still providing additional anchoring capabilities. Although FIG. 22 shows support struts 2304 with a substantially straight configuration, this preferably is prior to final processing to provide the support struts with desired configurations.

FIGS. 23A and 23B show some different configurations which cantilevered support struts 2304 may have. In the interest of simplicity, FIGS. 23A and 23B show the valve portion of the stent (e.g., proximal cells and elongated support posts) as a ring. This ring, however, does not really exist and merely illustrates that the support struts 2304 are held in place by other structures of the stent. In the embodiments shown in FIGS. 23A and 23B, each support strut 2304 has a proximal end 2304b attached to proximal cell or an elongated support post (not shown) and a free distal end 2304a. However, the distal ends 2304a of the support struts 2304 of these two embodiments have different configurations.

In the embodiment shown in FIG. 23A, each support strut 2304 has a curved profile 2304c near its distal end 2304a. The curved profiles 2304c initially bend outwardly or away from one another to anchor just distally of the sinotubular junction, but, closer to the distal ends 2304a, the curved profiles 2304c bend inwardly or toward one another to reduce the possibility of aortic perforation or dissection by a support strut 2304.

In FIG. 23B, the stent includes support struts 2304 designed to seat around and/or just proximal to the sinotubular junction in the distal portion of the sinus. The support struts 2304 of the embodiment shown in FIG. 23B also have a curved profile 2304d near their distal ends 2304a. This curved profile 2304d initially bends outwardly (or away from one another) and then proximally, thereby forming a hook, but, closer to the distal ends 2304a, the curved profile 2304d bends distally.

A single stent 2300 may have the support struts shown in both FIGS. 23A and 23B. Additionally, support struts 2304 may be used to latch onto features of previously implanted prosthetic valves, such as the spacer 770 shown in FIGS. 8A and 8B.

Figure 24:
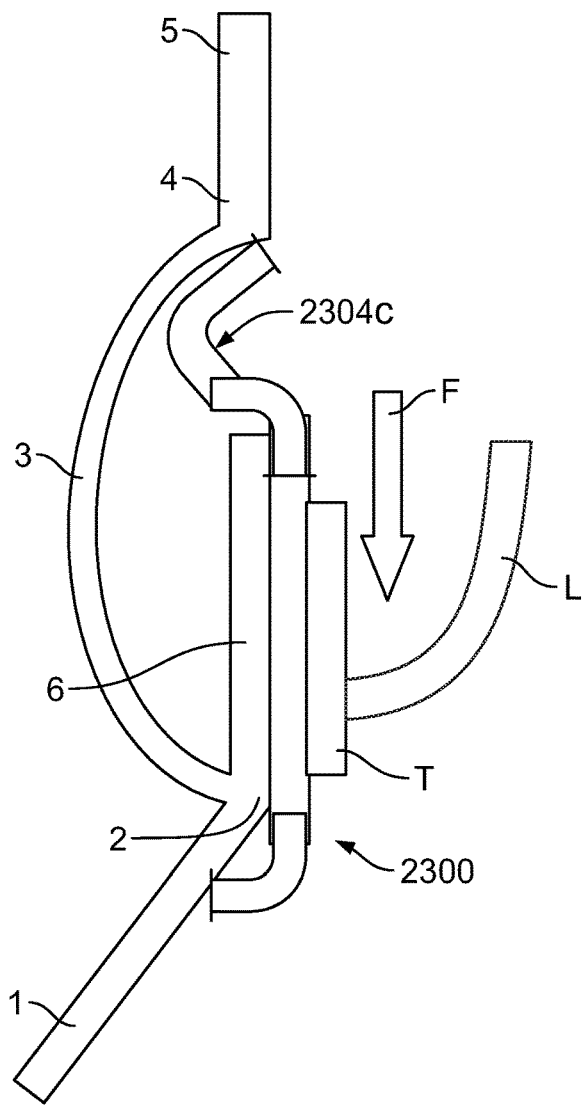
FIG. 24 is a highly schematic, partial longitudinal cross-section showing the stent of FIG. 23A positioned in an aortic annulus.

FIG. 24 shows how the curved profile or anchoring feature 2304c of the support strut 2304 shown in FIG. 23A can be contoured to fasten above the stenotic leaflets or prosthetic valve 6 and below the sinotubular junction 4. The curved profile 2304c of stent 2300 bluntly anchors to the aortic root to minimize migration. The remaining part of stent 2300 is anchored to a stenotic leaflet or prosthetic valve 6 and the annulus 2 of the aortic root. In addition, a fabric and/or tissue layer T may be attached to the interior of the stent 2300, and a leaflet L may be attached to the tissue layer. The tissue layer T and leaflet L function as a valve to prevent backflow, as indicated by arrow F, when in the closed condition.

Figure 25:
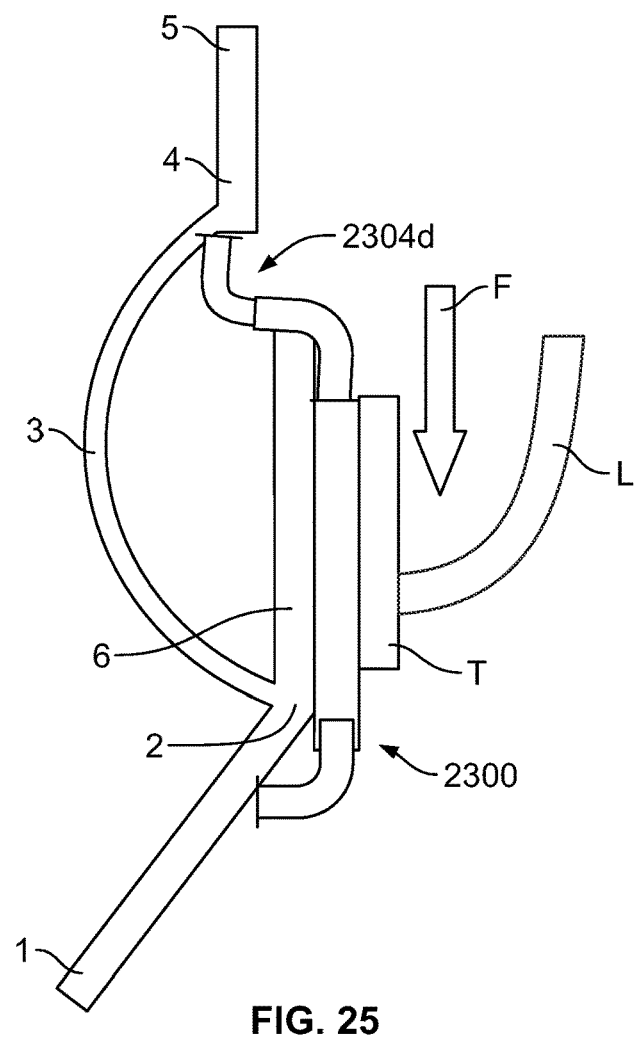
FIG. 25 is a highly schematic, partial longitudinal cross-section showing the stent of FIG. 23B positioned in an aortic annulus.

FIG. 25 shows how the curved profile 2304d of the support strut 2304 shown in FIG. 23B can be contoured to fasten above the stenotic leaflets or prosthetic valve 6 and below the sinotubular junction 4. The curved profile or anchoring feature 2304d of stent 2300 anchors to the aortic root, thereby minimizing migration. As discussed above, a fabric or tissue layer T may be attached to the interior of stent 2300, and a leaflet L may be attached to the tissue layer. The tissue layer T and the leaflet L act as a valve, preventing or least hindering backflow when in the closed condition, as indicated by arrow F.

Leaflet Reinforcement to Reduce Stress at Commissures

As the flexibility of the post and/or stent frame decreases (due to, for example, more connections along the support post), it may be necessary to distribute the greater stress at the commissures. The stress may be distributed to the commissures by, for example, reinforcements at the support posts. The reinforcements may also reduce the possibility of the leaflets hitting the stent frame.

Figure 26:
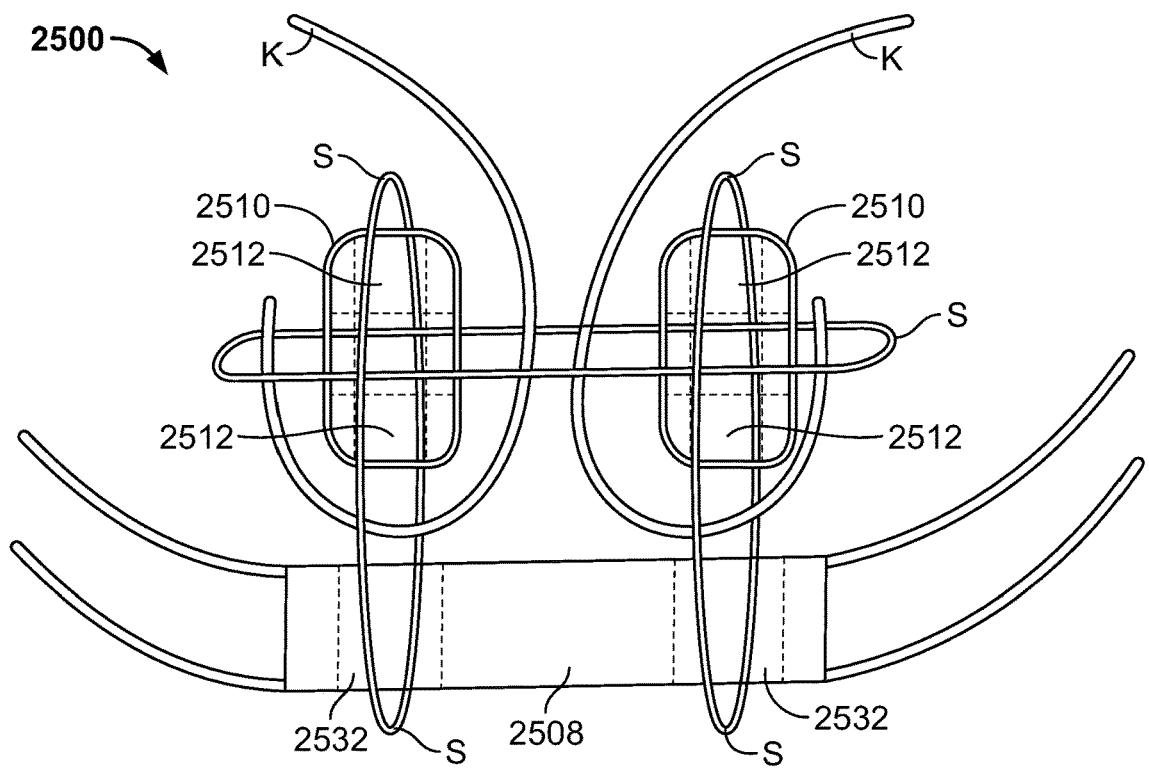
FIG. 26 is a top partial view of a stent reinforced with two secondary posts.

FIG. 26 is a top view of a stent 2500 having a support post 2508 and secondary posts 2510 used for reinforcement. Secondary posts 2510 may be made from a material, such as stainless steel, which is more resistant to fatigue than Nitinol, from which stent 2500 may be made. Support post 2508 has at least two eyelets or apertures 2532. Each secondary post 2512 has two eyelets 2512 oriented substantially perpendicular to each other in a crossing pattern. Secondary posts 2510 may be attached to support post 2508 using sutures S. One suture S passes through one eyelet 2532 of support post 2508 and through a corresponding eyelet 2512 of one secondary post 2510, thereby attaching that secondary post to the support post. Another suture S passes through another eyelet 2532 of support post 2508 and through a corresponding eyelet 2512 of the other secondary post 2510, thereby attaching that secondary post to the support post. Thus, both secondary posts 2510 are attached to support post 2508 with sutures S.

The secondary posts 2510 may also be attached to each other by passing a suture S through an eyelet 2512 of one secondary post 2510 and another eyelet 2512 of the other secondary post 2510. In the embodiment shown in FIG. 26, the secondary posts 2510 sandwich the tissue of the two leaflets K. Leaflets K may be tissue, but this design lends itself to polymer dip coating onto secondary posts 2510 before attaching the resulting subassembly onto strut 2500 via large eyelets at the top and bottom of the support posts.

Figure 27:
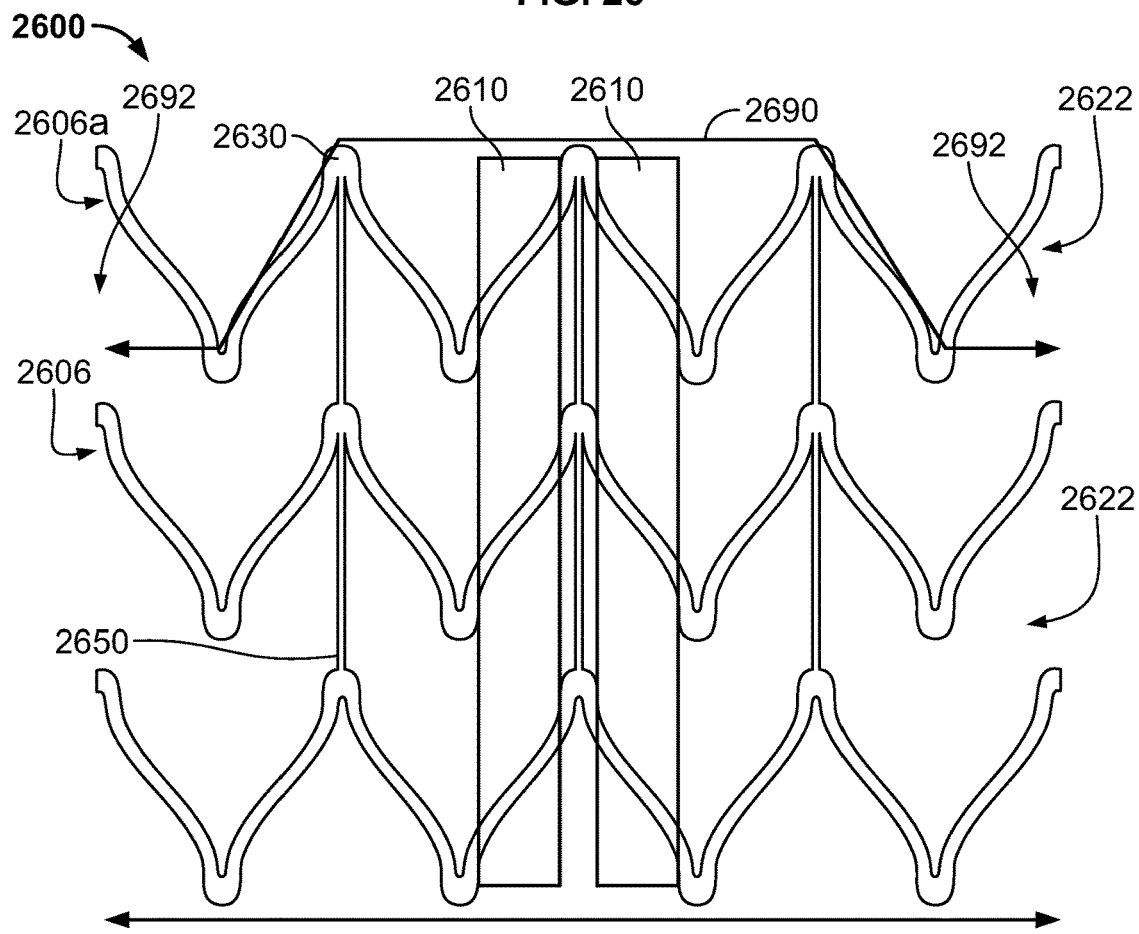
FIG. 27 is a partial developed view of a portion of a stent with a cuff and reinforced with two secondary posts.

The foregoing reinforcement technique may also be used with stents which do not have support posts. FIG. 27 shows one-third of the side of a stent 2600 that does not have support posts. Stent 2600 includes at least two rows of cells 2606, and may include a first row 2622 and a second row 2624 of cells 2606. Cell connections 2630 interconnect adjacent cells 2606 in the same row. Bars 2650 couple cells 2606 positioned in adjacent rows and may be formed of a substantially rigid material. A fabric or tissue cuff 2690 may be attached around the interior or exterior of stent 2600 and cover almost the entirety of the cells 2606, leaving only open areas 2692 for the coronary arteries. Open areas 2692 expose only distal portions 2606a of some cells 2606. Secondary posts 2610 may be sutured to the cuff 2690, to bars 2650 and/or to the segments forming cells 2606.

FIGS. 28A-28F illustrate different reinforcements or secondary posts 2710, 2720, and 2730, which may be attached as rigid structures to any suitable stent as shown in FIG. 26. All secondary posts 2710, 2720, 2730 may have eyelets 2732 along their length for receiving sutures. Eyelets 2732 may also be positioned on multiple sides of each secondary post 2710, 2720, 2730 to allow for multidirectional suturing. The eyelet 2732 closest to the distal end 2702 of the secondary post 2710, 2720, or 2730 may not be spaced apart from the adjacent eyelet 2732 as much as the other eyelets 2732 are spaced apart from each other. Further, the edges of the eyelets 2732 and the edges of the secondary posts 2710, 2720 and 2730 are preferably rounded to eliminate suture and leaflet abrasion.

Each secondary post 2710, 2720, 2730 may have a different shape or cross-section. For example, secondary post 2710 has a substantially circular cross-section, as seen in FIGS. 28A and 28B. Secondary post 2720 may have a substantially rectangular shape or cross-section, as seen in FIGS. 28C and 28D. Secondary post 2730 may have a triangular shape or cross-section, as seen in FIGS. 28E and 28F.

FIGS. 29A and 29B show reinforcements or secondary posts 2810 and 2820 adapted to be attached to a stent as shown in FIG. 26. Posts 2810 and 2820 have a hollow core and may feature a smoothly curved or cylindrical shape. Post 2810 has eyelets 2812 along its length. Eyelets 2812 may have an oblong or elliptical shape. Post 2820 may have two different kinds of eyelets 2822 and 2824. Eyelets 2822 are in the form of alternating through-holes with a substantially oblong or elliptical shape. A partial eyelet 2824 located near the distal end 2820a of post 2820 has a substantially circular shape to hold a suture.

FIG. 30 shows a reinforcement 2900 that may be attached to the stent, as shown in FIG. 26, in lieu of the secondary posts. Reinforcement 2900 includes a first column 2910, a second column 2912, and an arch 2914 interconnecting the first and second columns. First column 2910 has a first end 2910a and a second end 2910b. Second column 2912 has a first end 2912a and a second end 2912b. Arch 2914 connects the first end 2910a of the first column 2910 to the first end 2912a of the second column 2912 and sets the width W between the first and second columns. The first column 2910 and the second column 2912 define a gap 2916 between them. Gap 2916 has a width W and is dimensioned to receive the valve leaflets K (FIG. 26). With leaflets K sandwiched between the first column 2910 and the second column 2912, arch 2914 absorbs the opening load of the leaflets instead of the sutures since columns 2910 and 2912 may want to pull apart.

Figure 31A:
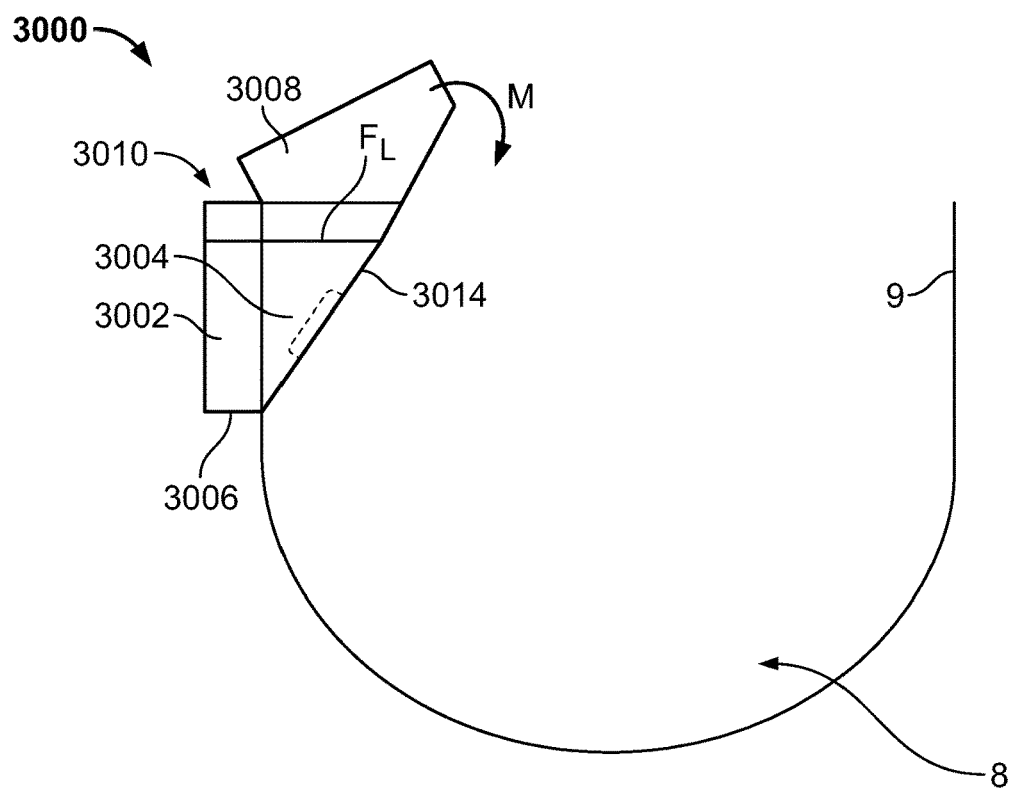
FIG. 31A is a highly schematic, partial longitudinal cross-section showing a reinforcement for use with a stent and adapted to be folded onto itself.
Figure 31B:
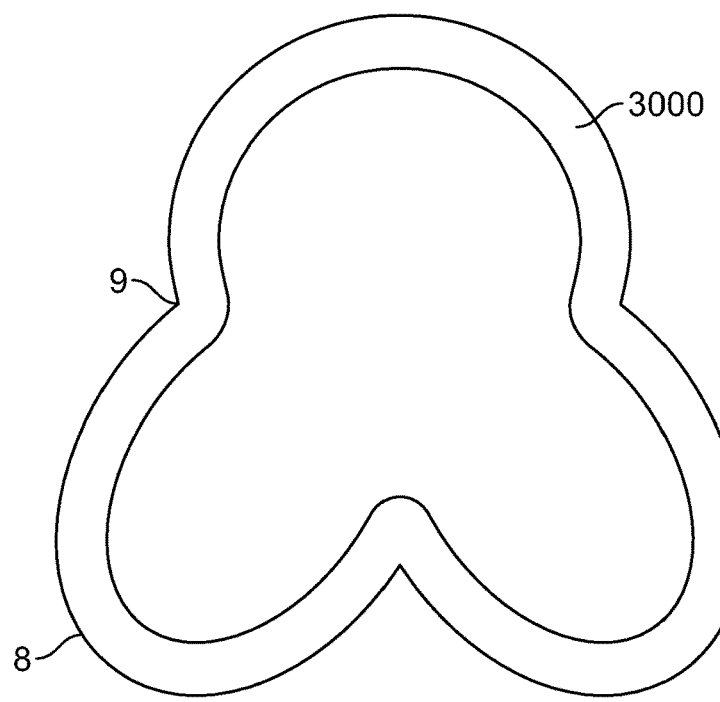
FIG. 31B is a highly schematic top view of the reinforcement of FIG. 31A outlining the entire free end of a leaflet.
Figure 32B:
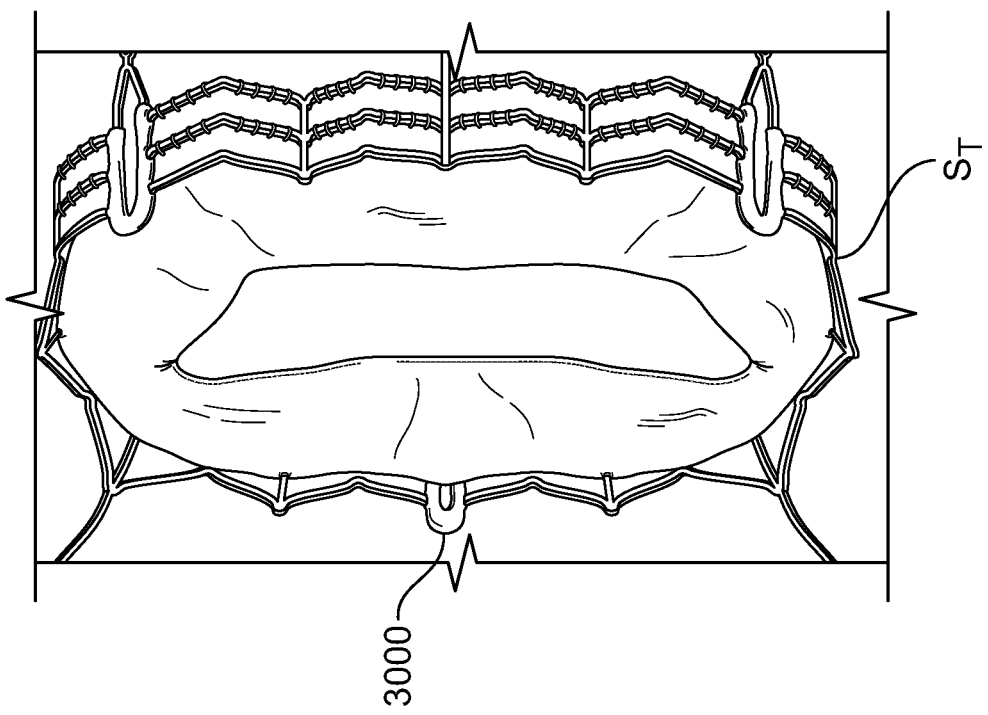
FIG. 32B is a perspective view of a prosthetic valve incorporating the reinforcement of FIG. 31A while the valve is subject to compression.
Figure 32A:
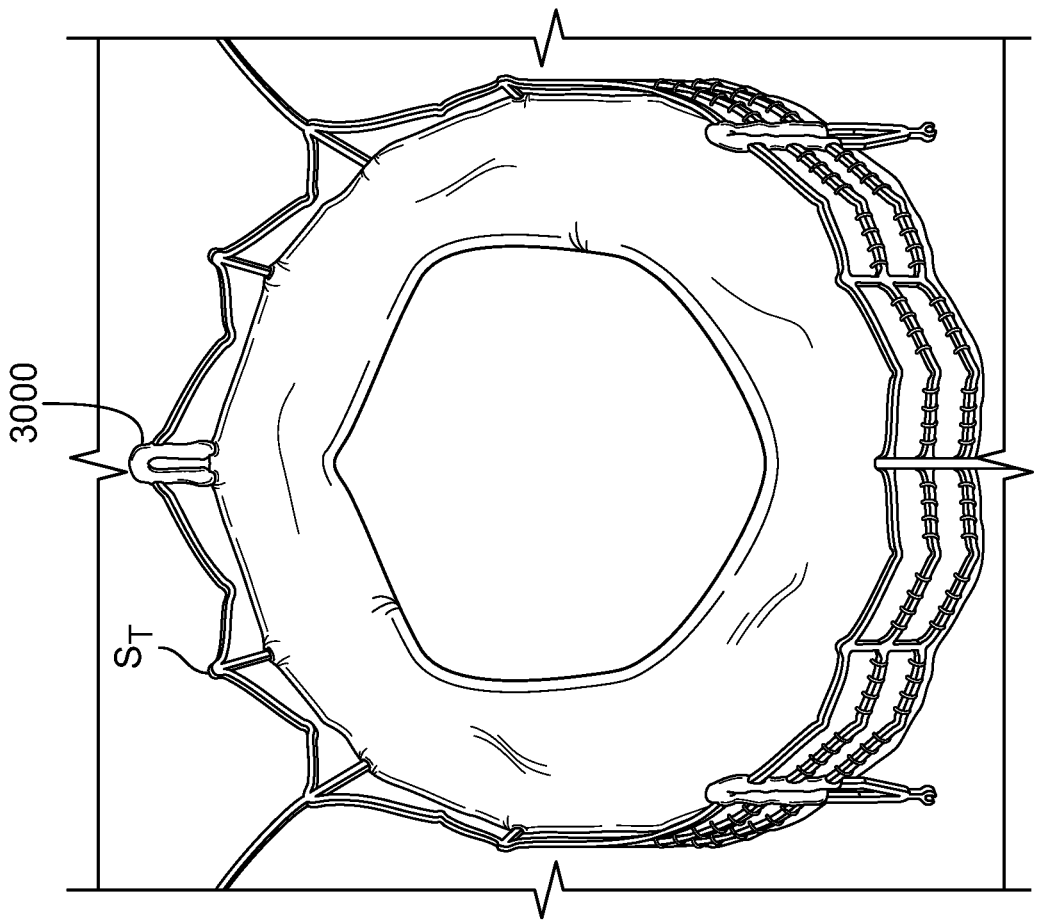
FIG. 32A is a perspective view of a prosthetic valve incorporating the reinforcement of FIG. 31A.
Figure 32C:
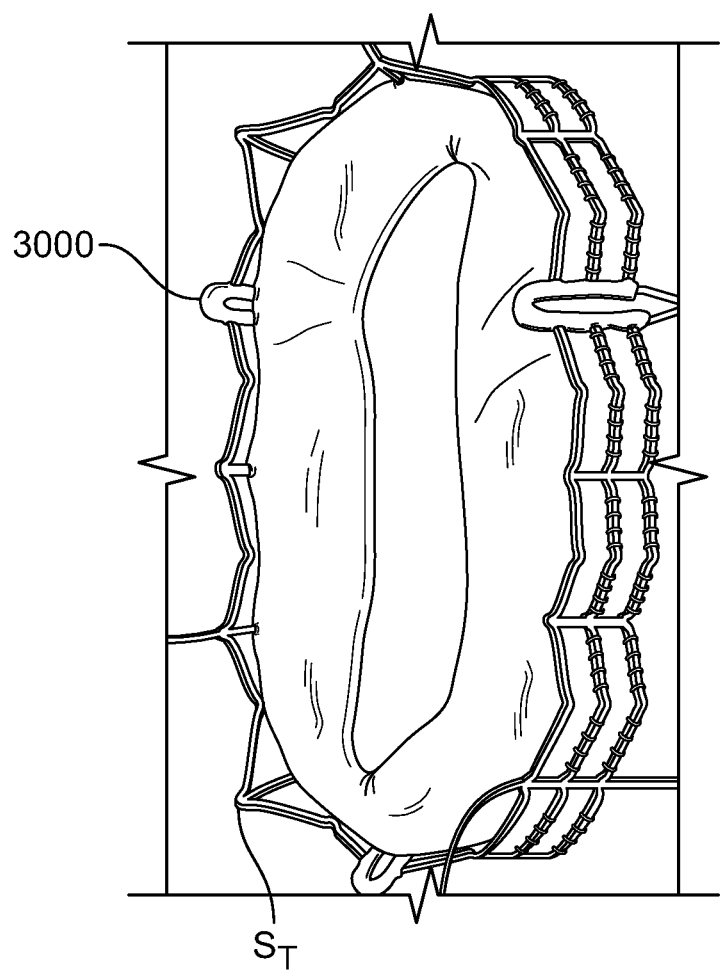
FIG. 32C is a perspective view of a prosthetic valve incorporating the reinforcement of FIG. 31A while the valve is subject to compression.

FIG. 31A shows a pliable reinforcement 3000 folded over a free edge of a leaflet and sutured to itself and to the stent frame or post. In some embodiments, reinforcement 3000 may be attached to a free edge of a leaflet at the commissure 9, but away from the belly region 8 of the valve leaflet, as shown in FIG. 31A. Alternatively, reinforcement 3000 may be attached to the entire sutured edge of the leaflet, which would result in the shape seen in FIG. 31B.

Reinforcement 3000 includes a securing section 3004 and an optional flap 3002 for additional suturing and securement to a support post. As seen in FIG. 31A, reinforcement 3000 is folded onto itself along a folding line $F_L$. In particular, a folding area 3008 is folded over a securing section 3004 as indicated by arrow M to form a substantially V-shaped structure. At this point, reinforcement 3000 partially wraps a free edge of a valve leaflet. Sutures may be used to secure reinforcement 3000 in a folded condition. One or more sutures may pass over the free edge of the leaflet outside of reinforcement 3000 to secure the reinforcement 3000 in a folded condition. In such case, the suture should be more than 1mm from the free edge of the leaflet. For thicker leaflets, it may be necessary to enlarge the folding area 3008 to allow the reinforcement 3000 to wrap over the free edge of the leaflet. Folding area 3008 defines cutout 3010 which may be substantially V-shaped for straddling the leaflets.

Securing section 3004 has a base 3006 aligned with an eyelet at the proximal end of a support post, and an angled side 3014 oriented at an oblique angle relative to folding line $F_L$ and base 3006. Angled side 3014 of securing section 3004 biases the valve opening away from a support post. For instance, angled side 3014 may bias the valve opening about 3 mm away from a support post.

As discussed above, reinforcement 3000 may optionally include a flap 3002 which provides additional securement to the support post. For example, additional sutures may attach the flap 3002 to the support post. Flap 3002 may also protect moving leaflets from knots securing the reinforcement 3000 to the support post. The distance between the edge of flap 3002 and angled side 3014 along folding line $F_L$ should be sufficient to keep the leaflets from opening against the stent. Reinforcement 3000 may be attached to a stent $S_T$ as shown in FIG. 33A. Regardless of the manner in which stent $S_T$ is deformed, as shown in FIGS. 33B and 33C, there is a low likelihood of the valve leaflet abrading against the stent.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a stent having a proximal end, a distal end, an expanded condition and a collapsed condition, the stent including:
a plurality of proximal cells at the proximal end;
a plurality of distal cells at the distal end, the distal cells being longitudinally spaced apart from the proximal cells;
a plurality of support posts connected to the proximal cells, the support posts being spaced from one another in a circumferential direction of the stent; and
a plurality of support struts, each of the support struts having a first end connected to a respective one of the support posts and a second end connected to at least one of the distal cells; and
a valve structure connected to the stent.

2. The prosthetic heart valve as claimed in claim 1, wherein the second end of each of the support struts is connected to two of the distal cells.

3. The prosthetic heart valve as claimed in claim 1, wherein each of the support struts is a bifurcated support strut having a first end connected to one of the support posts and a second end connected to a plurality of the distal cells.

4. The prosthetic heart valve as claimed in claim 3, wherein each of the bifurcated support struts has a first leg connected to one of the support posts and a pair of second legs connected to the distal cells, the first leg being connected to the pair of second legs at a transition point, each of the second legs in the pair of second legs having a proximal portion connected to the transition point and a distal portion connected to one of the distal cells, the proximal portion of the second legs being spaced closer together in the circumferential direction of the stent than the distal portion of the second legs.

5. The prosthetic heart valve as claimed in claim 4, wherein the first leg in each of the bifurcated support struts has a tightly folded C-shape.

6. The prosthetic heart valve as claimed in claim 1, wherein two of the support struts are connected to each of the support posts.

7. The prosthetic heart valve as claimed in claim 6, wherein the stent is devoid of structure in the circumferential direction between the support struts connected to one of the support posts and the support struts connected to an adjacent one of the support posts and from the first ends of the support struts to the second ends of the support struts.

8. The prosthetic heart valve as claimed in claim 1, wherein each of the support posts has a proximal end facing the proximal end of the stent and a distal end facing the distal end of the stent, the first ends of the support struts being connected to the distal ends of the support posts.

9. The prosthetic heart valve as claimed in claim 1, wherein two of the proximal cells are connected to each of the support posts, one of the proximal cells being connected to a first lateral side of the support post and another of the proximal cells being connected to a second lateral side of the support post opposite the first lateral side.

10. The prosthetic heart valve as claimed in claim 1, wherein each of the support struts includes an end portion adjacent the first end, the end portion including a first arm connected to one of the support posts and a second arm connected to one of the proximal cells immediately adjacent the one support post.

11. The prosthetic heart valve as claimed in claim 10, wherein the first arm has a U-shape.

12. The prosthetic heart valve as claimed in claim 1, wherein each of the support struts has a proximal end portion adjacent the first end, a distal end portion adjacent the second end, and an intermediate portion between the proximal end portion and the distal end portion, the intermediate portion having a sinusoidal configuration.

13. The prosthetic heart valve as claimed in claim 12, wherein the stent includes a greater number of distal cells than proximal cells.

14. The prosthetic heart valve as claimed in claim 1, wherein the plurality of proximal cells collectively define a first end spaced from the proximal end of the stent, and each of the support posts has a distal end positioned closer to the distal end of the stent than the first end of the proximal cells in the collapsed condition of the stent.

15. The prosthetic heart valve as claimed in claim 1, wherein the stent includes a greater number of distal cells than proximal cells.

16. The prosthetic heart valve as claimed in claim 1, wherein each of the support posts has a proximal end and a distal end, the proximal end of the stent extending proximally of the proximal ends of the support posts in the collapsed condition of the stent.

17. The prosthetic heart valve as claimed in claim 1, wherein the stent is devoid of structure in the circumferential direction between the support strut connected to one of the support posts and the support strut connected to an adjacent one of the support posts and from the first ends of the support struts to the second ends of the support struts.

* * * * *